(12) United States Patent
Hooker

(10) Patent No.: US 12,410,128 B1
(45) Date of Patent: Sep. 9, 2025

(54) THERAPEUTIC ALKALOID COMPOUNDS

(71) Applicant: Sensorium Therapeutics, Inc., Boston, MA (US)

(72) Inventor: Jacob M. Hooker, Winchester, MA (US)

(73) Assignee: Sensorium Therapeutics, Inc., Boston, MA (US)

( * ) Notice: Subject to any disclaimer, the term of this patent is extended or adjusted under 35 U.S.C. 154(b) by 89 days.

(21) Appl. No.: 18/134,724

(22) Filed: Apr. 14, 2023

Related U.S. Application Data

(60) Provisional application No. 63/452,267, filed on Mar. 15, 2023, provisional application No. 63/331,428, filed on Apr. 15, 2022.

(51) Int. Cl.
*C07D 209/08* (2006.01)

(52) U.S. Cl.
CPC .................. *C07D 209/08* (2013.01)

(58) Field of Classification Search
CPC ................................... C07D 209/08
USPC ....................................... 514/415
See application file for complete search history.

(56) References Cited

U.S. PATENT DOCUMENTS

| | | | |
|---|---|---|---|
| 6,288,104 | B1 | 9/2001 | Gericke et al. |
| 8,552,051 | B2 | 10/2013 | Harvey et al. |
| 8,865,723 | B2 | 10/2014 | Gurney et al. |
| 8,980,338 | B2 | 3/2015 | Gericke et al. |
| 9,381,220 | B2 | 7/2016 | Gericke et al. |
| 10,864,239 | B1 | 12/2020 | Bytton |
| 11,173,142 | B2 | 11/2021 | Davies |

FOREIGN PATENT DOCUMENTS

| | | | | |
|---|---|---|---|---|
| CN | 102000069 | A | | 4/2011 |
| CN | 102153501 | A | | 8/2011 |
| CN | 113072576 | A | | 7/2021 |
| WO | WO-1997/046234 | A1 | | 12/1997 |
| WO | WO-2005051381 | A1 | * | 6/2005 ........... C04B 35/632 |
| WO | WO-2006/050057 | A2 | | 5/2006 |
| WO | WO-2010/106494 | A1 | | 9/2010 |
| WO | WO-2010/106495 | A1 | | 9/2010 |
| WO | WO-2014/155351 | A1 | | 10/2014 |
| WO | WO-2015/048590 | A1 | | 4/2015 |
| WO | WO-2016/049595 | A1 | | 3/2016 |
| WO | WO-2016/157045 | A1 | | 10/2016 |
| WO | WO-2021/086345 | A1 | | 5/2021 |
| WO | WO-2022/140417 | A1 | | 6/2022 |
| WO | WO-2023/004428 | A1 | | 1/2023 |
| WO | WO-2023/069455 | A1 | | 4/2023 |

OTHER PUBLICATIONS

Rehman et al., In Silico, Ex Vivo and In Vivo Studies of Roflumilast as a Potential Antidiarrheal and Antispasmodic agent: Inhibition of the PDE-4 Enzyme and Voltage-gated Ca++ ion Channels, Molecules, Feb. 24, 2020, vol. 25(4), article 1008, pp. 1-11. (Year: 2020).*
Harvey et al., Pharmacological actions of the South African medicinal and functional food plant *Sceletium tortuosum* and its principal alkaloids, Journal of Ethnopharmacology, 2011, vol. 37, pp. 1124-1129. (Year: 2011).*
Meyer et al., GC-MS, LC-MS n, LC-high resolution-MS n, and NMR studies on the metabolism and toxicological detection of mesembrine and mesembrenone, the main alkaloids of the legal high "Kanna" isolated from Sceletium tortuosum, Analytical and bioanalytical chemistry, 2015, vol. 407, pp. 761-778 (Year: 2015).*
Patani et al., Bioisosterism: A Rational Approach in Drug Design, Chemical Reviews, 1996, vol. 96(8), pp. 3147-3175 (Year: 1996).*
Dimpfel et al., "Effect of Zembrin and four of its alkaloid constituents on electric excitability of the rat hippocampus," Journal of Ethnopharmacology, 223: pp. 135-141 (2018).
Gericke et al., "Sceletium—A review update," Journal of Ethnopharmacology, 119: 653-663 (2008).
Harvey et al., "Pharmacological actions of the South African medicinal and functional food plant *Sceletium tortuosum* and its principal alkaloids," Journal of Ethnopharmacology, 137: pp. 1124-1129 (2011).
Jeffs et al., "Late stages in the biosynthesis of mesembrine: sceletenone as a precursor to the cis-3a-(3, 4-dimethoxyphenyl) octahydroindole alkaloids", *Journal of the Chemical Society, Chemical Communications* 2: 60-61 (1977).
Jeffs et al., "Sceletium alkaloids. Structures of five new bases from Sceletium namaquens". *The Journal of Organic Chemistry* 47(19): 3611-3617 (1982).
Krstenansky., "Mesembrine alkaloids: Review of their occurrence, chemistry, and pharmacology," Journal of Ethnopharmacology, 195: 10-19 (2017).
Loria et al., "Effects of Sceletium tortuosum in rats," Journal of Ethnopharmacology, 155: pp. 731-735 (2014).
Luo et al., "A network pharmacology-based approach to explore the therapeutic potential of Sceletium tortuosum in the treatment of neurodegenerative disorders," PLOS One, 17(8): 21 pages (2022).
Maphanga et al., "Mesembryanthemum tortuosum L. alkaloids modify anxiety-like bahaviour in a zebrafish model," Journal of Ethnopharmacology, 290: 13 pages (2022).
Meyer et al., "GC-MS, LC-MS n, LC-high resolution-MS n, and NMR studies on the metabolism and toxicological detection of mesembrine and mesembrenone, the main alkaloids of the legal high "Kanna" isolated from Sceletium tortuosum", *Analytical and bioanalytical chemistry* 407: 761-778 (2015).
Murbach et al., "A toxicological safety assessment of a standardized extract of Sceletium tortuosum (Zembrin) in rats," Food and Chemical Toxicology, 74: pp. 190-199 (2014).
Nell et al., "A Randomized, Double-Blind, Parallel-Group, Placebo-Controlled Trial of Extract Sceletium tortuosum (Zembrin) in Healthy Adults," The Journal of Alternative and Complementary Medicine, 19(11): 898-904 (2013).
Olatunji et al., "Sceletium tortuosum: A review on its phytochemistry, pharmacokinetics, biological, pre-clinical and clinical activities," Journal of Ethnopharmacology, 287 (2022) Article 114711, pp. 1-16.

(Continued)

*Primary Examiner* — Jeffrey H Murray
*Assistant Examiner* — Rilla Marie Samsell
(74) *Attorney, Agent, or Firm* — Foley Hoag LLP; Dana M. Gordon; Yaron I. Marciano

(57) ABSTRACT

Disclosed are compounds that are derivatives of mesembrine or mesembrenone, and related methods of preparing and using these compounds.

17 Claims, No Drawings

(56) References Cited

OTHER PUBLICATIONS

Patnala et al., "Medicinal use of Sceletium: Characterization of Phytochemical Components of Sceletium Plant Species using HPLC with UV and Electrospray Ionization—Tandem Mass Spectroscopy," J Pharm Pharm Sci, 18(4): 414-423 (2015).
Patnala, "Pharmaceutical Analysis and Quality of Complementary Medicines: Sceletium and Associated Products," Sceletium Review Thesis, Rhodes University: 251 pages (2007).
Richter et al., "PDE4 as a target for cognition enhancement," Expert Opin Ther Targets, 17(9): pp. 1011-1027 (2013).
Roscher et al., "Forensic analysis of mesembrine alkaloids in S celetium tortuosum by nonaqueous capillary electrophoresis mass spectrometry", *Electrophoresis* 33(11): 1567-1570 (2012).
Terburg et al., "Acute Effects of Sceletium tortuosum (Zembrin), a Dual 5-HT Reuptake and PDE4 Inhibitor, in the Human Amygdala and its Connection to the Hypothalamus," Neuropsychopharmacology, 38: 2708-2716 (2013).

\* cited by examiner

THERAPEUTIC ALKALOID COMPOUNDS

RELATED APPLICATIONS

This application claims the benefit of priority to U.S. Provisional Patent Application Nos. 63/331,428, filed Apr. 15, 2022; and 63/452,267, filed Mar. 15, 2023.

TECHNICAL FIELD

The present disclosure relates to the field of medicine, including the discovery of novel alkaloid compounds useful for inhibiting phosphodiesterase-4 (PDE4) and the serotonin transporter protein (5-HTT).

BACKGROUND

Certain bioactive indole alkaloid compounds obtained from plants of the genus Sceletium, such as mesembrine and mesembrenone, can inhibit serotonin (5-HT) uptake and phosphodiesterase-4 (PDE-4) and have been explored as potential treatments for certain central nervous system (CNS) conditions such as mild to moderate depression.

Phosphodiesterase-4 (PDE-4) enzymes hydrolyze the cyclic nucleotide intracellular second messengers (cAMP and cGMP), leading to inactivation or inhibition of these enzymes and resulting in elevated levels of cAMP and cGMP in the cell and prolonging the action of these enzymes on downstream signaling pathways. Four isoforms of PDE-4 enzymes (designated PDE4a, PDE4b, PDE4c and PDE4d) have been identified, with the PDE4a, PDE4b and PDE4d isoforms predominantly expressed in the brain. Signaling pathways including PDE-4 are believed to be involved in diseases and disorders such as depression. Therapeutic compounds for selective inhibition of the certain PDE4 isoforms can be utilized for the treatment or prevention of depression and/or anxiety while minimizing or alleviating detrimental effects of inhibiting other PDE4 isoenzymes. One concern with the use of known PDE4 inhibitors is the side effect of emesis, which has been observed for several candidate compounds. PDE4 inhibitors, such as the brain-penetrant inhibitor rolipram, influence central function in a dose-dependent manner, consistent with their potential use in the treatment of depression and cognitive disorders in humans. However higher doses of these compounds can give rise to mechanism-related side effects such as emesis.

Natural products obtained from plants of the genus Sceletium contain varying amounts of (−) mesembrine and (+)/(−) mesembrenone. Naturally occurring (−) mesembrine from Sceletium tortuosum has been reported as having serotonin (5-HT) uptake inhibitory activity useful in treating mental health conditions, such as mild to moderate depression, and mesembrine hydrochloride has been reported to be a phosphodiesterase 4 (PDE4) inhibitor. Naturally occurring (−) mesembrenone from Sceletium tortuosum is reported as a potent selective serotonin reuptake inhibitor (Ki=27 nM) and inhibitor of a phosphodiesterase 4 (PDE4) inhibitor. Mesembrenone is a most potent inhibitor of PDE4, while mesembrine is more selective towards the serotonin receptor.

TABLE A

Summary of analysis of the concentration response curves of alkaloids on binding to the 5-HT transporter and on activity of PDE-4B (Harvey et al., 2011)

| | 5-HT transporter ("SERT") | | PDE-4B | |
|---|---|---|---|---|
| Compound | Ki (nM) | nH | IC$_{50}$ (nM) | nH |
| Mesembrine | 1.4 | 1.0 | 7,800 | 1.3 |
| Mesembrenone | 27 | 1.0 | 470 | 0.8 |

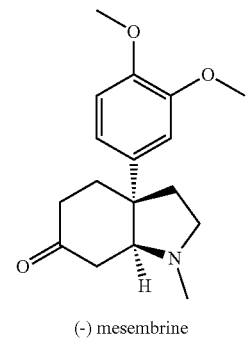

(−) mesembrine

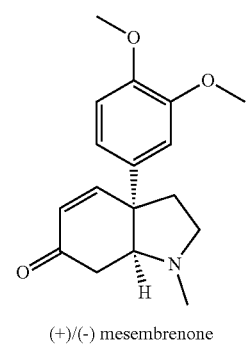

(+)/(−) mesembrenone

The therapeutic use of mesembrine and mesembrenone has been limited by the variability and instability of the content of the compounds in natural extract products, and the instability and pharmacokinetic profile of these compounds as obtained from natural products.

There remains a need in the art for an effective therapy for the treatment or prevention of depression and/or anxiety which utilizes a PDE4 inhibitor yet minimizes the side effect of nausea and/or emesis associated with the PDE4 inhibitor. There remains an unmet need for therapeutic compounds for inhibiting SERT and selectively inhibiting desired isoenzyme forms of PDE4.

SUMMARY

Described herein are compounds Formula (IA) or (IB):

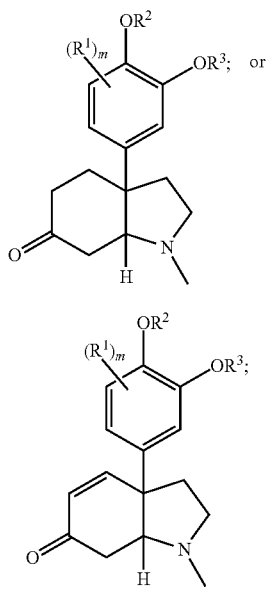

or a pharmaceutically acceptable salt thereof; wherein
$R^1$ is halo, haloalkyl, alkyl, alkenyl, alkynyl, cycloalkyl, cycloalkenyl, heterocycloalkyl, aryl, heteroaryl, —$OR^a$, —$NR^aR^b$, —CHO, —$C(O)R^a$, —$CO_2R^a$, —$C(O)NR^aR^b$, —CN, nitro, or —$P(O)OR^aOR^b$;
$R^2$ is methyl or halomethyl;
$R^3$ is methyl, halomethyl, or benzyl;
m is 0, 1, 2, or 3; and
each $R^a$ and $R^b$ is independently H, alkyl, alkenyl, cycloalkyl, heterocycloalkyl, aryl, or heteroaryl; or if an instance of $R^1$ is —$NR^aR^b$, then $R^a$ and $R^b$ may combine with the nitrogen atom to which they are attached to form heterocycloalkyl or heteroaryl;
provided the compound is not:

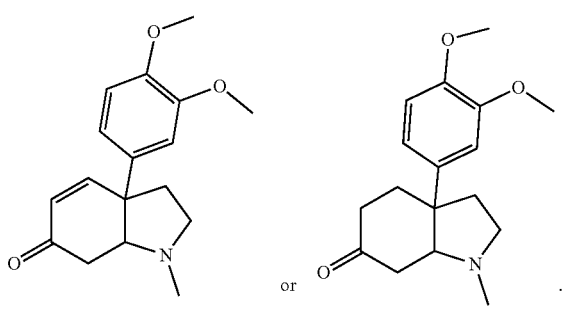 [SMILES: COc1ccc(C23C=CC(=O)CC2N(C)CC3)cc1OC ; COc1ccc(C23CCC(=O)CC2N(C)CC3)cc1OC]

In certain embodiments, the compound is a compound of Formula (IA) or Formula (IB) that is not mesembrine or mesembrenone, wherein
$R^1$ is halo, haloalkyl, alkyl, alkenyl, alkynyl, cycloalkyl, cycloalkenyl, heterocycloalkyl, aryl, heteroaryl, —$OR^a$, —$NR^aR^b$, —CHO, —$C(O)R^a$, —$CO_2R^a$, —$C(O)NR^aR^b$, —CN, nitro, or —$P(O)OR^aOR^b$;
$R^2$ is methyl or halomethyl;
$R^3$ is methyl or halomethyl;
m is 0, 1, 2, or 3; and
each $R^a$ and $R^b$ is independently H, alkyl, alkenyl, cycloalkyl, heterocycloalkyl, aryl, or heteroaryl; or if an instance of $R^1$ is —$NR^aR^b$, then $R^a$ and $R^b$ may combine with the nitrogen atom to which they are attached to form heterocycloalkyl or heteroaryl.

In certain embodiments, the compound is a compound of Formula (IA) or Formula (IB), wherein
$R^1$ is halo, haloalkyl, alkyl, alkenyl, alkynyl, cycloalkyl, cycloalkenyl, heterocycloalkyl, aryl, heteroaryl, —$OR^a$, —$NR^aR^b$, —CHO, —$C(O)R^a$, —$CO_2R^a$, —$C(O)NR^aR^b$, —CN, nitro, or —$P(O)OR^aOR^b$;
$R^2$ is methyl or halomethyl;
$R^3$ is methyl, halomethyl, or benzyl;
m is 1, 2, or 3; and
each $R^a$ and $R^b$ is independently H, alkyl, alkenyl, cycloalkyl, heterocycloalkyl, aryl, or heteroaryl; or if an instance of $R^1$ is —$NR^aR^b$, then $R^a$ and $R^b$ may combine with the nitrogen atom to which they are attached to form heterocycloalkyl or heteroaryl.

In certain embodiments, the compound is a compound of Formula (IA) or Formula (IB) that is not mesembrine or mesembrenone, wherein
$R^1$ is halo, haloalkyl, alkyl, alkenyl, alkynyl, cycloalkyl, cycloalkenyl, heterocycloalkyl, aryl, heteroaryl, —$OR^a$, —$NR^aR^b$, —CHO, —$C(O)R^a$, —$CO_2R^a$, —$C(O)NR^aR^b$, —CN, nitro, or —$P(O)OR^aOR^b$;
$R^2$ is methyl or halomethyl;
$R^3$ is benzyl;
m is 0, 1, 2, or 3; and
each $R^a$ and $R^b$ is independently H, alkyl, alkenyl, cycloalkyl, heterocycloalkyl, aryl, or heteroaryl; or if an instance of $R^1$ is —$NR^aR^b$, then $R^a$ and $R^b$ may combine with the nitrogen atom to which they are attached to form heterocycloalkyl or heteroaryl.

In certain embodiments, the compound is a compound of Formula (IA), wherein
$R^1$ is halo;
$R^2$ is methyl or halomethyl;
$R^3$ is methyl, halomethyl, or benzyl;
m is 1, 2, or 3; and
each $R^a$ and $R^b$ is independently H, alkyl, alkenyl, cycloalkyl, heterocycloalkyl, aryl, or heteroaryl; or if an instance of $R^1$ is —$NR^aR^b$, then $R^a$ and $R^b$ may combine with the nitrogen atom to which they are attached to form heterocycloalkyl or heteroaryl.

In certain embodiments, the compound is a compound of Formula (IA), wherein
$R^1$ is halo;
$R^2$ is methyl or halomethyl;
$R^3$ is methyl or halomethyl;
m is 1, 2, or 3; and
each $R^a$ and $R^b$ is independently H, alkyl, alkenyl, cycloalkyl, heterocycloalkyl, aryl, or heteroaryl; or if an instance of $R^1$ is —$NR^aR^b$, then $R^a$ and $R^b$ may combine with the nitrogen atom to which they are attached to form heterocycloalkyl or heteroaryl.

In certain embodiments, the compound is a compound of Formula (IB), wherein
$R^1$ is halo;
$R^2$ is methyl or halomethyl;
$R^3$ is methyl, halomethyl, or benzyl;
m is 1, 2, or 3; and
each $R^a$ and $R^b$ is independently H, alkyl, alkenyl, cycloalkyl, heterocycloalkyl, aryl, or heteroaryl; or if an instance of $R^1$ is —$NR^aR^b$, then $R^a$ and $R^b$ may combine with the nitrogen atom to which they are attached to form heterocycloalkyl or heteroaryl.

In certain embodiments, the compound is a compound of Formula (IB), wherein $R^1$ is halo;

$R^2$ is methyl or halomethyl;

$R^3$ is methyl or halomethyl;

m is 1, 2, or 3; and each $R^a$ and $R^b$ is independently H, alkyl, alkenyl, cycloalkyl, heterocycloalkyl, aryl, or heteroaryl; or if an instance of $R^1$ is —$NR^aR^b$, then $R^a$ and $R^b$ may combine with the nitrogen atom to which they are attached to form heterocycloalkyl or heteroaryl.

In certain embodiments, the compound is a compound of Formula (IA) or Formula (IB), wherein $R^1$ is halo, haloalkyl, alkyl, cycloalkyl, —$OR^a$, —$NR^aR^b$, —CHO, —$C(O)R^a$, —$CO_2R^a$, —$C(O)NR^aR^b$, —CN, or nitro;

$R^2$ is methyl or halomethyl;

$R^3$ is methyl, halomethyl, or benzyl;

m is 1, 2, or 3; and each $R^a$ and $R^b$ is independently H, or alkyl.

In certain embodiments, the compound is a compound of Formula (IA) or Formula (IB), wherein $R^1$ is halo, haloalkyl, alkyl, cyclopropyl, —$NH_2$, —$NO_2$, —$C(O)R^a$, or —CN;

$R^2$ is methyl or halomethyl;

$R^3$ is methyl, halomethyl, or benzyl;

m is 1, 2, or 3; and each $R^a$ and $R^b$ is independently H or alkyl.

In certain embodiments, the compound is a compound of Formula (IA) or Formula (IB), wherein $R^1$ is halo, haloalkyl, alkyl, cyclopropyl, —$NH_2$, —$NO_2$, —$C(O)R^a$, or —CN;

$R^2$ is methyl or halomethyl;

$R^3$ is methyl or halomethyl;

m is 1, 2, or 3; and each $R^a$ and $R^b$ is independently H, or alkyl.

In certain embodiments, the present disclosure provides a method of treating a central nervous condition, comprising administering to a subject in need thereof an effective amount of a compound of the present disclosure.

In certain embodiments, the present disclosure provides a method of treating a condition by administering a PDE4 inhibitor, comprising administering to a subject in need thereof an effective amount a compound of the present disclosure.

Numerous embodiments are further provided that can be applied to any aspect of the present invention described herein.

DETAILED DESCRIPTION

The present invention is based, at least in part, on analogs of mesembrine and mesembrenone. Although (−) mesembrine is bioactive with certain desirable pharmacologic effects, certain other properties are less than ideal for use as a therapeutic. For example, the pharmacokinetics described for (−) mesembrine show rapid metabolism and excretion, which an undesirably low half-life in plasma of less than 2 hours. To take advantage of the desirable properties of mesembrine and mesembrenone, compounds have been developed and described here.

Compounds of the Invention

In certain aspects, the invention relates to compounds of Formula (IA) or (IB):

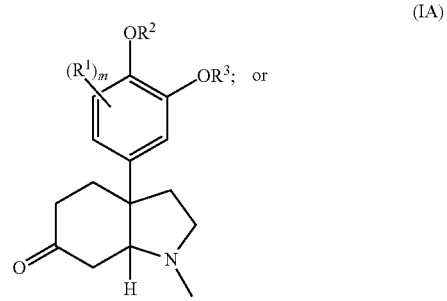

(IA)

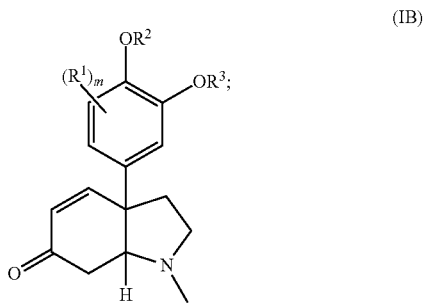

(IB)

or a pharmaceutically acceptable salt thereof; wherein $R^1$ is halo, haloalkyl, alkyl, alkenyl, alkynyl, cycloalkyl, cycloalkenyl, heterocycloalkyl, aryl, heteroaryl, —$OR^a$, —$NR^aR^b$, —CHO, —$C(O)R^a$, —$CO_2R^a$, —$C(O)NR^aR^b$, —CN, nitro, or —$P(O)OR^aOR^b$;

$R^2$ is methyl or halomethyl;

$R^3$ is methyl, halomethyl, or benzyl;

m is 0, 1, 2, or 3; and each $R^a$ and $R^b$ is independently H, alkyl, alkenyl, cycloalkyl, heterocycloalkyl, aryl, or heteroaryl; or if an instance of $R^1$ is —$NR^aR^b$, then $R^a$ and $R^b$ may combine with the nitrogen atom to which they are attached to form heterocycloalkyl or heteroaryl;

provided the compound is not:

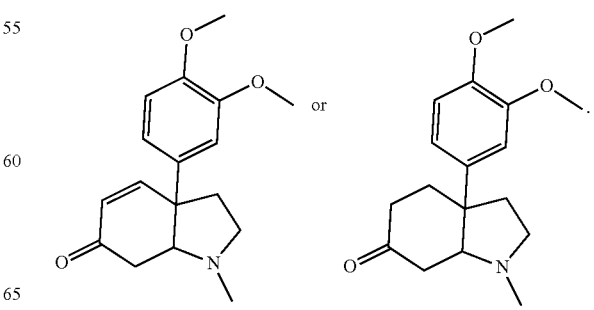

In certain aspects, the invention relates to compounds of Formula (IA):

(IA)

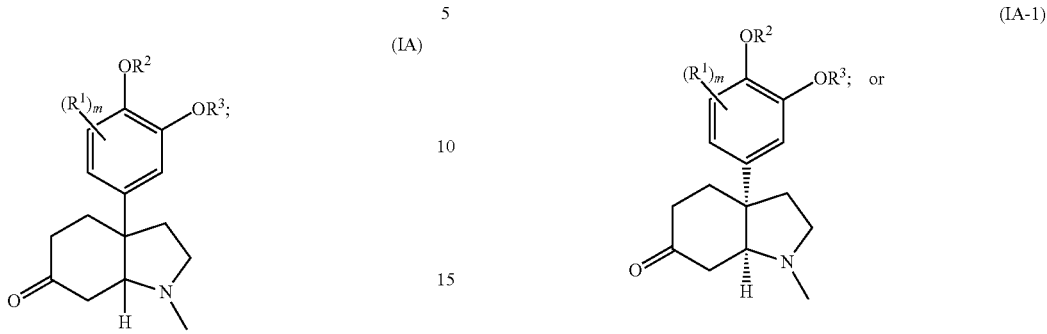

or a pharmaceutically acceptable salt thereof; wherein

R¹ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;

R² is methyl or halomethyl;

R³ is methyl, halomethyl, or benzyl;

m is 1, 2, or 3; and each R$^a$ and R$^b$ is independently H, alkyl, alkenyl, cycloalkyl, heterocycloalkyl, aryl, or heteroaryl; or if an instance of R¹ is —NR$^a$R$^b$, then R$^a$ and R$^b$ may combine with the nitrogen atom to which they are attached to form heterocycloalkyl or heteroaryl.

In certain aspects, the invention relates to compounds of Formula (IB):

(IB)

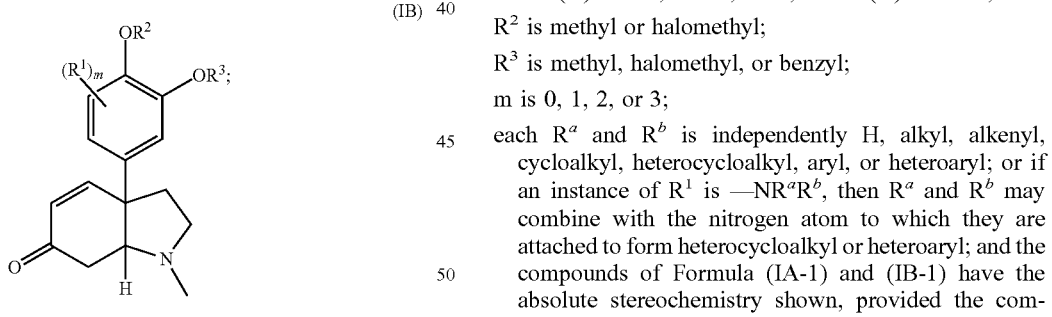

or a pharmaceutically acceptable salt thereof; wherein

R¹ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;

R² is methyl or halomethyl;

R³ is methyl, halomethyl, or benzyl;

m is 1, 2, or 3; and each R$^a$ and R$^b$ is independently H, alkyl, alkenyl, cycloalkyl, heterocycloalkyl, aryl, or heteroaryl; or if an instance of R¹ is —NR$^a$R$^b$, then R$^a$ and R$^b$ may combine with the nitrogen atom to which they are attached to form heterocycloalkyl or heteroaryl.

In certain embodiments, the compound is of Formula (IA-1) or (IB-1):

(IA-1)

(IB-1)

or a pharmaceutically acceptable salt thereof; wherein

R¹ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;

R² is methyl or halomethyl;

R³ is methyl, halomethyl, or benzyl;

m is 0, 1, 2, or 3;

each R$^a$ and R$^b$ is independently H, alkyl, alkenyl, cycloalkyl, heterocycloalkyl, aryl, or heteroaryl; or if an instance of R¹ is —NR$^a$R$^b$, then R$^a$ and R$^b$ may combine with the nitrogen atom to which they are attached to form heterocycloalkyl or heteroaryl; and the compounds of Formula (IA-1) and (IB-1) have the absolute stereochemistry shown, provided the compound is not:

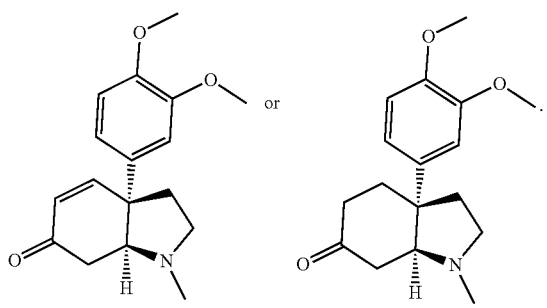 [SMILES: COc1ccc([C@@]23C=CC(=O)C[C@@H]2N(C)CC3)cc1OC ; COc1ccc([C@@]23CCC(=O)C[C@@H]2N(C)CC3)cc1OC]

In certain embodiments, the compound is of Formula (IA-1):

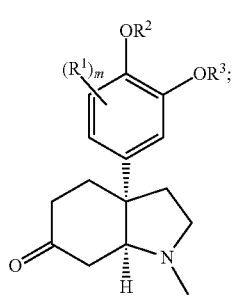
(IA-1)

or a pharmaceutically acceptable salt thereof; wherein
R$^1$ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;
R$^2$ is methyl or halomethyl;
R$^3$ is methyl, halomethyl, or benzyl;
m is 1, 2, or 3;
each R$^a$ and R$^b$ is independently H, alkyl, alkenyl, cycloalkyl, heterocycloalkyl, aryl, or heteroaryl; or if an instance of R$^1$ is —NR$^a$R$^b$, then R$^a$ and R$^b$ may combine with the nitrogen atom to which they are attached to form heterocycloalkyl or heteroaryl; and the compounds of Formula (IA-1) have the absolute stereochemistry shown.

In certain embodiments, the compound is of Formula (IB-1):

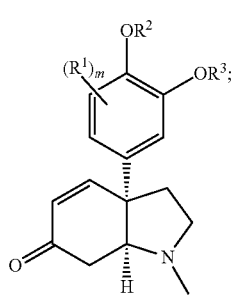
(IB-1)

or a pharmaceutically acceptable salt thereof; wherein
R$^1$ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;
R$^2$ is methyl or halomethyl;
R$^3$ is methyl, halomethyl, or benzyl;
m is 1, 2, or 3;
each R$^a$ and R$^b$ is independently H, alkyl, alkenyl, cycloalkyl, heterocycloalkyl, aryl, or heteroaryl; or if an instance of R$^1$ is —NR$^a$R$^b$, then R$^a$ and R$^b$ may combine with the nitrogen atom to which they are attached to form heterocycloalkyl or heteroaryl; and the compounds of Formula (IA-1) and (IB-1) have the absolute stereochemistry shown.

In certain embodiments, the compound is of Formula (IA-1):

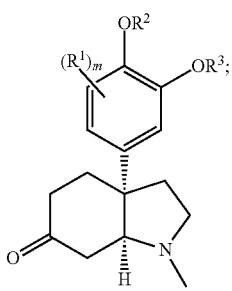
(IA-1)

or a pharmaceutically acceptable salt thereof; wherein
R$^1$ is halo, haloalkyl, alkyl, cyclopropyl, —NH$_2$, —NO$_2$, —C(O)R$^a$, or —CN;
R$^2$ is methyl or halomethyl;
R$^3$ is methyl, halomethyl, or benzyl;
m is 1, 2, or 3;
R$^a$ is independently H or alkyl; and
the compounds of Formula (IA-1) have the absolute stereochemistry shown.

In certain embodiments, the compound is of Formula (IB-1):

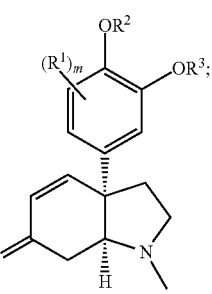
(IB-1)

or a pharmaceutically acceptable salt thereof; wherein
R$^1$ is halo, haloalkyl, alkyl, cyclopropyl, —NH$_2$, —NO$_2$, —C(O)R$^a$, or —CN;
R$^2$ is methyl or halomethyl;
R$^3$ is methyl, halomethyl, or benzyl;
m is 1, 2, or 3;
R$^a$ is H or alkyl; and
the compounds of Formula (IB-1) have the absolute stereochemistry shown.

In certain embodiments, the compound is of Formula (IA) or Formula (IA-1) or a pharmaceutically acceptable salt thereof.

In certain embodiments, the compound is of Formula (IB) or Formula (IB-1) or a pharmaceutically acceptable salt thereof.

In certain embodiments, m is 1, 2, or 3. For example, m can be 1 or m can be 1 or 2. In certain embodiments, m is 0. In certain embodiments, m is 1. In certain embodiments, m is 2.

In certain embodiments, the compound is of Formula (IA), Formula (IA-1), Formula (IB) or Formula (IB-1) that is not (−) mesembrine or (+)/(−) mesembrenone. In certain embodiments, the compound is of Formula (IA), Formula (IA-1), Formula (IB) or Formula (IB-1) that is not (−)-mesembrine or (+)/(−) mesembrenone, wherein R¹ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;

R² is methyl or halomethyl;

R³ is methyl or halomethyl;

m is 0, 1, 2, or 3;

each R$^a$ and R$^b$ is independently H, alkyl, alkenyl, cycloalkyl, heterocycloalkyl, aryl, or heteroaryl; or if an instance of R¹ is —NR$^a$R$^b$, then R$^a$ and R$^b$ may combine with the nitrogen atom to which they are attached to form heterocycloalkyl or heteroaryl.

In certain embodiments, the compound is of Formula (IA), Formula (IA-1), Formula (IB) or Formula (IB-1), wherein R¹ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;

R² is methyl or halomethyl;

R³ is methyl or halomethyl;

m is 1, 2, or 3; and each R$^a$ and R$^b$ is independently H, alkyl, alkenyl, cycloalkyl, heterocycloalkyl, aryl, or heteroaryl; or if an instance of R¹ is —NR$^a$R$^b$, then R$^a$ and R$^b$ may combine with the nitrogen atom to which they are attached to form heterocycloalkyl or heteroaryl.

In certain embodiments, the compound is of Formula (IA-2), (IA-3), (IB-2), or (IB-3):

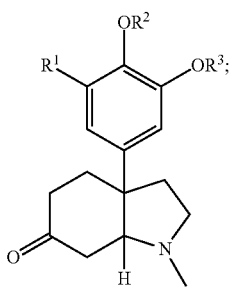

(IA-2)

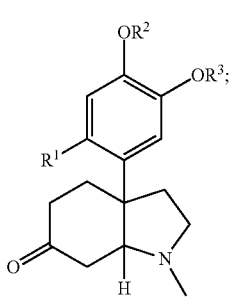

(IA-3)

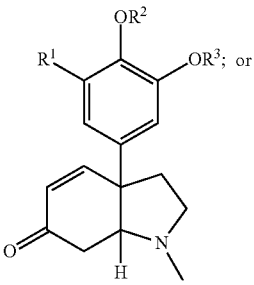

(IA-2)

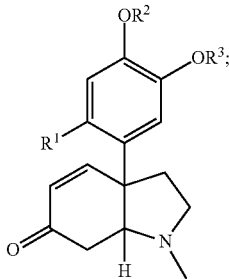

(IA-3)

or a pharmaceutically acceptable salt thereof; wherein

R¹ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;

R² is methyl or halomethyl;

R³ is methyl, halomethyl, or benzyl; and each R$^a$ and R$^b$ is independently H, alkyl, alkenyl, cycloalkyl, heterocycloalkyl, aryl, or heteroaryl; or if an instance of R¹ is —NR$^a$R$^b$, then R$^a$ and R$^b$ may combine with the nitrogen atom to which they are attached to form heterocycloalkyl or heteroaryl.

In certain embodiments, the compound is of Formula (IA-2), (IA-3), (IB-2), or (IB-3): wherein R¹ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;

R² is methyl or halomethyl;

R³ is methyl or halomethyl; and each R$^a$ and R$^b$ is independently H, alkyl, alkenyl, cycloalkyl, heterocycloalkyl, aryl, or heteroaryl; or if an instance of R¹ is —NR$^a$R$^b$, then R$^a$ and R$^b$ may combine with the nitrogen atom to which they are attached to form heterocycloalkyl or heteroaryl.

In certain embodiments, the compound is of Formula (IA-2) or a pharmaceutically acceptable salt thereof.

In certain embodiments, the compound is of Formula (IA-3) or a pharmaceutically acceptable salt thereof.

In certain embodiments, the compound is of Formula (IB-2) or a pharmaceutically acceptable salt thereof).

In certain embodiments, the compound is of Formula (IB-3) or a pharmaceutically acceptable salt thereof.

In certain embodiments, the compound is of Formula (IA-4), (IA-5), (IB-4), or (IB-5):

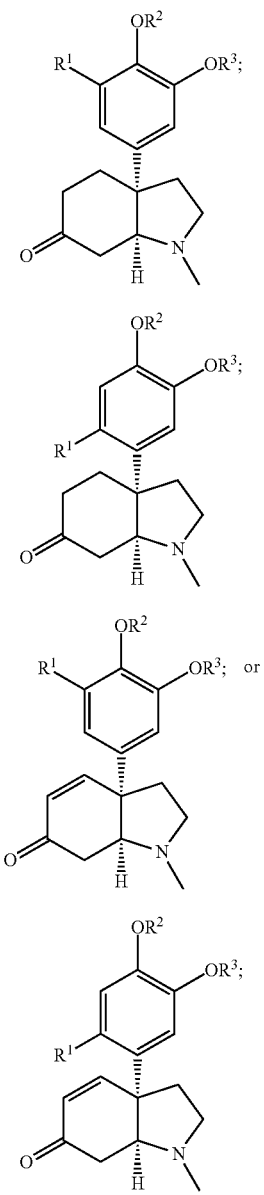

or a pharmaceutically acceptable salt thereof; wherein $R^1$ is halo, haloalkyl, alkyl, alkenyl, alkynyl, cycloalkyl, cycloalkenyl, heterocycloalkyl, aryl, heteroaryl, —$OR^a$, —$NR^aR^b$, —CHO, —C(O)$R^a$, —$CO_2R^a$, —C(O)$NR^aR^b$, —CN, nitro, or —P(O)$OR^aOR^b$;

$R^2$ is methyl or halomethyl;

$R^3$ is methyl, halomethyl, or benzyl;

each $R^a$ and $R^b$ is independently H, alkyl, alkenyl, cycloalkyl, heterocycloalkyl, aryl, or heteroaryl; or if an instance of $R^1$ is —$NR^aR^b$, then $R^a$ and $R^b$ may combine with the nitrogen atom to which they are attached to form heterocycloalkyl or heteroaryl; and the compounds of Formula (IA-4), (IA-5), (IB-4), and (IB-5) have the absolute stereochemistry shown.

In certain embodiments, the compound is of Formula (IA-4), (IA-5), (IB-4), or (IB-5), wherein $R^1$ is halo, haloalkyl, alkyl, alkenyl, alkynyl, cycloalkyl, cycloalkenyl, heterocycloalkyl, aryl, heteroaryl, —$OR^a$, —$NR^aR^b$, —CHO, —C(O)$R^a$, —$CO_2R^a$, —C(O)$NR^aR^b$, —CN, nitro, or —P(O)$OR^aOR^b$;

$R^2$ is methyl or halomethyl;

$R^3$ is methyl or halomethyl;

each $R^a$ and $R^b$ is independently H, alkyl, alkenyl, cycloalkyl, heterocycloalkyl, aryl, or heteroaryl; or if an instance of $R^1$ is —$NR^aR^b$, then $R^a$ and $R^b$ may combine with the nitrogen atom to which they are attached to form heterocycloalkyl or heteroaryl; and the compounds of Formula (IA-4), (IA-5), (IB-4), and (IB-5) have the absolute stereochemistry shown.

In certain embodiments, the compound is of Formula (IA-4) or a pharmaceutically acceptable salt thereof.

In certain embodiments, the compound is of Formula (IA-5) or a pharmaceutically acceptable salt thereof.

In certain embodiments, the compound is of Formula (IB-4) or a pharmaceutically acceptable salt thereof.

In certain embodiments, the compound is of Formula (IB-5) or a pharmaceutically acceptable salt thereof.

In certain embodiments, wherein the compound is of Formula (IA-6), (IA-7), (IB-6), or (IB-7):

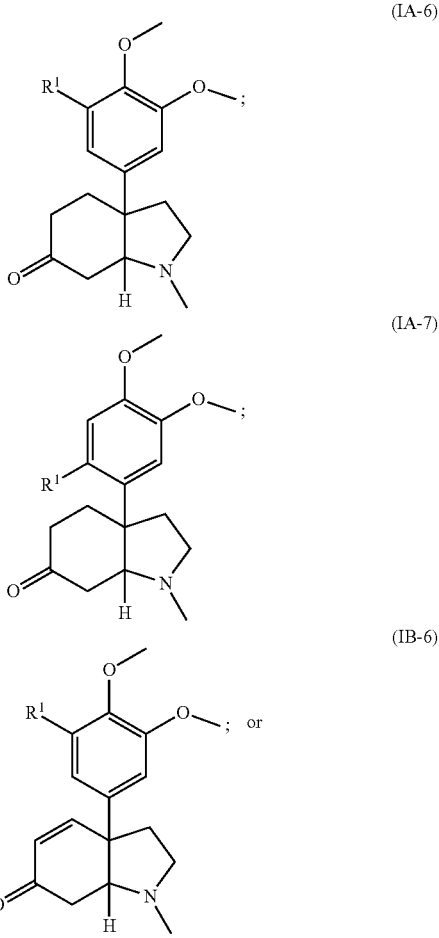

-continued (IB-7)

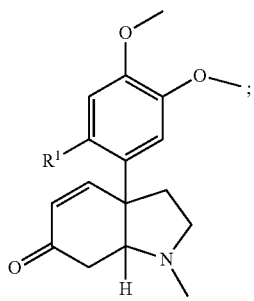

or a pharmaceutically acceptable salt thereof; wherein

R$^1$ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$; and each R$^a$ and R$^b$ is independently H, alkyl, alkenyl, cycloalkyl, heterocycloalkyl, aryl, or heteroaryl; or if an instance of R$^1$ is —NR$^a$R$^b$, then R$^a$ and R$^b$ may combine with the nitrogen atom to which they are attached to form heterocycloalkyl or heteroaryl.

In certain embodiments, the compound is of Formula (IA-6) or a pharmaceutically acceptable salt thereof.

In certain embodiments, the compound is of Formula (IA-7) or a pharmaceutically acceptable salt thereof.

In certain embodiments, the compound is of Formula (IB-6) or a pharmaceutically acceptable salt thereof.

In certain embodiments, the compound is of Formula (IB-7) or a pharmaceutically acceptable salt thereof.

In certain embodiments, the compound is of Formula (IA-8), (IA-9), (IB-8), or (IB-5):

(IA-8)

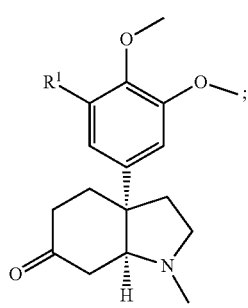

(IA-9)

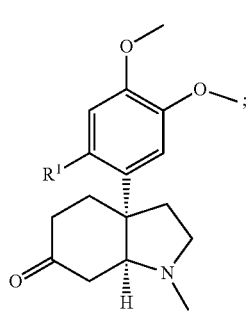

-continued (IB-8)

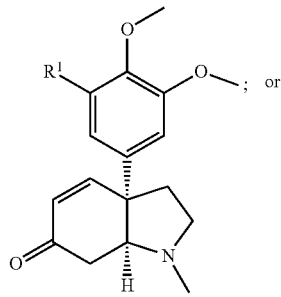

or (IB-9)

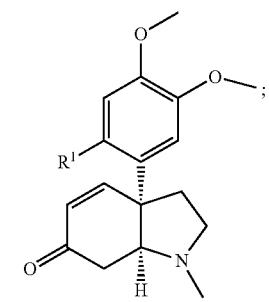

or a pharmaceutically acceptable salt thereof; wherein

R$^1$ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;

each R$^a$ and R$^b$ is independently H, alkyl, alkenyl, cycloalkyl, heterocycloalkyl, aryl, or heteroaryl; or if an instance of R$^1$ is —NR$^a$R$^b$, then R$^a$ and R$^b$ may combine with the nitrogen atom to which they are attached to form heterocycloalkyl or heteroaryl; and the compounds of Formula (IA-8), (IA-9), (IB-8), and (IB-9) have the absolute stereochemistry shown.

In certain embodiments, the compound is of Formula (IA-8) or a pharmaceutically acceptable salt thereof.

In certain embodiments, the compound is of Formula (IA-9) or a pharmaceutically acceptable salt thereof.

In certain embodiments, the compound is of Formula (IB-8) or a pharmaceutically acceptable salt thereof.

In certain embodiments, the compound is of Formula (IB-9) or a pharmaceutically acceptable salt thereof.

In certain embodiments, R$^1$ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$. In certain embodiments, R$^1$ is halo, haloalkyl, alkyl, cycloalkyl, cycloalkenyl, heterocycloalkyl, aryl, heteroaryl, —OR$^a$ (e.g., alkoxy), —NR$^a$R$^b$ (e.g., —NH$_2$), —CHO, —C(O)R$^a$ (e.g., —C(O)alkyl, such as —C(O)CH$_3$), —CN, or nitro. In some embodiments, R$^1$ is halo, haloalkyl, alkyl, cycloalkyl, heterocycloalkyl, —OR$^a$, —NR$^a$R$^b$, —CHO, C(O)R$^a$, —CN, or nitro. In some further embodiments, R$^1$ is alkyl. In some further embodiments, R$^1$ is haloalkyl.

In certain embodiments, R$^1$ is halo, cycloalkyl, —OR$^a$ (e.g., alkoxy), —NR$^a$R$^b$ (e.g., —NH$_2$), C(O)R$^a$ (e.g., —C(O)alkyl, such as —C(O)CH$_3$), —CN, or nitro. For example, R$^1$ can be halo, cycloalkyl, alkoxy, —NH$_2$, C(O)alkyl, —CN, or nitro. In some embodiments, R$^1$ is —C(O)alkyl, such as —C(O)CH$_3$. In some embodiments, R$^1$ is alkoxy, such as methoxy. In some embodiments, R$^1$ is cycloalkyl, such as cyclopropyl.

In certain embodiments, $R^1$ is halo, cyclopropyl, —OCH$_3$, —NH$_2$, —C(O)CH$_3$, —CN, or nitro. In some embodiments, $R^1$ is halo. In some embodiments, $R^1$ is —CN. In some embodiments, $R^1$ is nitro. In some embodiments, $R^1$ is —NH$_2$. In certain embodiments, $R^1$ is halo, haloalkyl, alkyl, cyclopropyl, —NH$_2$, —NO$_2$, —C(O)R$^a$, or —CN. In certain embodiments, $R^1$ is halo. In certain embodiments, $R^1$ is haloalkyl. In certain embodiments, $R^1$ is alkyl. In certain embodiments, $R^1$ is cyclopropyl. In certain embodiments, $R^1$ is —NH$_2$. In certain embodiments, $R^1$ is —NO$_2$. In certain embodiments, $R^1$ is —C(O)R$^a$, wherein R$^a$ is hydrogen or alkyl. In certain embodiments, $R^1$ is —C(O)R$^a$, wherein R$^a$ is hydrogen or methyl. In certain embodiments, $R^1$ is —CN.

In certain embodiments, $R^2$ is methyl. In further embodiments, $R^2$ is halomethyl such as a methyl substituted with at least one fluoro (e.g., CHF$_2$ or CF$_3$).

In certain embodiments, $R^3$ is methyl. In further embodiments, $R^3$ is halomethyl such as a methyl substituted with at least one fluoro (e.g., CHF$_2$ or CF$_3$). In some embodiments, $R^3$ is benzyl.

In certain embodiments, each R$^a$ and R$^b$ is independently H, alkyl (e.g., methyl), alkenyl, cycloalkyl, heterocycloalkyl, aryl, or heteroaryl; or if an instance of $R^1$ is —NR$^a$R$^b$, then R$^a$ and R$^b$ may combine with the nitrogen atom to which they are attached to form heterocycloalkyl or heteroaryl. For example, if $R^1$ is —NR$^a$R$^b$, then R$^a$ and R$^b$ may combine with the nitrogen atom to which they are attached to form

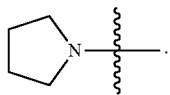

In certain embodiments, each R$^a$ and R$^b$ is independently H. In certain embodiments, each R$^a$ and R$^b$ is independently H or methyl.

In certain embodiments, the compound is selected from the group consisting of:

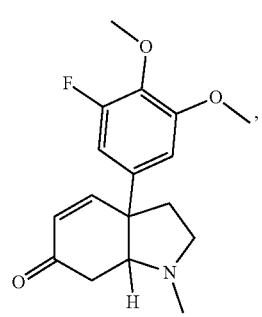, 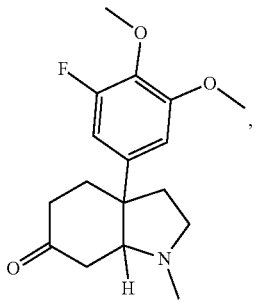,

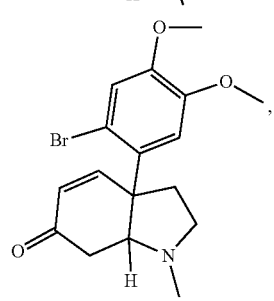, 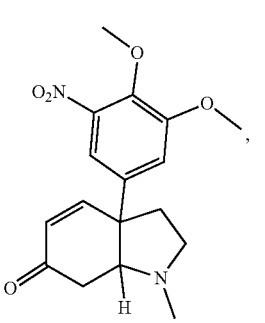,

-continued

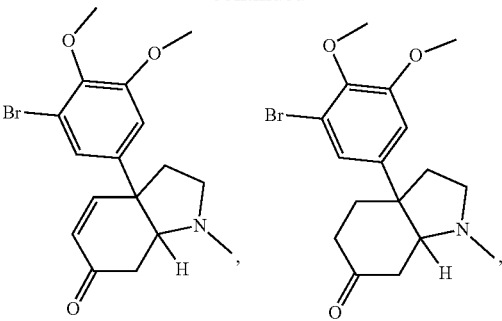

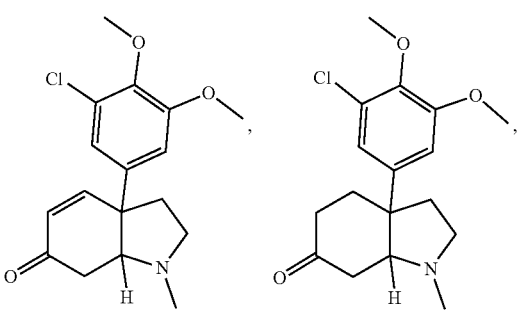

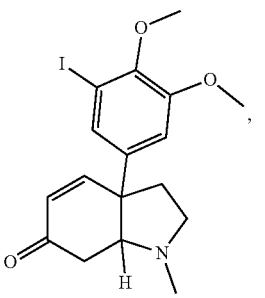, 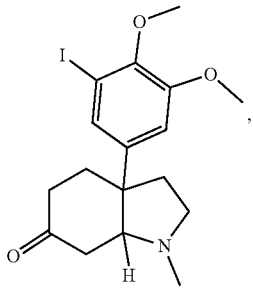,

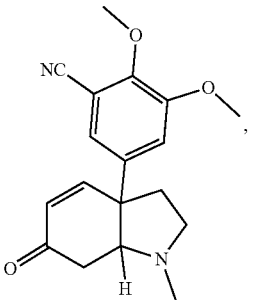, 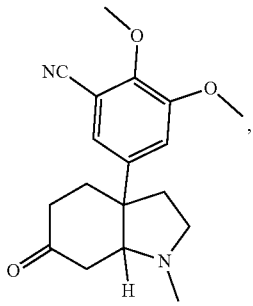,

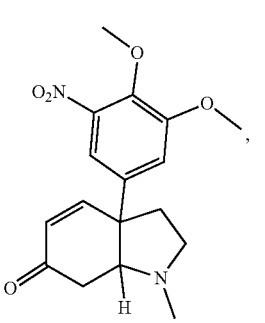, 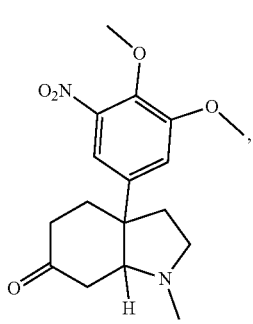

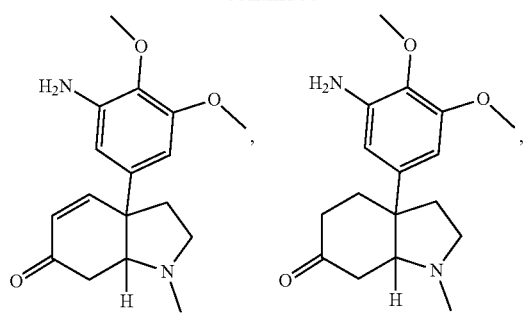
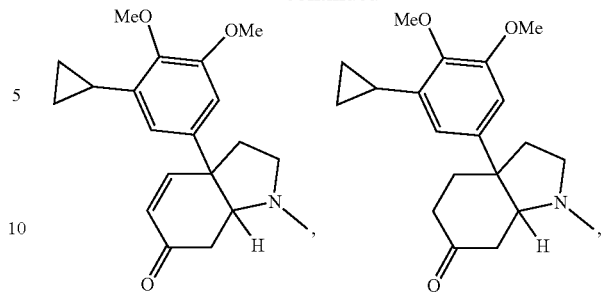
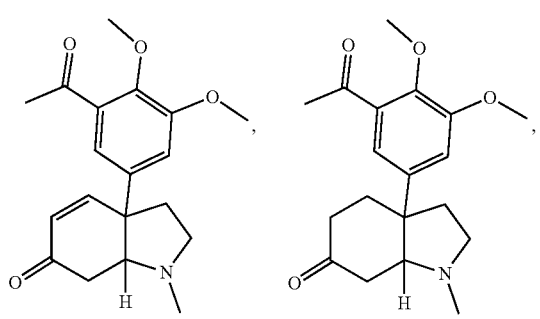
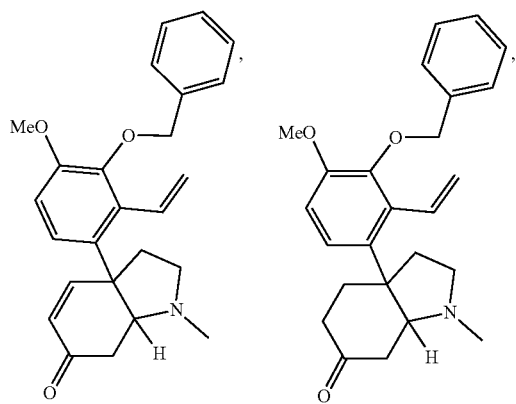
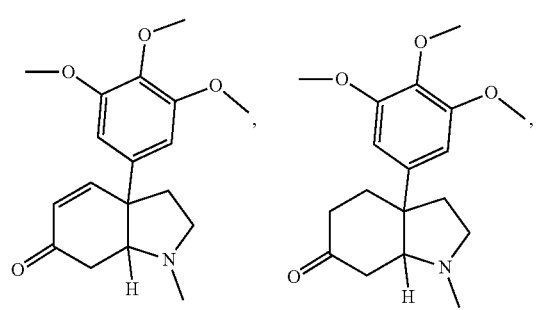
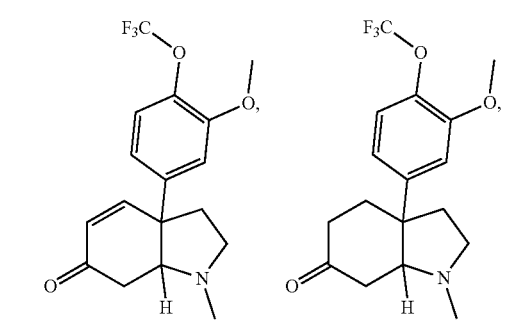
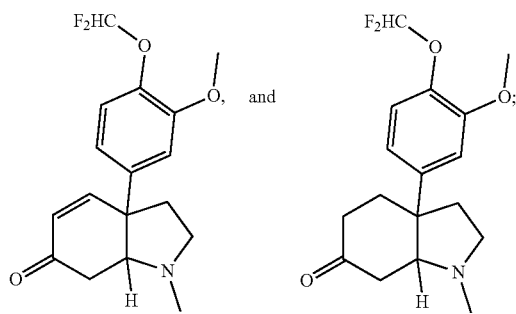
or a pharmaceutically acceptable salt thereof.
In certain embodiments, the compound is selected from the group consisting of:
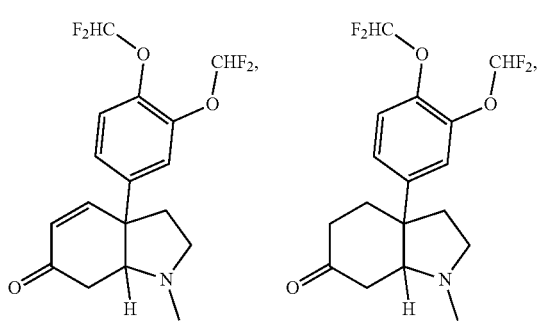
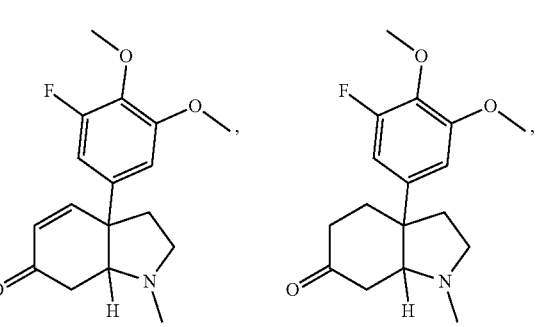

-continued
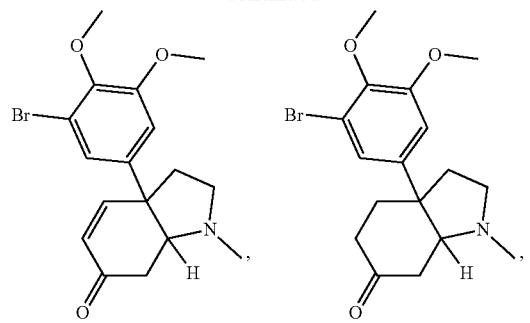
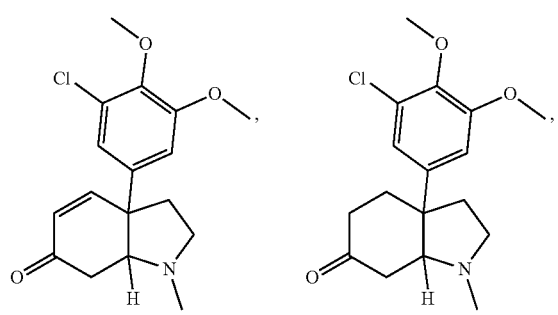
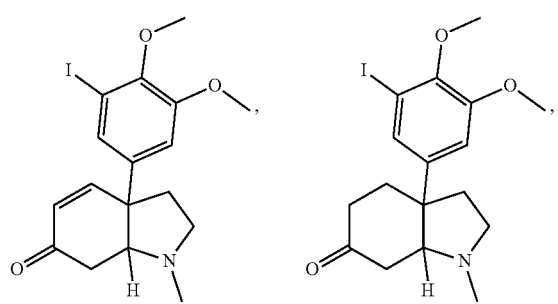
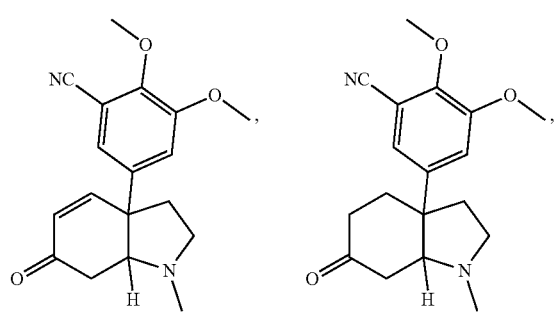
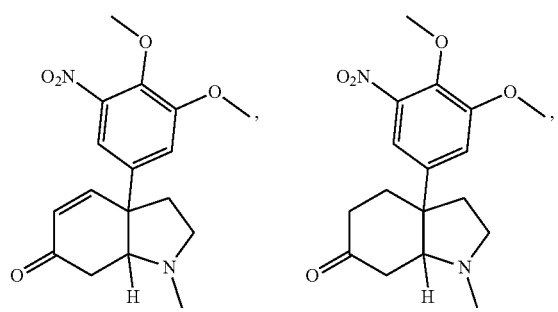
-continued
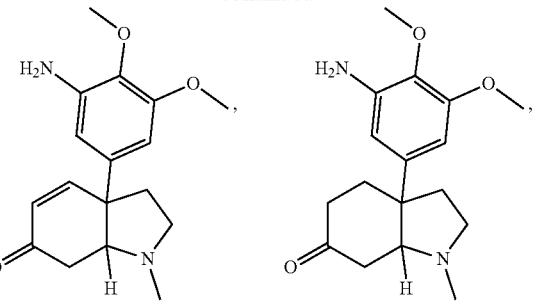
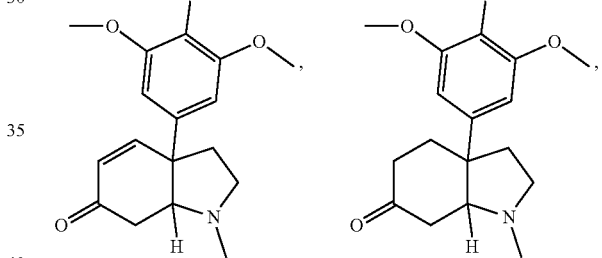
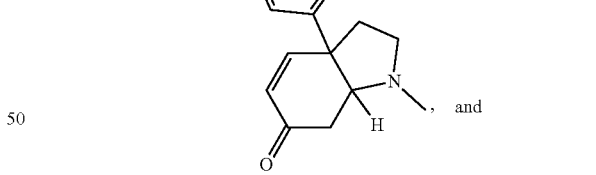
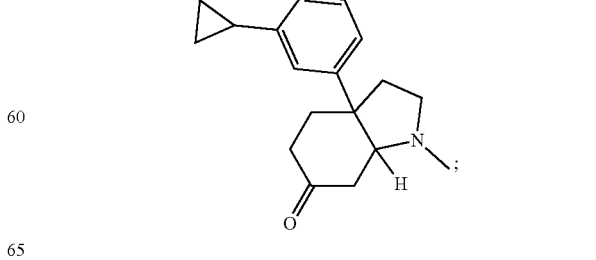
or a pharmaceutically acceptable salt thereof.

In certain embodiments, the compound is selected from the group consisting of:
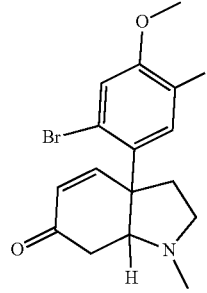 and 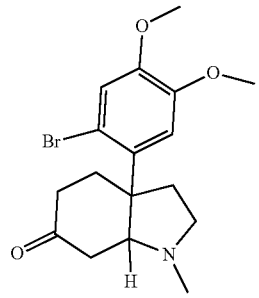,
or a pharmaceutically acceptable salt thereof. In certain embodiments, the compound is selected from the group consisting of:
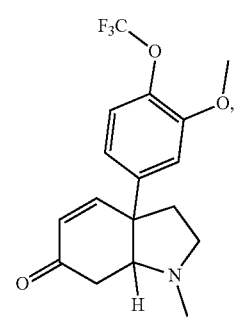 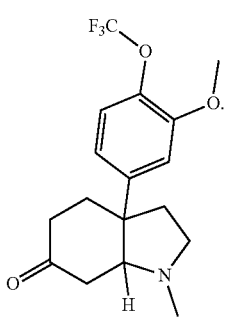
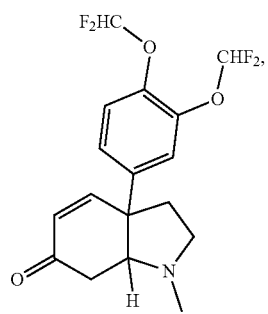 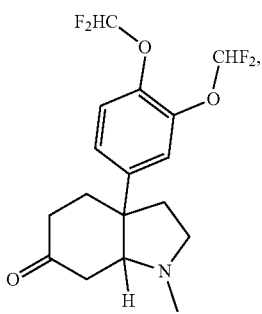
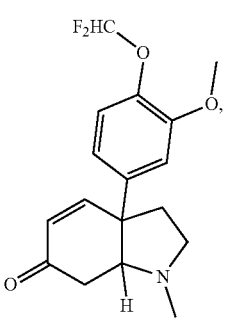 and 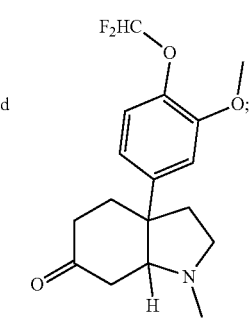;
or a pharmaceutically acceptable salt thereof.
In certain embodiments, the compound is selected from the group consisting of:
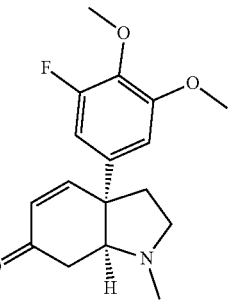 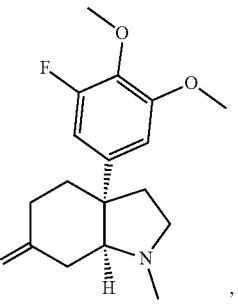,
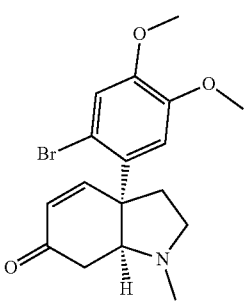 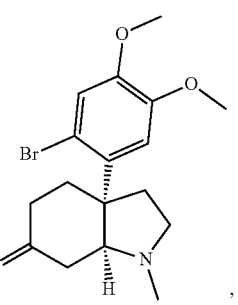,
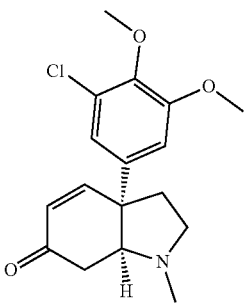 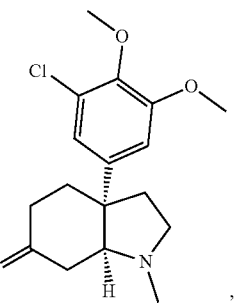,
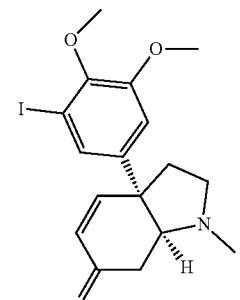 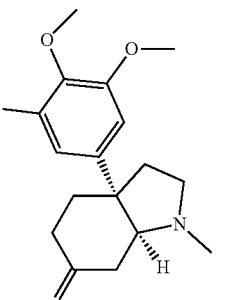,

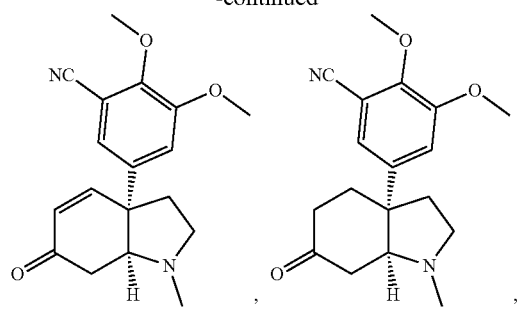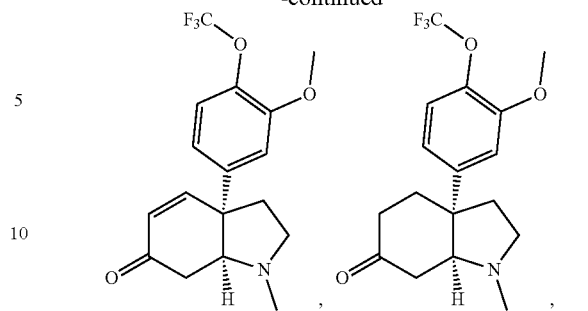
or a pharmaceutically acceptable salt thereof.

In certain embodiments, the compound is selected from the group consisting of:
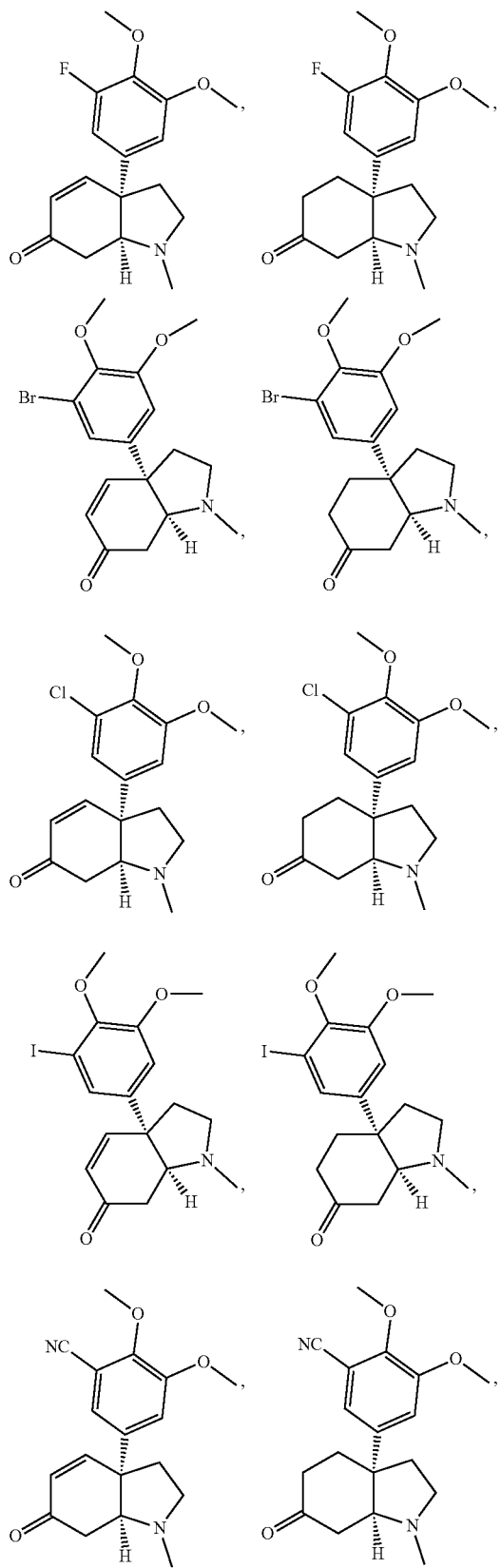
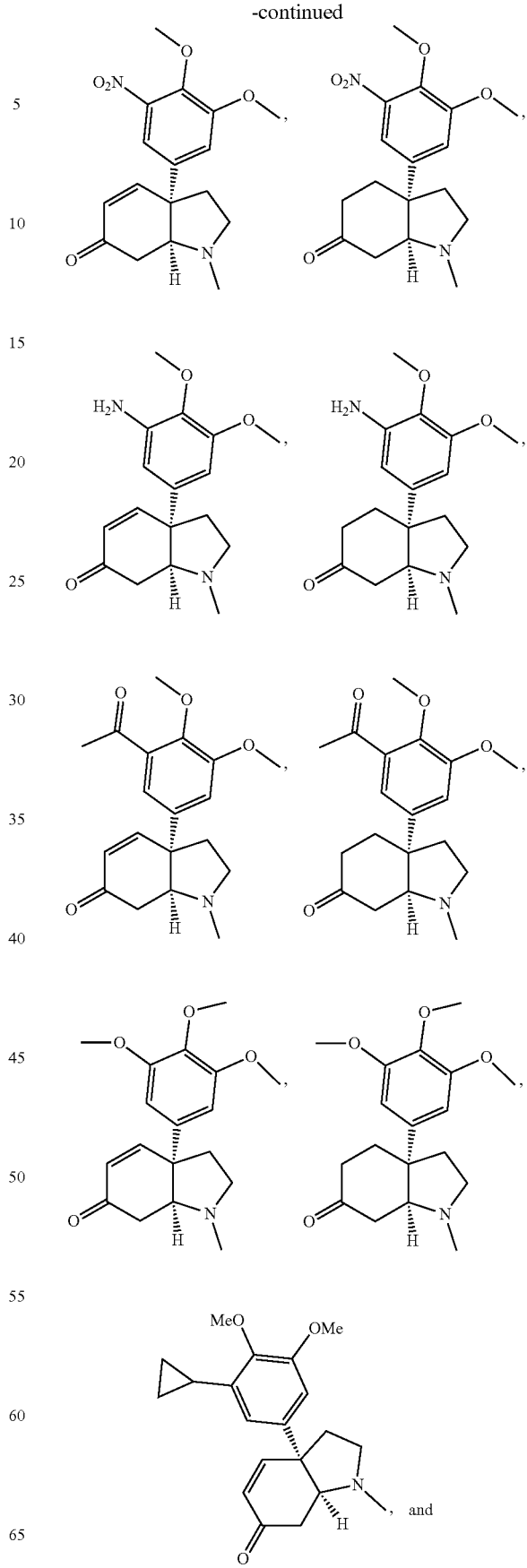

-continued

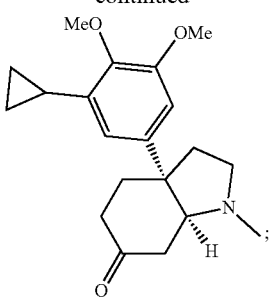

or a pharmaceutically acceptable salt thereof.

In certain embodiments, the compound is selected from the group consisting of:

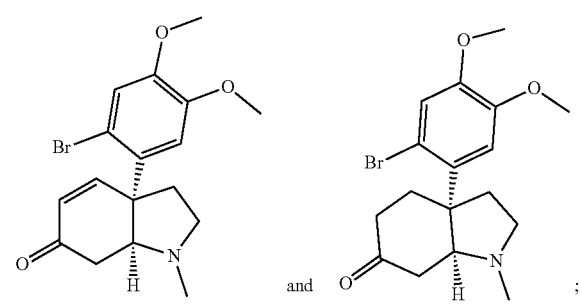 [SMILES: COc1cc(Br)c([C@@]23C=CC(=O)C[C@@H]2N(C)CC3)cc1OC ; COc1cc(Br)c([C@@]23CCC(=O)C[C@@H]2N(C)CC3)cc1OC]

or a pharmaceutically acceptable salt thereof.

In certain embodiments, the compound is selected from the group consisting of:

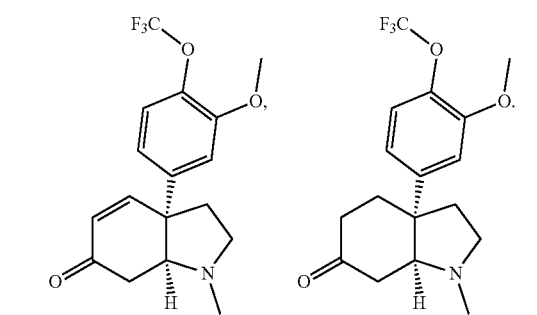

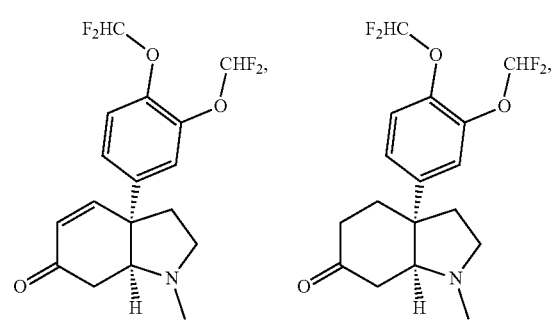

-continued

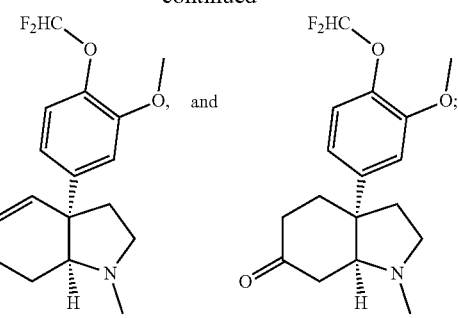

or a pharmaceutically acceptable salt thereof.

In certain embodiments, the compound is selected from the group consisting of:

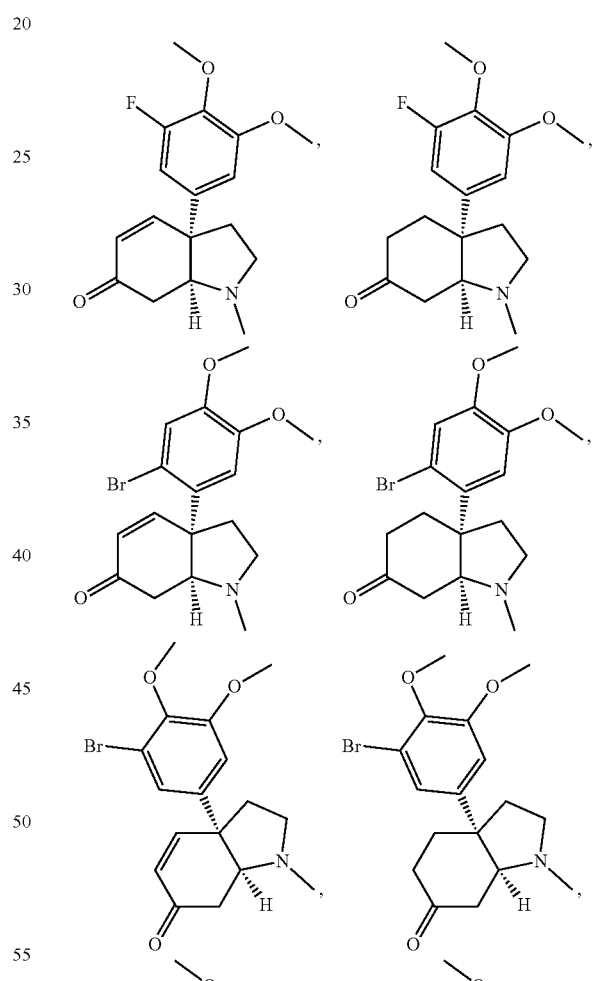

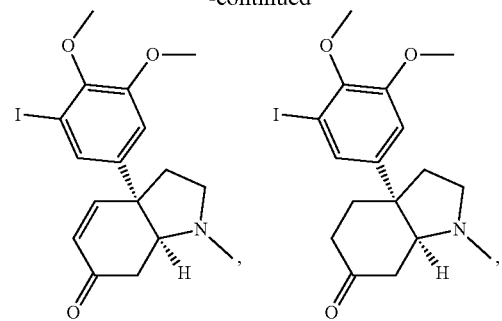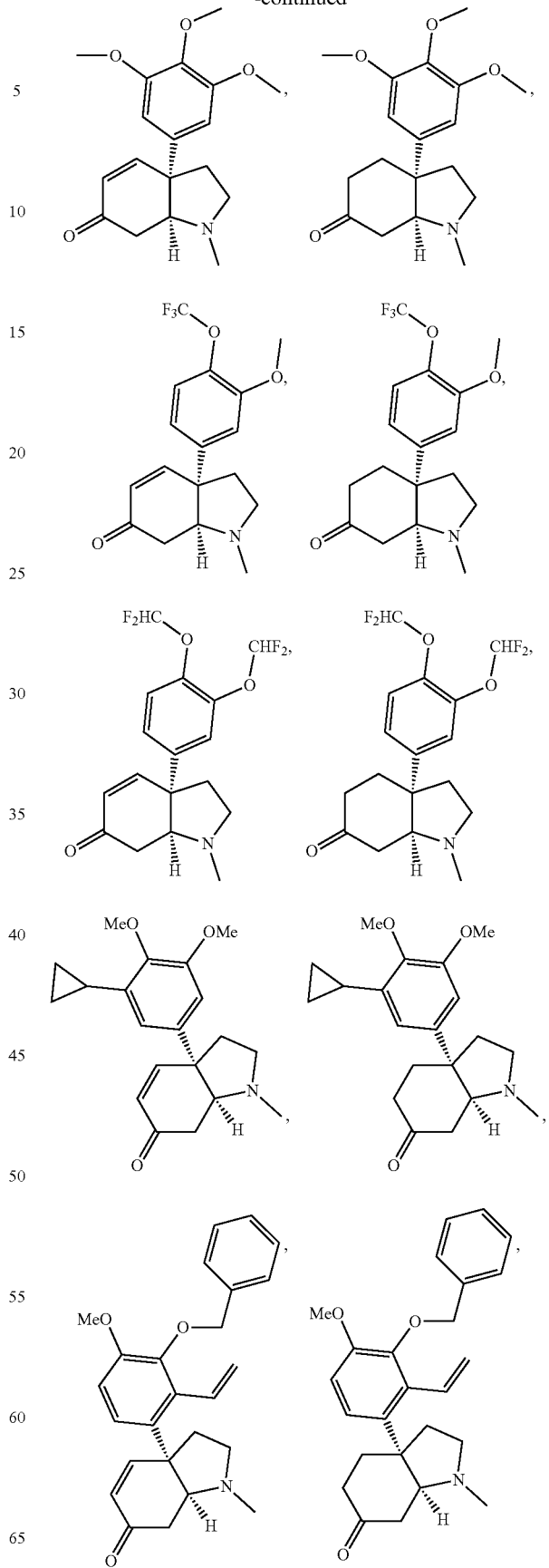

-continued
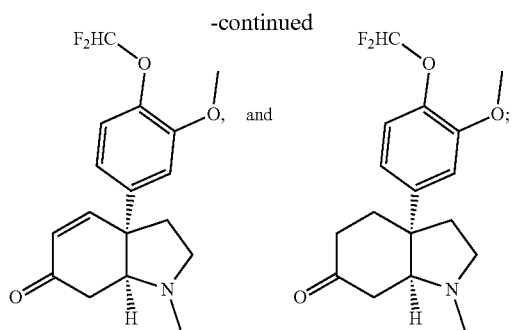 and 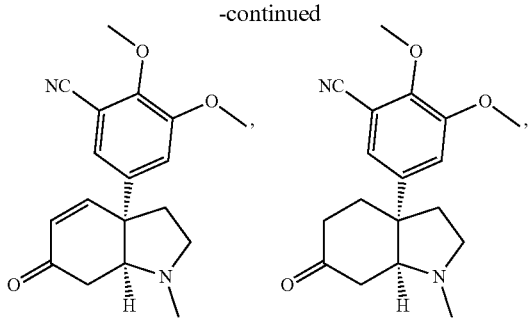
or a pharmaceutically acceptable salt thereof; and the compound has the absolute stereochemistry shown.
In certain embodiments, the compound is selected from the group consisting of:
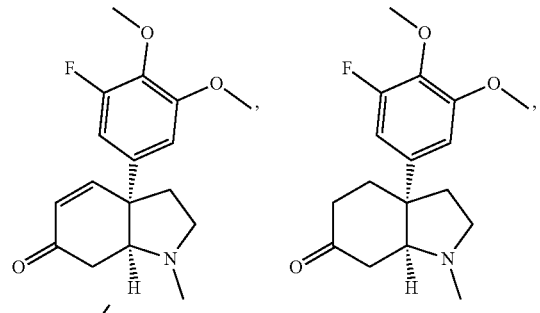
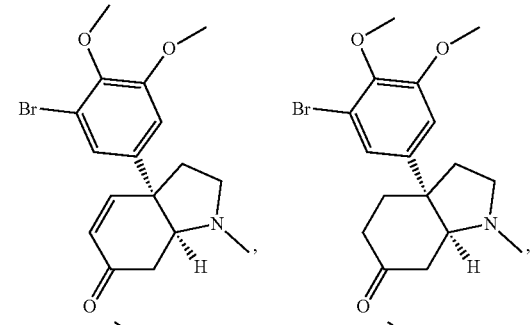
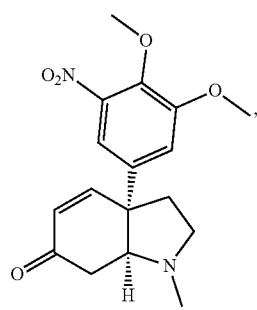 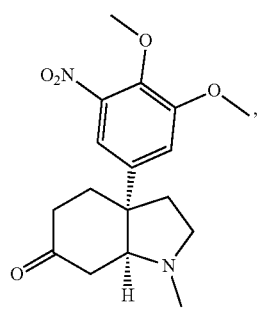
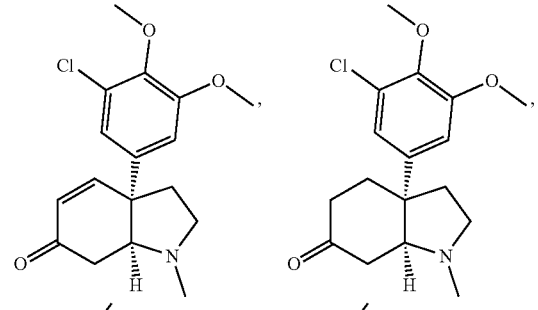 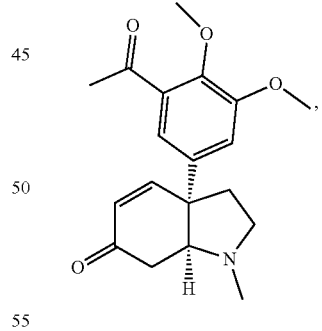
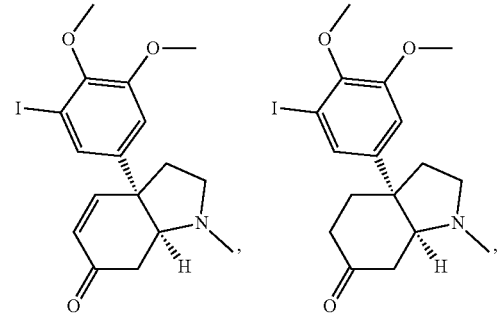 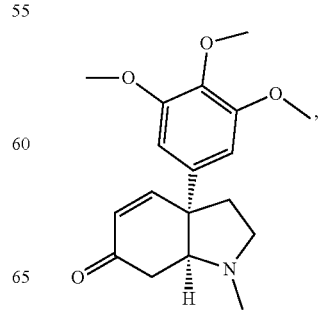

-continued

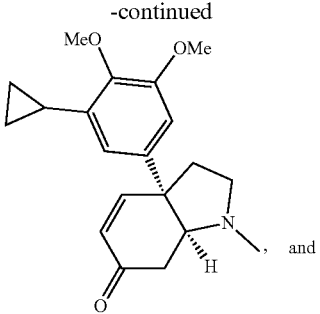, and

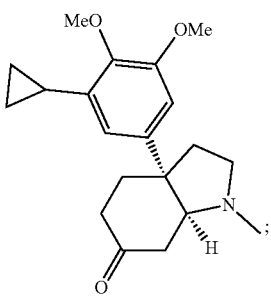 [SMILES: COc1cc([C@@]23CCC(=O)C[C@@H]2N(C)CC3)cc(C2CC2)c1OC];

or a pharmaceutically acceptable salt thereof; and the compound has the absolute stereochemistry shown.

In certain embodiments, the compound is selected from the group consisting of:

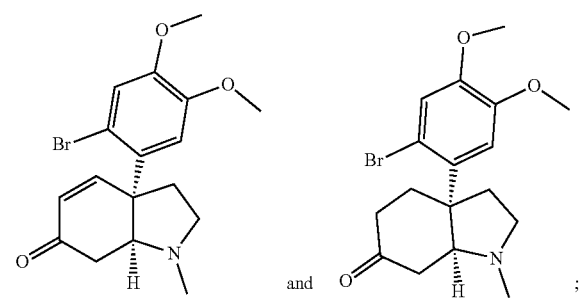 [SMILES: COc1cc(Br)c([C@@]23C=CC(=O)C[C@@H]2N(C)CC3)cc1OC ; COc1cc(Br)c([C@@]23CCC(=O)C[C@@H]2N(C)CC3)cc1OC]

or a pharmaceutically acceptable salt thereof; and the compound has the absolute stereochemistry shown.

In certain embodiments, the compound is selected from the group consisting of:

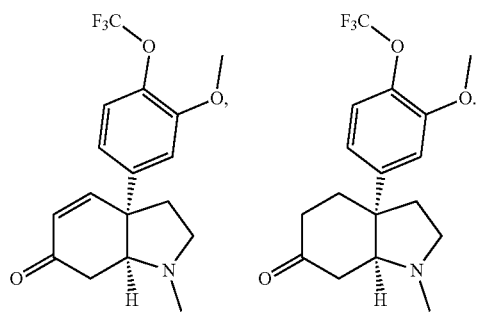

-continued

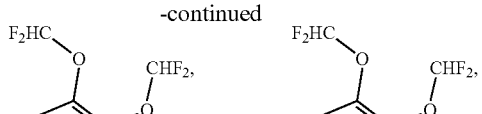

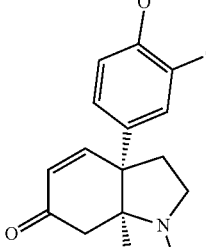

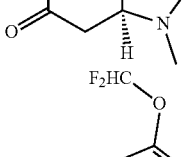, and

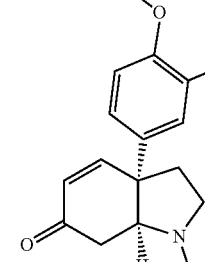

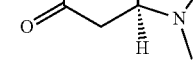;

or a pharmaceutically acceptable salt thereof; and the compound has the absolute stereochemistry shown.

In certain embodiments, the present application is directed to a pharmaceutical composition comprising an active pharmaceutical ingredient. In certain embodiments, the pharmaceutical composition comprises a compound as disclosed herein as the active pharmaceutical ingredient (API) and a pharmaceutically acceptable carrier comprising one or more excipients. In some embodiments, the pharmaceutical composition optionally further comprises an additional therapeutic compound (i.e., agent) with the pharmaceutically acceptable carrier. The pharmaceutical composition can be a medicament.

Pharmaceutically acceptable carriers include those known in the art. The choice of a pharmaceutically acceptable carrier can depend, for example, on the desired route of administration of the composition. A pharmaceutical composition (preparation) can be administered to a subject by any of a number of routes of administration including, for example, parenteral administration (e.g., intravenously, subcutaneously, or intramuscularly), oral administration (for example, tablets, and capsules); absorption through the oral mucosa (e.g., sublingually) or transdermally (for example as a patch applied to the skin) or topically (for example, as a cream, ointment or spray applied to the skin).

In some embodiments, pharmaceutical compositions comprising compounds of Formula (IA) or Formula (IB)) or pharmaceutically acceptable salts thereof can be formulated for oral administration. For example, a compound provided herein can be combined with suitable compendial excipients to form an oral unit dosage form, such as a capsule or tablet, containing a target dose of a compound of Formula (IA) or Formula (IB). The drug product can be prepared by first manufacturing the compound of Formula (IA) or Formula (IB) as an active pharmaceutical ingredient (API), followed by roller compaction/milling with intragranular excipients and blending with extra granular excipients. A Drug Product can contain the selected compound of Formula (IA) or Formula (IB) as the API and excipient components in a tablet in a desired dosage strength of Compound 1. The blended material can be compressed to form tablets and then film coated. The excipients can be selected from materials appropriate for inclusion in a pharmaceutical composition for an intended purpose and route of delivery including providing a desired manufacturing and stability properties and/or desired in vivo characteristics or other properties to the pharmaceutical composition. In some embodiments, the pharmaceutical composition can include a compound of Formula (IA) or Formula (IB) as the API in combination with a filler (e.g., a form of microcrystalline cellulose), a dry binder or disintegrant (e.g., a cross-linked polymer), a glidant (e.g., colloidal silicon dioxide) and/or a lubricant (e.g., magnesium stearate). In some embodiments, the pharmaceutical composition can comprise a material such as an extended release or disintegrant involved in carrying or transporting the API pharmaceutical agent from one organ, or portion of the body, to another organ, or portion of the body of a subject, including materials to desirable control the absorption of the API in the intestine.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

To prepare solid dosage forms for oral administration, the active ingredient is mixed with one or more pharmaceutically acceptable carriers, such as sodium citrate or dicalcium phosphate, and/or any of the following: (1) fillers or extenders, (2) binders, (3) humectants, (4) disintegrating agents, (5) solution retarding agents, (6) absorption accelerators, (7) wetting agents, (8) absorbents, (9) lubricants, (10) complexing agents, and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using suitable excipients. The pharmaceutical compositions according to the present invention may contain conventional pharmaceutical carriers and/or auxiliary agents. In some embodiments, the pharmaceutical compositions according to the present invention may contain conventional carrier agents including a binder, a lubricant and/or a glidant selected from those products and materials generally used in pharmaceutical industry for preparation of pharmaceutical compositions for an intended route of administration.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

Liquid dosage forms useful for oral administration include pharmaceutically acceptable carriers and the active ingredient provided as a solid form for reconstitution prior to administration or as a liquid (e.g., solutions, suspensions, or emulsions). In addition to the active ingredient, a liquid dosage forms may contain inert diluents commonly used in the art. For example, formulations of pharmaceutically acceptable compositions for injection can include aqueous solutions such as water or physiologically buffered saline or other solvents or vehicles suitable for the intended route of administration. In some embodiments, the pharmaceutical composition is formulated for parenteral administration.

The therapeutically effective amount of a pharmaceutical composition can be determined by human clinical trials to determine the safe and effective dose for a patient with a relevant diagnosis. It is generally understood that the effective amount of the compound may vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the pharmaceutical composition at a dose and dose interval determined to be safe and effective for the patient.

The present disclosure includes the use of pharmaceutically acceptable salts of compounds of the invention in the compositions and methods of the present invention. Pharmaceutically-acceptable salts include, for example, acid-addition salts and base-addition salts. The acid that is added to a compound to form an acid-addition salt can be an organic acid or an inorganic acid. A base that is added to a compound to form a base-addition salt can be an organic base or an inorganic base. In some embodiments, a pharmaceutically-acceptable salt is a metal salt, in some embodiments, a pharmaceutically-acceptable salt is an ammonium salt. For example, a pharmaceutically acceptable acid addition salt can exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

In some embodiments, a compound of Formula (IB) can provide additional beneficial properties. For example, the compounds described herein may provide beneficial therapeutic properties while minimizing emesis. For example, compounds of Formula (IB) may have improved selectivity for inhibiting PDE4 and the specific variants thereof. In some embodiments, the compounds of Formula (IB) described herein inhibit specific variants of PDE4. Preferred compounds, depending on indication, exhibit one of three major profiles: (A)<50 nM IC50 at SERT with greater than 10-fold selectivity over PDE4; (B)<50 nM IC50 at PDE4 with greater than 10-fold selectivity over SERT; or (C)<50 nM IC50 at SERT and PDE4. In certain instances, preferred compounds will have PDE4 isoform selectivity with a 10-fold bias for one or more isoforms over the others in-class. For example, PDE4b selective and PDE4d selective compounds are desirable. Furthermore, compounds that have a high brain exposure with brain:plasma ratios (expressed as Kp) >0.3 and ideally >0.7 are most desirable. In some embodiments, a compound of Formula (IA) or Formula (IB) can inhibit SERT with an IC$_{50}$ of less than about 1 micromolar in the assay of Example A1.

In some embodiments, compounds of Formula (IB) can be selected to provide beneficial properties. For example, compounds can have improved the selectivity for inhibiting PDE4 compared to SERT. In some embodiments, compounds of Formula (IB) disclosed herein are at least 2×, at least 3×, at least 5×, or at least 10× selective for PDE4 over SERT.

ADDITIONAL EMBODIMENTS

1. A compound of Formula (IA) or (IB):

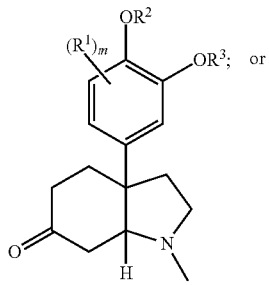

(IA)

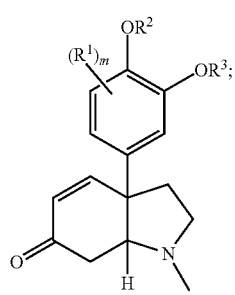

(IB)

or a pharmaceutically acceptable salt thereof; wherein

R$^1$ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;

R$^2$ is methyl or halomethyl;

R$^3$ is methyl, halomethyl, or benzyl;

m is 0, 1, 2, or 3; and each R$^a$ and R$^b$ is independently H, alkyl, alkenyl, cycloalkyl, heterocycloalkyl, aryl, or heteroaryl; or if an instance of R$^1$ is —NR$^a$R$^b$, then R$^a$ and R$^b$ may combine with the nitrogen atom to which they are attached to form heterocycloalkyl or heteroaryl;

provided the compound is not:

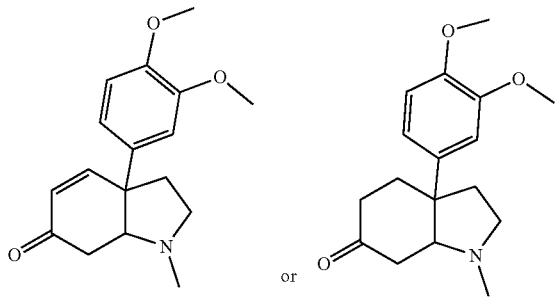

2. The compound of embodiment 1, wherein the compound is of Formula (IA-1) or (IB-1):

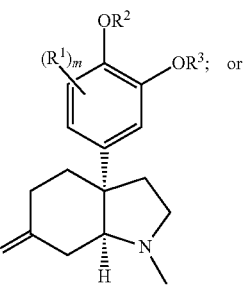

(IA-1)

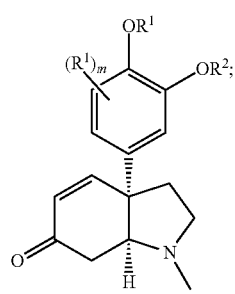

(IB-1)

or a pharmaceutically acceptable salt thereof; wherein

R$^1$ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;

R$^2$ is methyl or halomethyl;

R$^3$ is methyl, halomethyl, or benzyl;

m is 0, 1, 2, or 3;

each R$^a$ and R$^b$ is independently H, alkyl, alkenyl, cycloalkyl, heterocycloalkyl, aryl, or heteroaryl; or if an instance of R$^1$ is —NR$^a$R$^b$, then R$^a$ and R$^b$ may combine with the nitrogen atom to which they are attached to form heterocycloalkyl or heteroaryl; and the compounds of Formula (IA-1) and (IB-1) have the absolute stereochemistry shown, provided the compound is not:

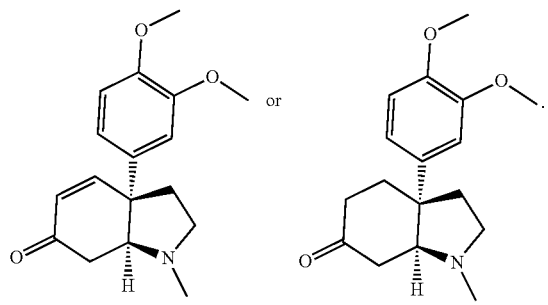 [SMILES: COc1ccc([C@@]23C=CC(=O)C[C@@H]2N(C)CC3)cc1OC ; COc1ccc([C@@]23CCC(=O)C[C@@H]2N(C)CC3)cc1OC]

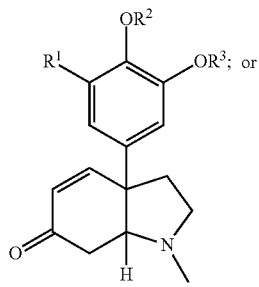

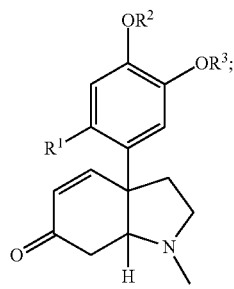

3. The compound of embodiment 1 or 2, wherein the compound is of Formula (IA) or Formula (IA-1) or a pharmaceutically acceptable salt thereof.

4. The compound of embodiment 1 or 2, wherein the compound is of Formula (IB) or Formula (IB-1) or a pharmaceutically acceptable salt thereof.

5. The compound of any one of embodiments 1-4, wherein m is 1, 2, or 3.

6. The compound of any one of embodiments 1-4, wherein m is 1 or 2.

7. The compound of any one of embodiments 1-4, wherein m is 1.

8. The compound of embodiment 1, wherein the compound is of Formula (IA-2), (IA-3), (IB-2), or (IB-3):

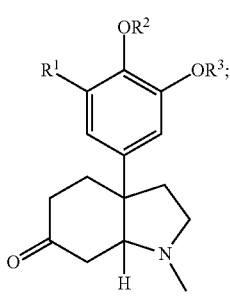

or a pharmaceutically acceptable salt thereof; wherein
$R^1$ is halo, haloalkyl, alkyl, alkenyl, alkynyl, cycloalkyl, cycloalkenyl, heterocycloalkyl, aryl, heteroaryl, —$OR^a$, —$NR^aR^b$, —CHO, —C(O)$R^a$, —CO$_2R^a$, —C(O)NR$^a$R$^b$, —CN, nitro, or —P(O)OR$^a$OR$^b$;
$R^2$ is methyl or halomethyl;
$R^3$ is methyl, halomethyl, or benzyl; and
each $R^a$ and $R^b$ is independently H, alkyl, alkenyl, cycloalkyl, heterocycloalkyl, aryl, or heteroaryl; or if an instance of $R^1$ is —NR$^a$R$^b$, then $R^a$ and $R^b$ may combine with the nitrogen atom to which they are attached to form heterocycloalkyl or heteroaryl.

9. The compound of embodiment 8, wherein the compound is of Formula (IA-2) or a pharmaceutically acceptable salt thereof.

10. The compound of embodiment 8, wherein the compound is of Formula (IA-3) or a pharmaceutically acceptable salt thereof.

11. The compound of embodiment 8, wherein the compound is of Formula (IB-2) or a pharmaceutically acceptable salt thereof).

12. The compound of embodiment 8, wherein the compound is of Formula (IB-3) or a pharmaceutically acceptable salt thereof.

13. The compound of embodiment 1, wherein the compound is of Formula (IA-4), (IA-5), (IB-4), or (IB-5):

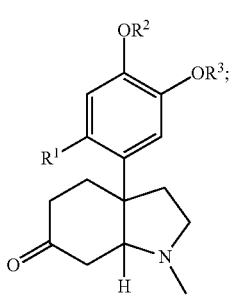

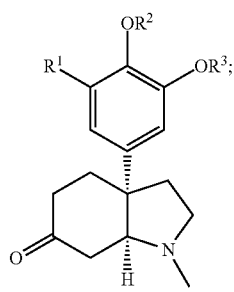

-continued

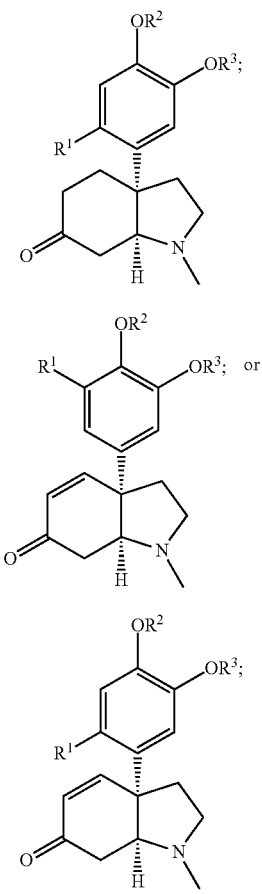

(IA-5)

(IB-4)

(IB-5)

or a pharmaceutically acceptable salt thereof; wherein

R¹ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;

R² is methyl or halomethyl;

R³ is methyl, halomethyl, or benzyl;

each R$^a$ and R$^b$ is independently H, alkyl, alkenyl, cycloalkyl, heterocycloalkyl, aryl, or heteroaryl; or if an instance of R¹ is —NR$^a$R$^b$, then R$^a$ and R$^b$ may combine with the nitrogen atom to which they are attached to form heterocycloalkyl or heteroaryl; and the compounds of Formula (IA-4), (IA-5), (IB-4), and (IB-5) have the absolute stereochemistry shown.

14. The compound of embodiment 13, wherein the compound is of Formula (IA-4) or a pharmaceutically acceptable salt thereof.

15. The compound of embodiment 13, wherein the compound is of Formula (IA-5) or a pharmaceutically acceptable salt thereof.

16. The compound of embodiment 13, wherein the compound is of Formula (IB-4) or a pharmaceutically acceptable salt thereof.

17. The compound of embodiment 13, wherein the compound is of Formula (IB-5) or a pharmaceutically acceptable salt thereof.

18. The compound of embodiment 1, wherein the compound is of Formula (IA-6), (IA-7), (IB-6), or (IB-7):

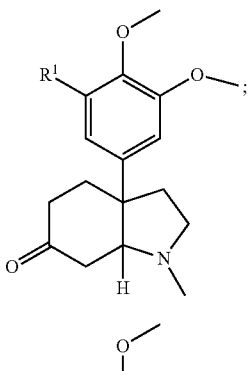

(IA-6)

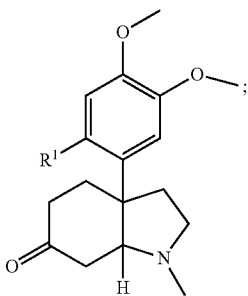

(IA-7)

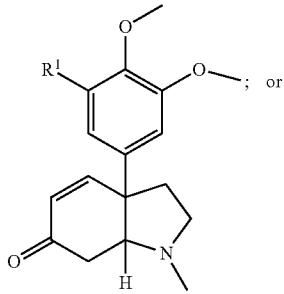

(IB-6)

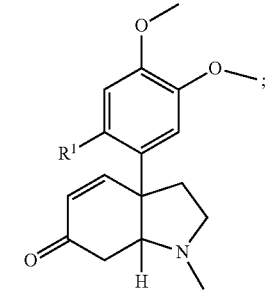

(IB-7)

or a pharmaceutically acceptable salt thereof; wherein

R¹ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$; and each R$^a$ and R$^b$ is independently H, alkyl, alkenyl, cycloalkyl, heterocycloalkyl, aryl, or heteroaryl; or if an instance of R¹ is —NR$^a$R$^b$, then R$^a$ and R$^b$ may combine with the nitrogen atom to which they are attached to form heterocycloalkyl or heteroaryl.

19. The compound of embodiment 18, wherein the compound is of Formula (IA-6) or a pharmaceutically acceptable salt thereof.

20. The compound of embodiment 18, wherein the compound is of Formula (IA-7) or a pharmaceutically acceptable salt thereof.

21. The compound of embodiment 18, wherein the compound is of Formula (IB-6) or a pharmaceutically acceptable salt thereof.

22. The compound of embodiment 18, wherein the compound is of Formula (IB-7) or a pharmaceutically acceptable salt thereof.

23. The compound of embodiment 1, wherein the compound is of Formula (IA-8), (IA-9), (IB-8), or (IB-5):

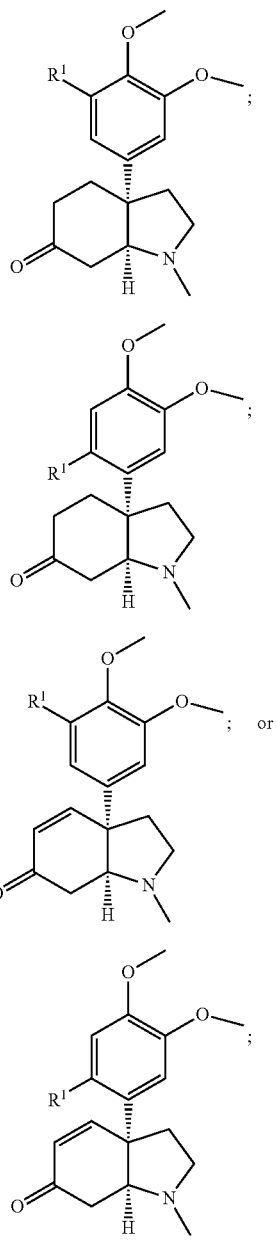

or a pharmaceutically acceptable salt thereof; wherein
R¹ is halo, haloalkyl, alkyl, alkenyl, alkynyl, cycloalkyl, cycloalkenyl, heterocycloalkyl, aryl, heteroaryl, —OR$^a$, —NR$^a$R$^b$, —CHO, —C(O)R$^a$, —CO$_2$R$^a$, —C(O)NR$^a$R$^b$, —CN, nitro, or —P(O)OR$^a$OR$^b$;
each R$^a$ and R$^b$ is independently H, alkyl, alkenyl, cycloalkyl, heterocycloalkyl, aryl, or heteroaryl; or if an instance of R¹ is —NR$^a$R$^b$, then R$^a$ and R$^b$ may combine with the nitrogen atom to which they are attached to form heterocycloalkyl or heteroaryl; and
the compounds of Formula (IA-8), (IA-9), (IB-8), and (IB-9) have the absolute stereochemistry shown.

24. The compound of embodiment 23, wherein the compound is of Formula (IA-8) or a pharmaceutically acceptable salt thereof.

25. The compound of embodiment 23, wherein the compound is of Formula (IA-9) or a pharmaceutically acceptable salt thereof.

26. The compound of embodiment 23, wherein the compound is of Formula (IB-8) or a pharmaceutically acceptable salt thereof.

27. The compound of embodiment 23, wherein the compound is of Formula (IB-9) or a pharmaceutically acceptable salt thereof.

28. The compound of any one of embodiments 1-27, wherein R¹ is halo, haloalkyl, alkyl, cycloalkyl, cycloalkenyl, heterocycloalkyl, aryl, heteroaryl, —OR$^a$, —NRaR¹, —CHO, C(O)R$^a$, —CN, or nitro.

29. The compound of any one of embodiments 1-28, wherein R¹ is halo, haloalkyl, alkyl, cycloalkyl, heterocycloalkyl, —OR$^a$, —NRaR¹, —CHO, C(O)R$^a$, —CN, or nitro.

30. The compound of any one of embodiments 1-29, wherein R¹ is alkyl.

31. The compound of any one of embodiments 1-29, wherein R¹ is haloalkyl.

32. The compound of any one of embodiments 1-29, wherein R¹ is halo, cycloalkyl, —OR$^a$, —NR$^a$R$^b$, C(O)R$^a$, —CN, or nitro.

33. The compound of any one of embodiments 1-29, wherein R¹ is halo, cycloalkyl, alkoxy, —NH$_2$, C(O)alkyl, —CN, or nitro.

34. The compound of embodiment 33, wherein R¹ is —C(O)alkyl.

35. The compound of embodiment 33, wherein R¹ is alkoxy.

36. The compound of embodiment 33, wherein R¹ is cycloalkyl.

37. The compound of any one of embodiments 1-29, wherein R¹ is halo, cyclopropyl, —OCH$_3$, —NH$_2$, C(O)CH$_3$, —CN, or nitro.

38. The compound of embodiment 37, wherein R¹ is halo.

39. The compound of embodiment 37, wherein R¹ is —CN.

40. The compound of embodiment 37, wherein R¹ is nitro.

41. The compound of embodiment 37, wherein R¹ is —NH$_2$.

42. The compound of embodiment 37, wherein R¹ is —C(O)CH$_3$.

43. The compound of embodiment 37, wherein R¹ is methoxy.

44. The compound of any one of embodiments 1-4, wherein m is 0.

45. The compound of any one of embodiments 1-44, wherein R² is methyl.

46. The compound of any one of embodiments 1-44, wherein R² is halomethyl.

47. The compound of any one of embodiments 1-44, wherein R² is halomethyl substituted with at least one fluoro.

48. The compound of any one of embodiments 1-44, wherein R² is CHF$_2$ or CF$_3$.

49. The compound of any one of embodiments 1-44 or 46-48, wherein R³ is methyl.

50. The compound of any one of embodiments 1-48, wherein R³ is halomethyl.

51. The compound of any one of embodiments 1-48, wherein R³ is halomethyl substituted with at least one fluoro.
52. The compound of any one of embodiments 1-48, wherein R³ is CHF₂ or CF₃.
53. The compound of embodiment 1, selected from the group consisting of:
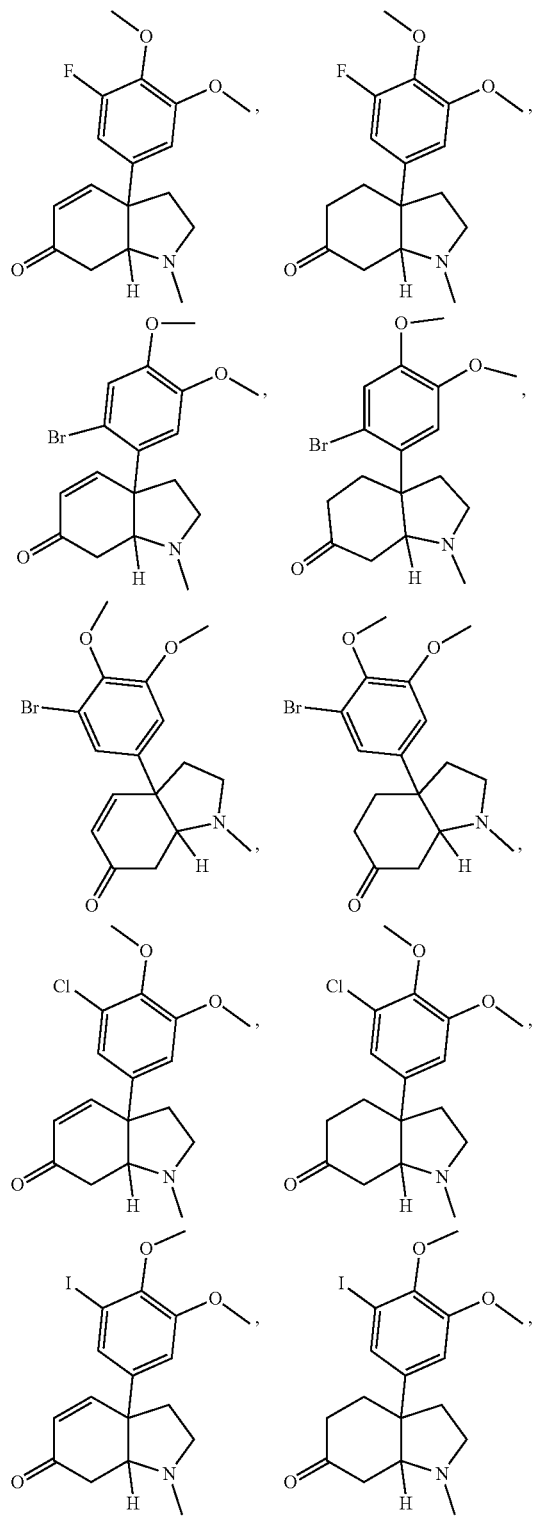
-continued
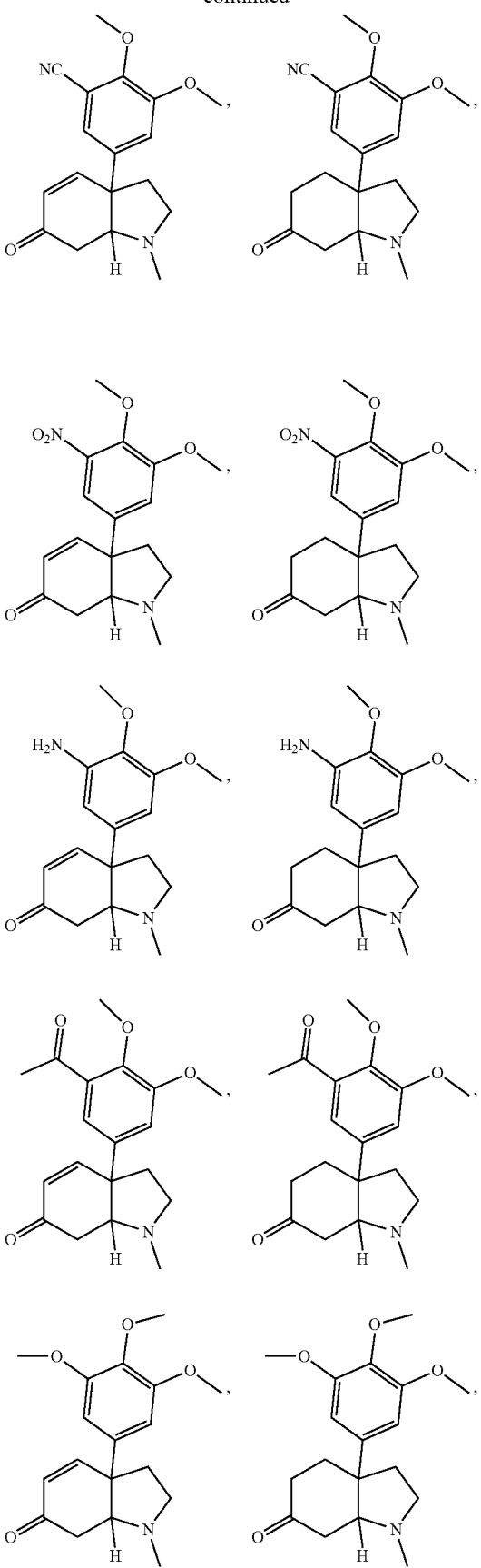

49
-continued
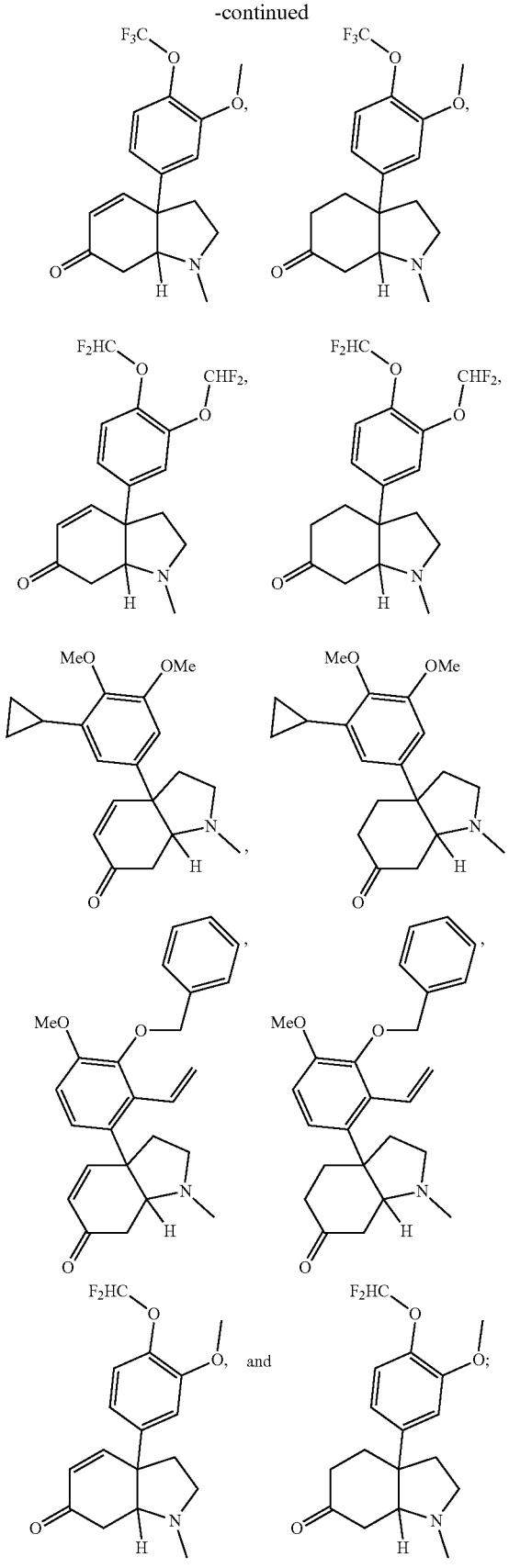
or a pharmaceutically acceptable salt thereof.
50
54. The compound of embodiment 1, selected from the group consisting of:
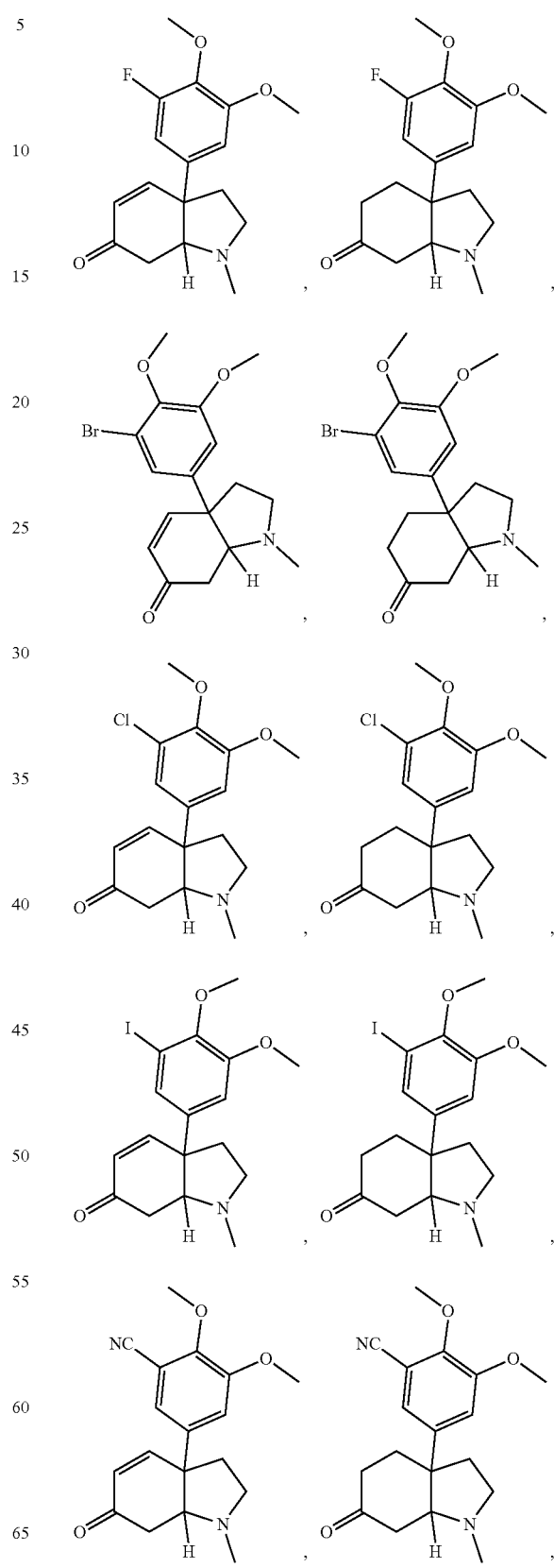

-continued
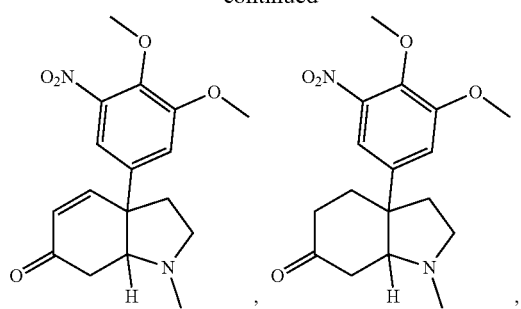
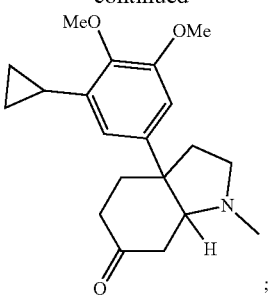
or a pharmaceutically acceptable salt thereof.
55. The compound of embodiment 1, selected from the group consisting of:
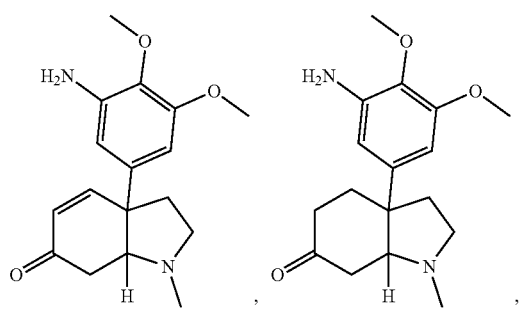
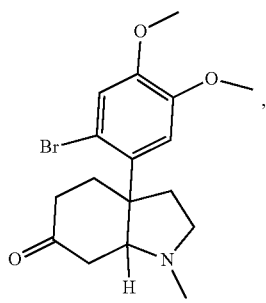
or a pharmaceutically acceptable salt thereof.
56. The compound of embodiment 1, selected from the group consisting of:
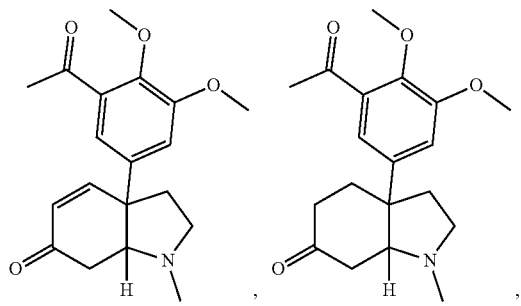
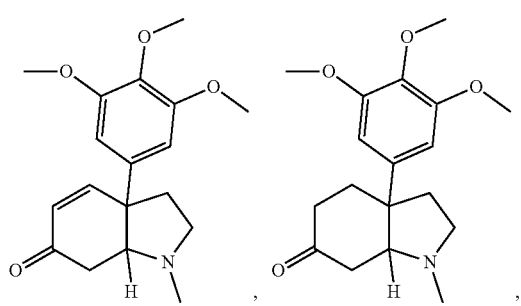
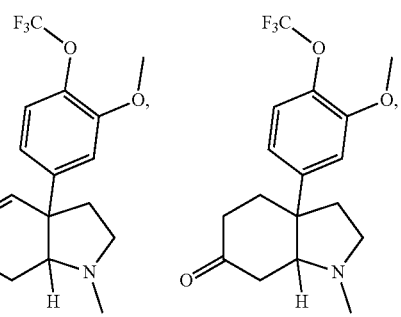
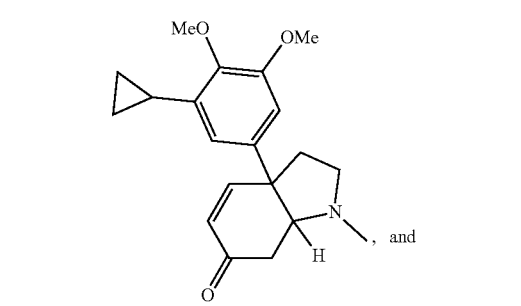
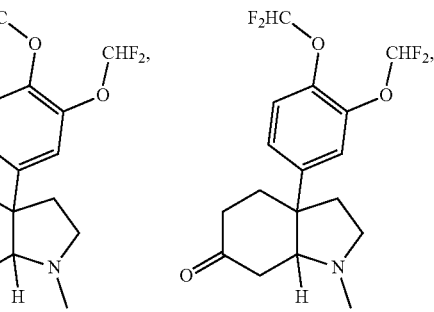

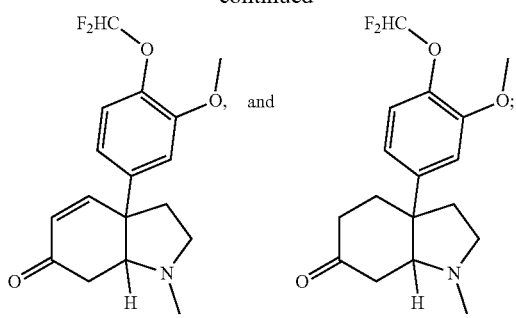
or a pharmaceutically acceptable salt thereof.
57. The compound of embodiment 1, selected from the group consisting of:
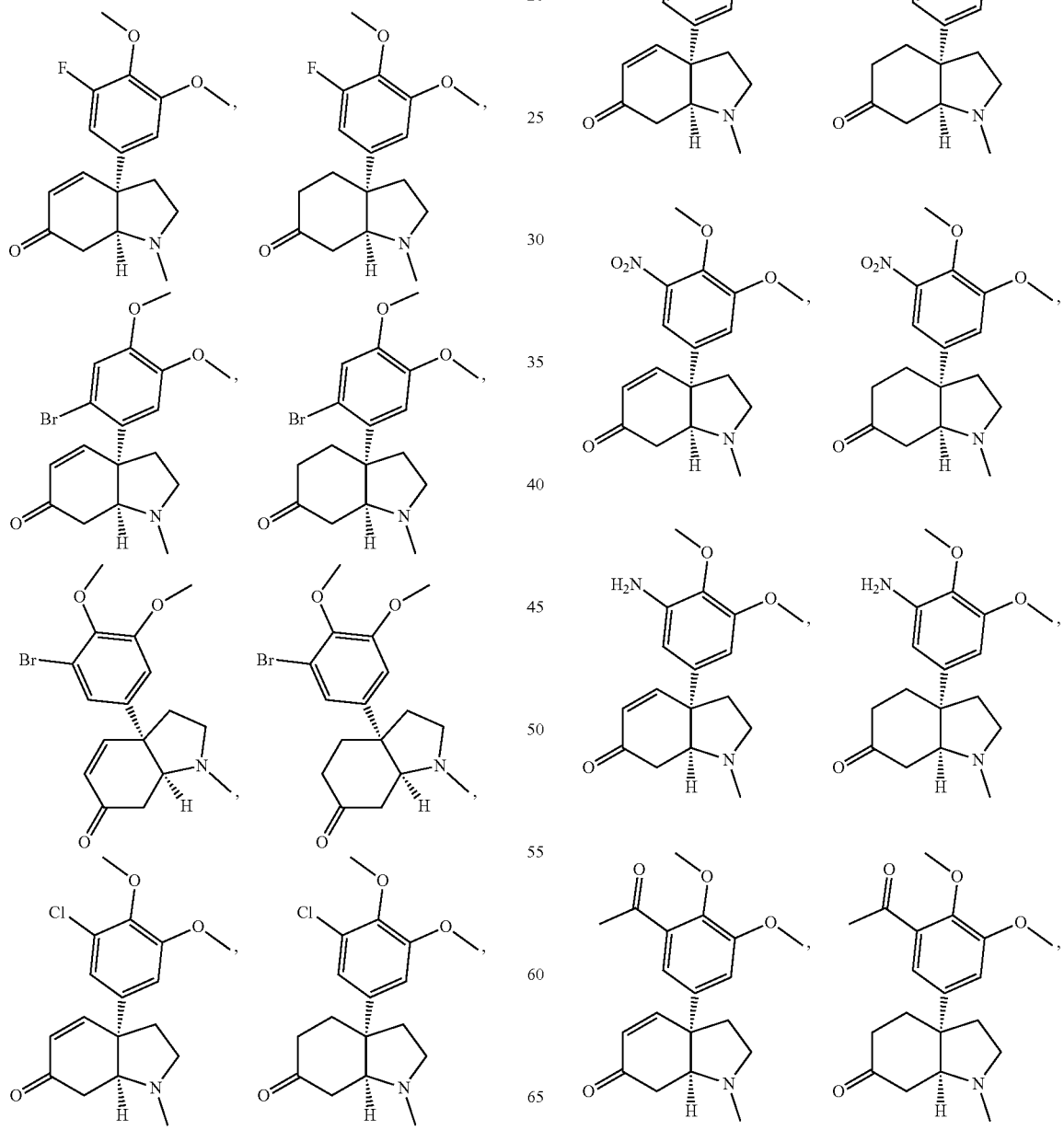

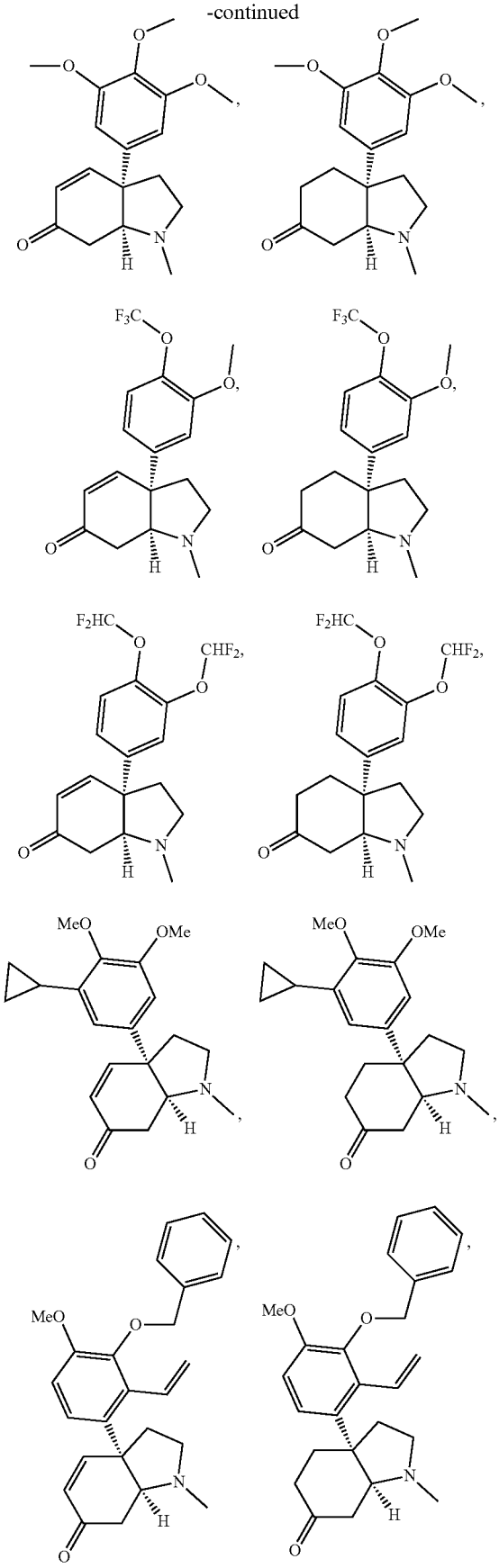
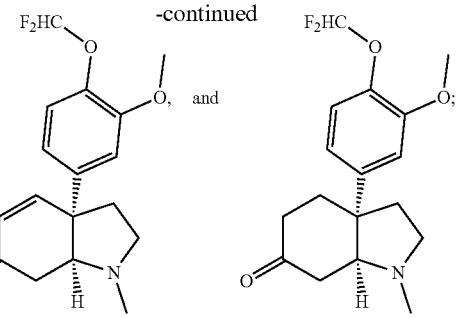
or a pharmaceutically acceptable salt thereof.
58. The compound of embodiment 1, selected from the group consisting of:
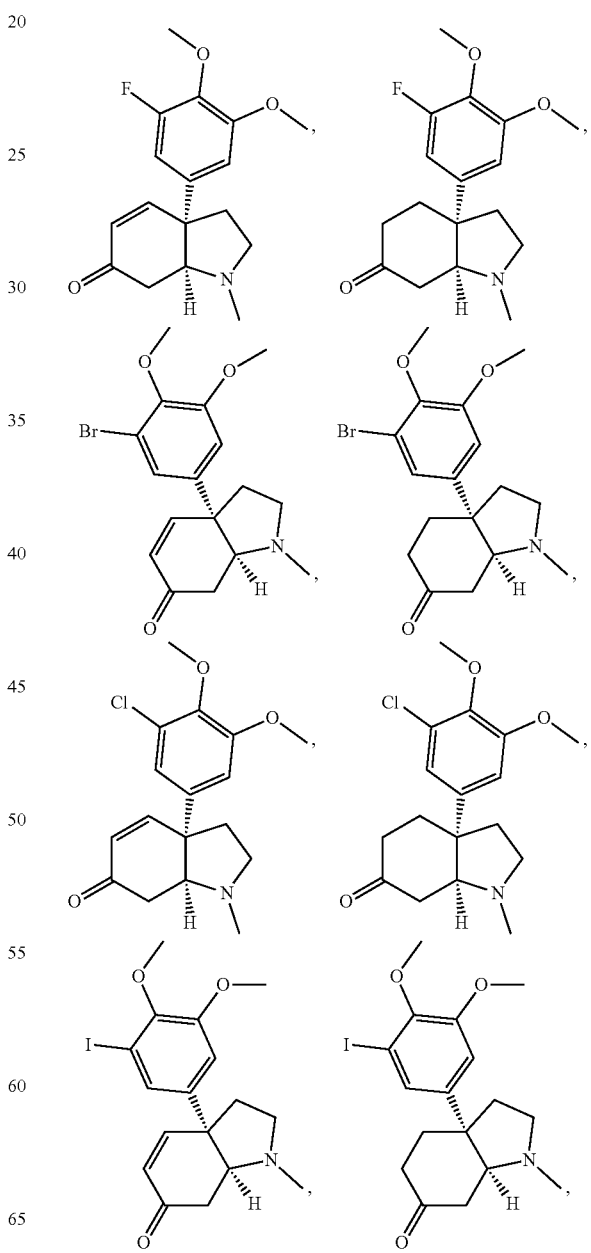

-continued
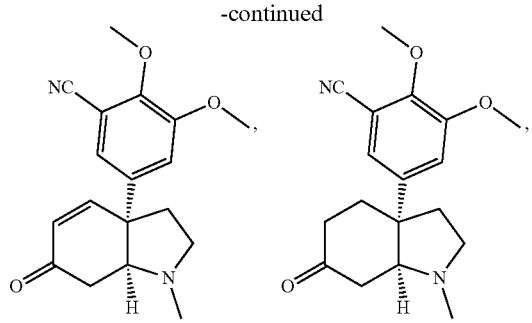
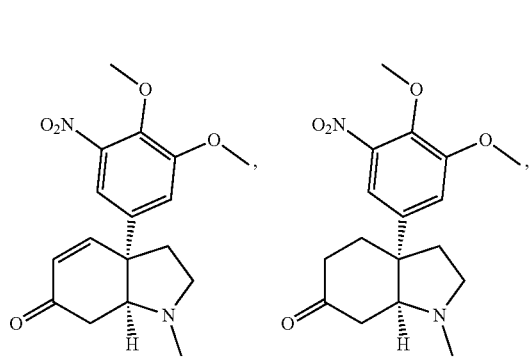
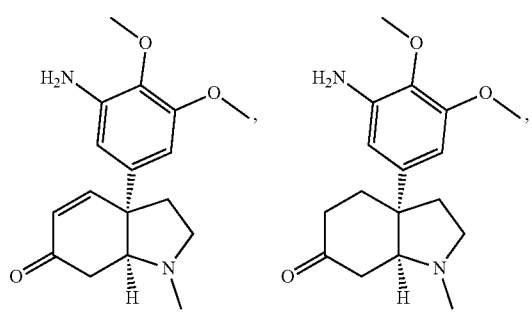
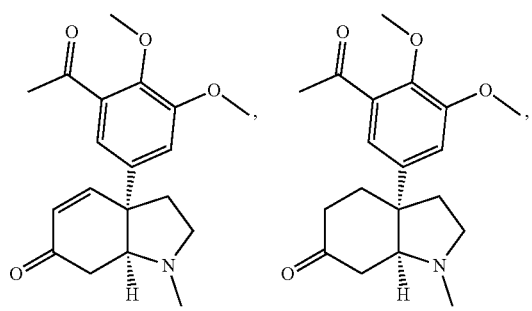
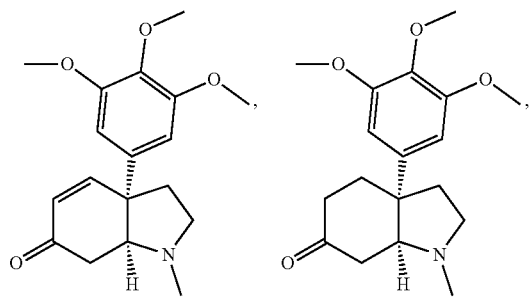
-continued
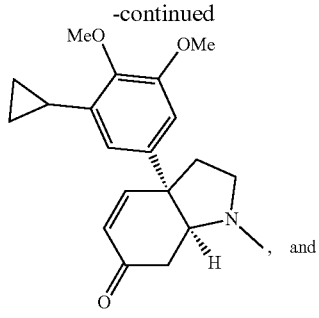, and
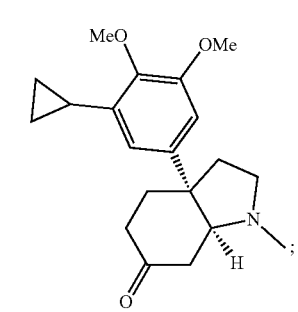 [SMILES: COc1cc([C@@]23CCC(=O)C[C@@H]2N(C)CC3)cc(C2CC2)c1OC];
or a pharmaceutically acceptable salt thereof.
59. The compound of embodiment 1, selected from the group consisting of:
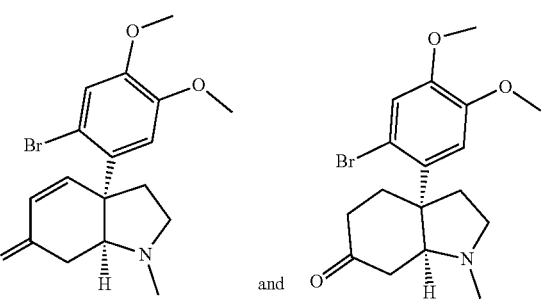
or a pharmaceutically acceptable salt thereof.
60. The compound of embodiment 1, selected from the group consisting of:
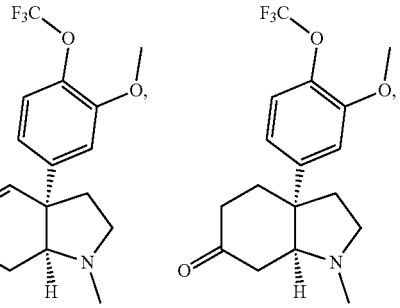

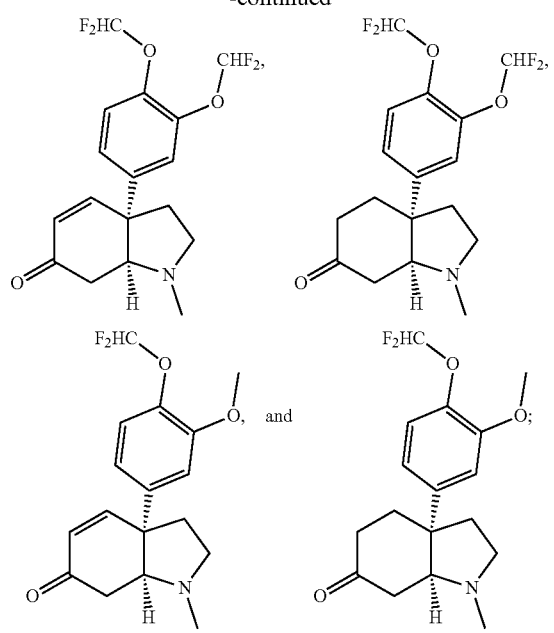
or a pharmaceutically acceptable salt thereof.
61. The compound of embodiment 1, selected from the group consisting of:
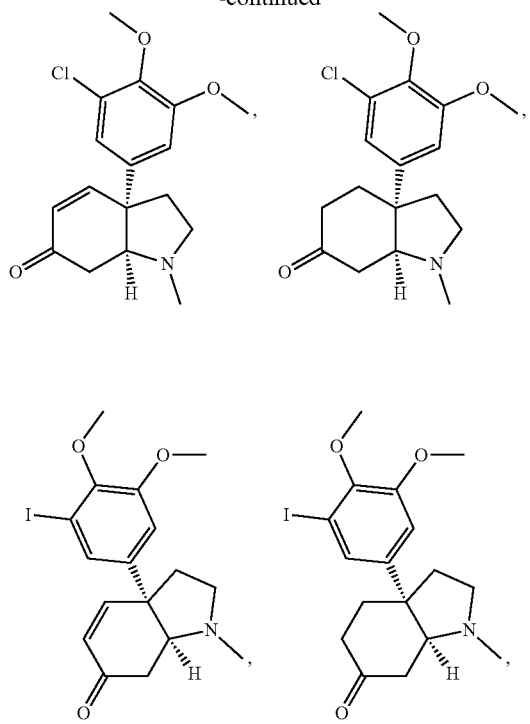

-continued
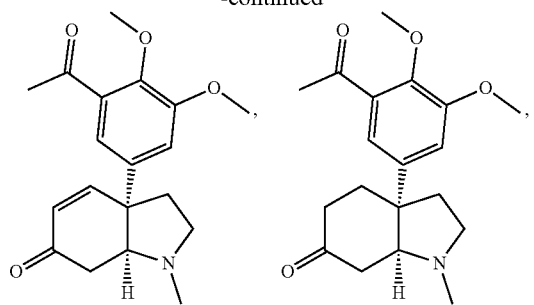
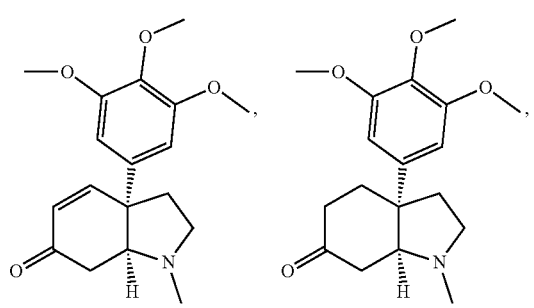
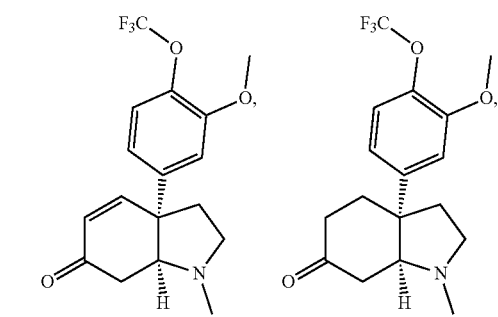
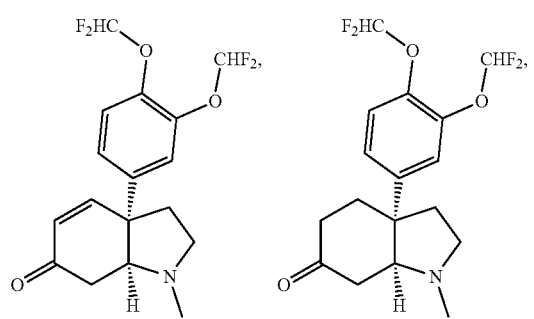
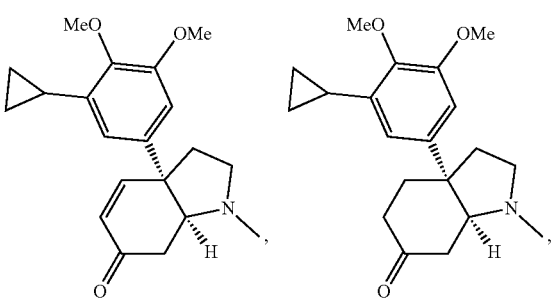
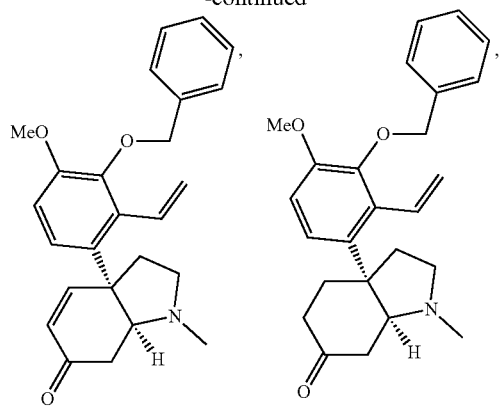
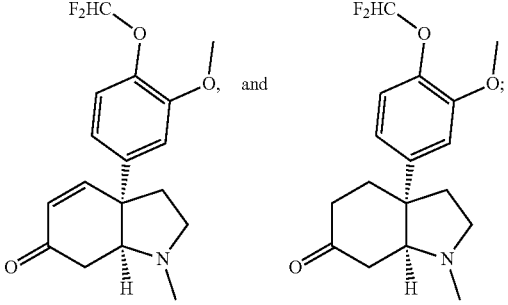
or a pharmaceutically acceptable salt thereof; wherein the compound has the absolute stereochemistry shown.
62. The compound of embodiment 1, selected from the group consisting of:
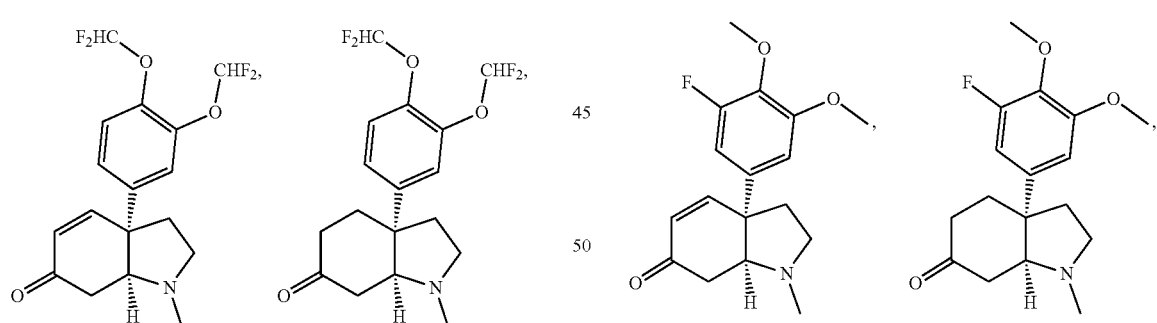
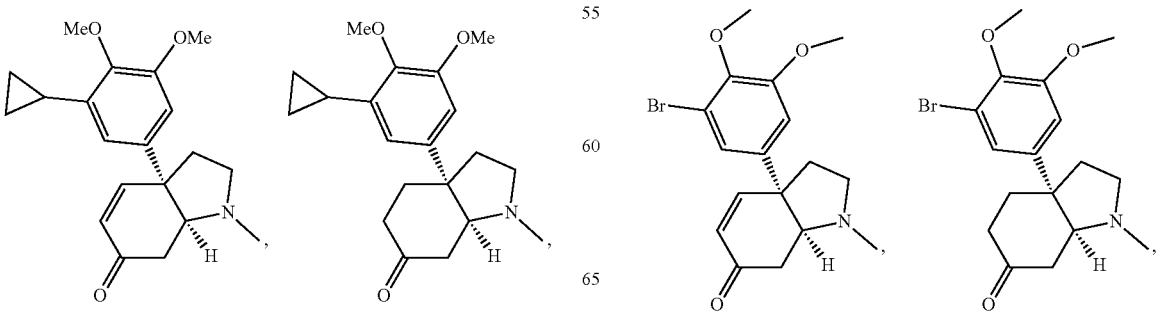

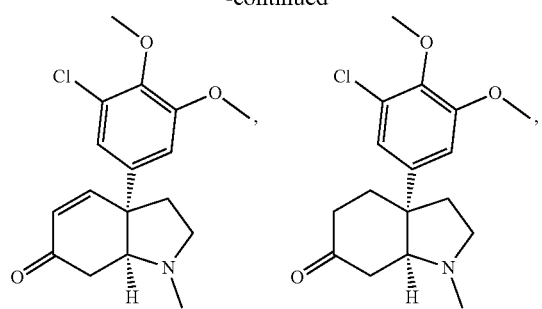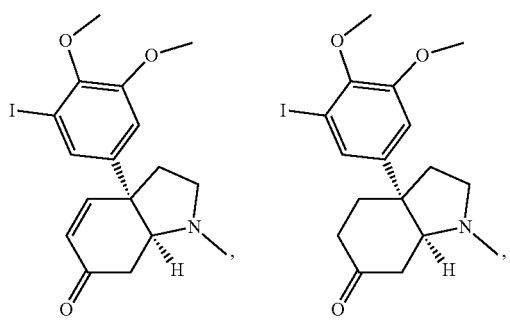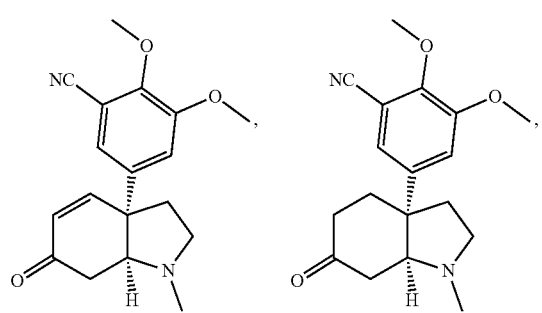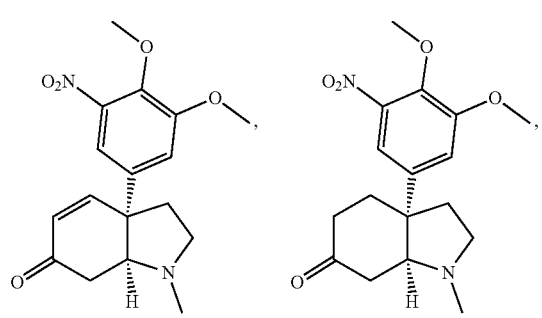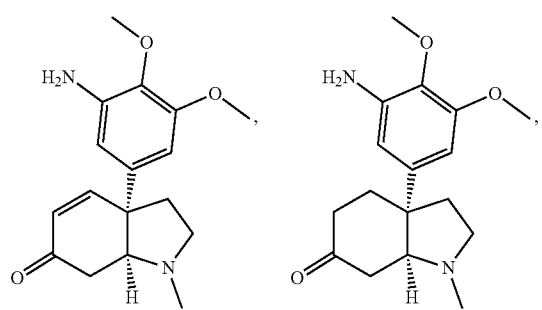
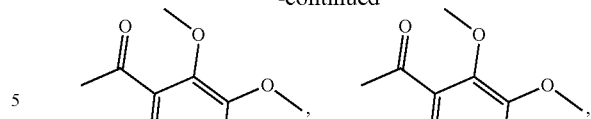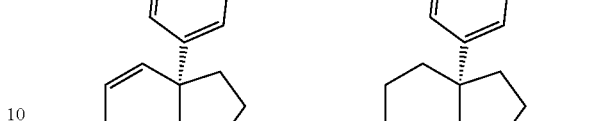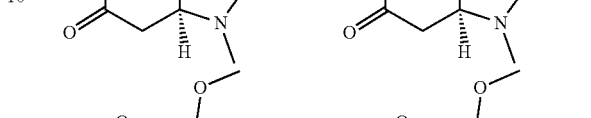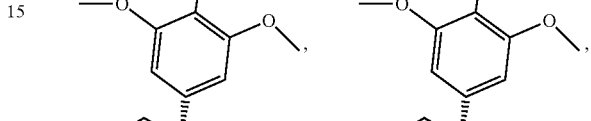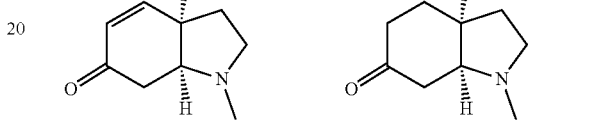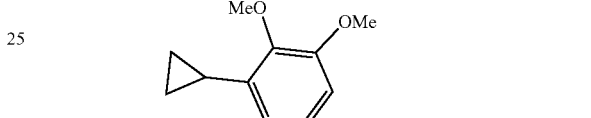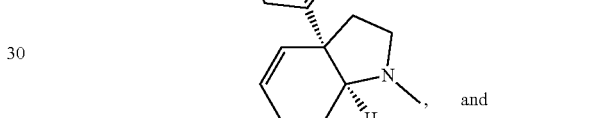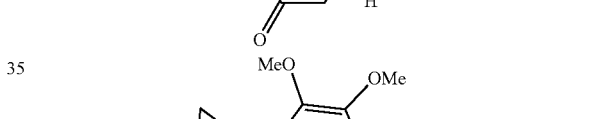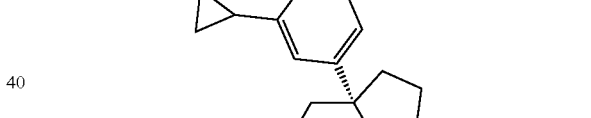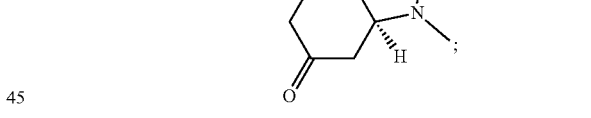
or a pharmaceutically acceptable salt thereof; wherein the compound has the absolute stereochemistry shown.
63. The compound of embodiment 1, selected from the group consisting of:
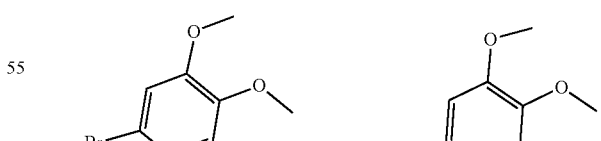
or a pharmaceutically acceptable salt thereof; wherein the compound has the absolute stereochemistry shown.

64. The compound of embodiment 1, selected from the group consisting of:

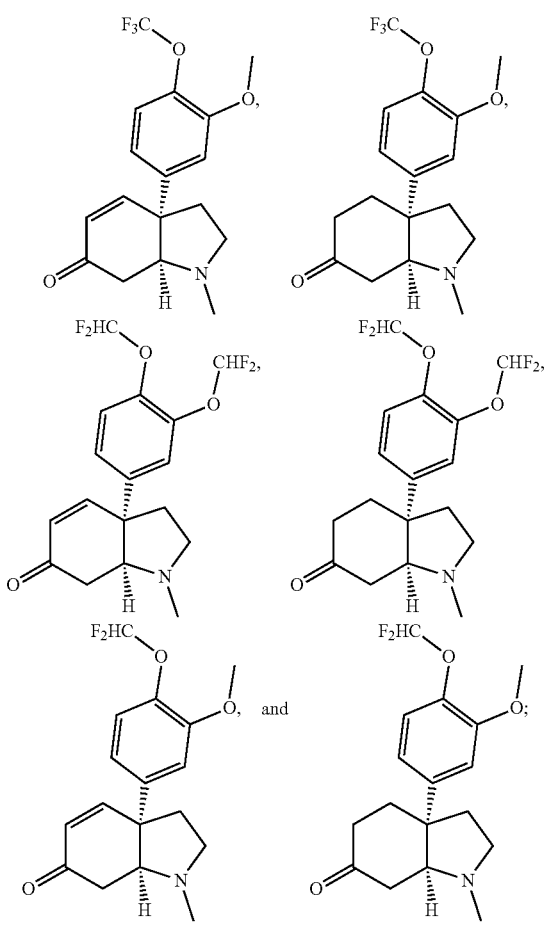

or a pharmaceutically acceptable salt thereof; wherein the compound has the absolute stereochemistry shown.

65. A pharmaceutical composition, comprising a compound of any one of embodiments 1-64 or a pharmaceutically acceptable salt thereof; and a pharmaceutically acceptable excipient.

66. A method of treating a mental health disorder, comprising administering to a mammal in need thereof an effective amount of a compound according to any one of embodiments 1-64 or a pharmaceutically acceptable salt thereof.

67. The method of embodiment 66, wherein the mental health disorder is anxiety, stress, or depression.

68. The method of embodiment 66, wherein the mental health disorder is anxiety.

69. The method of embodiment 66, wherein the mental health disorder is stress.

70. The method of embodiment 66, wherein the mental health disorder is depression.

71. The method of any one of embodiments 66-70, wherein the mammal is a human.

72. A method of treating an inflammatory condition, comprising administering to a mammal in need thereof an effective amount of a compound according to any one of embodiments 1-64 or a pharmaceutically acceptable salt thereof.

73. The method of embodiment 72, wherein the inflammatory condition is chronic obstructive pulmonary disease (COPD), asthma, or rheumatoid arthritis.

74. The method of embodiment 72, wherein the inflammatory condition is COPD.

75. The method of embodiment 72, wherein the inflammatory condition is asthma.

76. The method of embodiment 72, wherein the inflammatory condition is rheumatoid arthritis.

77. The method of any one of embodiments 72-76, wherein the mammal is a human.

78. The compound of any one of embodiments 1-17, wherein $R^3$ is methyl or halomethyl.

79. The compound of embodiment 78, wherein $R^3$ is methyl optionally substituted with one or more fluoro.

80. The compound of any one of embodiments 1-4, wherein m is 2.

81. The compound of any one of embodiments 1-4, wherein m is 3.

82. The compound of embodiment 5, wherein $R^2$ is methyl.

83. The compound of embodiment 5, wherein $R^2$ is halomethyl.

84. The compound of embodiment 5, wherein $R^2$ is halomethyl substituted with at least one fluoro.

85. The compound of embodiment 5, wherein $R^2$ is $CHF_2$ or $CF_3$.

86. The compound of embodiment 5, wherein $R^3$ is methyl.

87. The compound of embodiment 5, wherein $R^3$ is halomethyl.

88. The compound of embodiment 5, wherein $R^3$ is halomethyl substituted with at least one fluoro.

89. The compound of embodiment 5, wherein $R^3$ is $CHF_2$ or $CF_3$.

90. The compound of any one of embodiments 1-44, wherein
  a. $R^2$ is methyl optionally substituted with one or more fluoro and $R^3$ is methyl optionally substituted with one or more fluoro; or
  b. $R^2$ is methyl and $R^3$ is benzyl.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS.

The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—CH$_2$—O—alkyl, —OP(O)(O-alkyl)$_2$ or —CH$_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups, $C_1$-$C_{10}$ branched-chain alkyl groups, cycloalkyl (alicyclic) groups, alkyl-substituted cycloalkyl groups, and cycloalkyl-substituted alkyl groups. Preferably, the "alkyl" group refers to $C_1$-$C_7$ straight-chain alkyl groups or $C_1$-$C_7$ branched-chain alkyl groups. Most preferably, the "alkyl" group refers to $C_1$-$C_3$ straight-chain alkyl groups or $C_1$-$C_3$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "haloalkyl" refers to an alkyl group substituted with at least one hydrogen atom on a carbon replaced by a halogen. Illustrative halogens include fluoro, chloro, bromo, and iodo. Illustrative haloalkyl groups include trifluoromethyl and 2,2,2-trifluoroethyl, etc.

The term "alkoxyalkyl" refers to an alkyl group substituted with an alkoxy group and may be represented by the general formula alkyl-O-alkyl.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS-.

The term "amide", as used herein, refers to a group

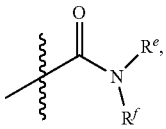

wherein $R^e$ and $R^f$ each independently represent a hydrogen or hydrocarbyl group, or $R^e$ and $R^f$ taken together with the N atom to which they are attached complete a heterocycle having from 4 to 8 atoms in the ring structure.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O) NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Preferably, the "alkoxy" group refers to $C_1$-$C_7$ straight-chain alkoxy groups or $C_1$-$C_7$ branched-chain alkoxy groups. Representative alkoxy groups include methoxy, ethoxy, propoxy, tert-butoxy and the like.

The terms "amine" and "amino" are art-recognized and refer to both unsubstituted and substituted amines and salts thereof, e.g., a moiety that can be represented by

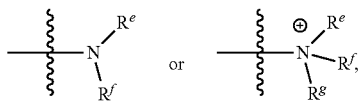

wherein $R^e$, $R^f$, and $R^g$, each independently represent a hydrogen or a hydrocarbyl group, or $R^e$ and $R^f$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring, for example a phenyl. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

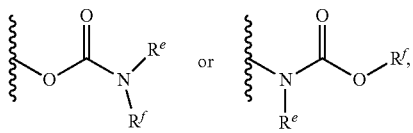

wherein $R^e$ and $R^f$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —OCO₂—.

The term "carboxy", as used herein, refers to a group represented by the formula —CO₂H.

The term "ester", as used herein, refers to a group —C(O)OR⁹ wherein R⁹ represents a hydrocarbyl group.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains six or fewer carbon atoms, preferably four or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO₃H, or a pharmaceutically acceptable salt thereof.

The term "sulfonamide" is art-recognized and refers to the group represented by the general formulae

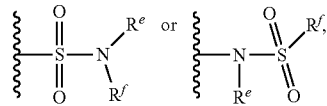

wherein $R^e$ and $R^f$ independently represents hydrogen or hydrocarbyl.

The term "sulfoxide" is art-recognized and refers to the group —S(O)—.

The term "sulfonate" is art-recognized and refers to the group SO₃H, or a pharmaceutically acceptable salt thereof.

The term "sulfone" is art-recognized and refers to the group —S(O)₂—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^e$ or —SC(O)R$^e$ wherein R$^e$ represents a hydrocarbyl.

The term "thioether", as used herein, is equivalent to an ether, wherein the oxygen is replaced with a sulfur.

The term "urea" is art-recognized and may be represented by the general formula

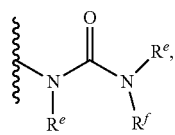

wherein R$^e$ and R$^f$ independently represent hydrogen or a hydrocarbyl.

The term "modulate" as used herein includes the inhibition or suppression of a function or activity (such as cell proliferation) as well as the enhancement of a function or activity.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula (IA) and Formula (IB). Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula (IA) and Formula (IB) are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula (IA) and Formula (IB) for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula (IA) and Formula (IB) or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of Formula (IA) and Formula (IB)). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs include using ester or phosphoramidate as biologically labile or cleavable (protecting) groups. The prodrugs of this disclosure are metabolized to produce a compound of Formula (IA) and Formula (IB). The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "logS" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

Methods of using compounds disclosed herein are also provided. The disclosure also includes pharmaceutical compositions comprising one or more SERT inhibiting compounds (e.g., Formula (IA)), PDE4 inhibiting compounds (e.g., Formula (IB)), or compounds that inhibit SERT and PDE4 (e.g., Formula (IB)), as described herein, or a pharmaceutically acceptable salt thereof, and a pharmaceutically acceptable excipient. In some embodiments, pharmaceutical compositions reported herein can be provided in a unit dosage form (e.g., capsule, tablet or the like). Pharmaceutical compositions comprising a compound of Formula (IA) or Formula (IB) can be provided in an oral dosage form such as a capsule or tablet. The oral dosage form optionally comprises one or more fillers, disintigrants, lubricants, glidants, anti-adherents and/or anti-statics. In some embodiments, an oral dosage form is prepared via dry blending. In some embodiments, an oral dosage form is a tablet and is prepared via dry granulation. For example, a SERT inhibitor compound (e.g., Formula (IA)), a PDE4 inhibitor compound (e.g., Formula (IB)), or a dual inhibitor compound (e.g., Formula (IB)) of the present disclosure can be formulated as a test article for evaluation in animal models and (if appropriate) subsequent human clinical trials to determine the dosed at a therapeutically effective dose and dose frequency for humans. The pharmaceutical compositions may be orally administered in any orally acceptable dosage form. Accordingly, a patient and/or subject can be selected for treatment using a compound described herein by first evaluating the patient and/or subject to determine whether the subject is in need of inhibition of SERT, PDE4, or both, and if the subject is determined to be in need of inhibition of SERT, PDE4, or both, then administering to the subject a pharmaceutical composition comprising one or more compounds described herein, or pharmaceutically acceptable salts thereof.

The compounds described herein may be administered to treat CNS disorders and/or inflammatory conditions. Exemplary CNS disorders include generalized anxiety, acute anxiety and panic attacks, social anxiety, panic disorders, major depressive disorder, cognitive disorders, including Alzheimer's disease and other neurodegenerative disorders, neurodevelopmental disorders, schizophrenia, bipolar disorder, obsessive-compulsive disorder, multiple sclerosis, attention deficit-hyperactivity disorder, Bulimia nervosa, Huntington's disease, stroke, autism, premenstrual dysphoric disorder. Exemplary inflammatory conditions include chronic obstructive pulmonary disease (COPD), asthma and rheumatoid arthritis.

In some embodiments, methods of treating a patient suffering from a disease comprise administering to a patient a composition comprising a compound disclosed herein for the treatment or prevention of a mental health disorder. In some embodiments, methods of treating a patient suffering from a disease comprise administering to a patient a composition comprising a compound disclosed herein for the treatment or prevention of a diagnosed condition selected from anxiety and depression. In some embodiments, the compound disclosed herein is administered to the patient in a unit dose. In some embodiments, a method comprises the administration to a patient in need thereof of a therapeutically effective amount of a compound of Formula (IA) or Formula (IB) for the treatment of a disease selected from the group consisting of mild to moderate depression and major depressive episodes. In some embodiments, a method comprises the administration to a patient in need thereof of a therapeutically effective amount of a compound of Formula (IA) or Formula (IB) for the treatment of anxiety. In some embodiments, a method comprises the administration to a patient in need thereof of a therapeutically effective amount of a compound of Formula (IA) or Formula (IB) for the treatment of depression. In some embodiments, a method comprises the administration to a patient in need thereof of a therapeutically effective amount of a compound of Formula (IA) or Formula (IB) for the treatment of a condition selected from the group consisting of: anxiety associated with depression, anxiety with depression, mixed anxiety and depressive disorder. In some embodiments, a method comprises the administration to a patient in need thereof of a therapeutically effective amount of a compound of Formula (IA) or Formula (IB) for the treatment of anxiety and hysteria or anxiety and depression.

Unless otherwise indicated in the tables of compounds herein, the abbreviation RAC or rac indicates a racemic mixture, and DIAST indicates a specific diastereomer. In illustrative embodiments, although a compound may be depicted with ⟋ or ⟍ bonds, such a depiction may be denoting relative stereochemistry based on elution peaks from a chiral separation.

EXAMPLES

LC/MS spectra were obtained using Agilent 1200\G1956A or SHIMADZU LCMS-2020. Standard LC/MS conditions were as follows (running time 1.55 minutes):

Acidic condition: Mobile Phase A: 0.0375% TFA in water (v/v). Mobile Phase B: 0.01875% TFA in acetonitrile (v/v); Column: Kinetex EVO C18 30*2.1 mm, 5 μm.

Basic condition: Mobile Phase A: 0.025% $NH_3 \cdot H_2O$ in water (v/v). Mobile Phase B: Acetonitrile; Column: Kinetex EVO C18 2.1×30 mm, 5 μm.

| | | 5-95AB_0.8 min | |
|---|---|---|---|
| HPLC | Instrument | SHIMADZU LCMS-2020; | |
| | Software | LabSolution Version 5.97SP1 | |
| | Column | Kinetex ® EVO C18 2.1 × 30 mm 5 um | |
| | Mobile Phase | A: 0.0375% TFA in water (v/v) | |
| | | B: 0.01875% TFA in Acetonitrile (v/v) | |
| | | Time (min) | B (%) | Flow (mL/min) |
| | Gradient | 0.00 | 5.0 | 2.0 |
| | | 0.60 | 95.0 | 2.0 |
| | | 0.78 | 95.0 | 2.0 |
| | | 0.79 | 5.0 | 2.0 |
| | | 0.80 | 5.0 | 2.0 |

| 5-95AB_0.8 min | |
|---|---|
| Column Temp | 50° C. |
| Detector | PDA (220 nm & 254 nm) |
| MS Ionization source | ESI |
| Drying Gas | N2 |
| Drying Gas Flow | 15 (L/min) |
| DL Voltage | 120 (v) |
| Qarray DC Voltage | 20 (V) |
| MS Polarity | Positive |
| MS Mode | Scan |
| Mass range | 100-1000 |

TABLE of

| Abbreviations | |
|---|---|
| Ac | Acetyl |
| Et | Ethyl |
| Me | Methyl |
| Ms | Methanesulfonyl |
| Ts | p-Toluenesulfonyl |
| Tol | toluene |
| HPLC | High Performance Liquid Chromatography |
| DMSO | Dimethyl sulfoxide |
| LC-MS | Liquid chromatography-mass spectrometry |
| NMR | Nuclear magnetic resonance |
| m | multiplet |
| d | Doublet |
| S | singlet |
| t | triplet |
| SFC | Supercritical fluid chromatography |
| IPA | isopropanol |
| ESI | Electrospray ionization |
| EtOAC | Ethyl acetate |
| t-buOK | Potassium tertbutoxide |
| ACN | acetonitrile |
| Ac | acetate |
| MS | Molecular sieves |
| DCM | dichloromethane |
| TMS | trimethylsilyl |

Summary of Mesembrine and Mesembrenone Compound Designations

| Compound | Racemic | (−) enantiomer | (+) enantiomer |
|---|---|---|---|
| Mesembrine | Compound 022 | Compound 001 | Compound 002 |
| Mesembrenone | Compound 016 | Compound 003 | Compound 004 |

Example 1 (3aR)-3a-(3-bromo-4,5-dimethoxy-phenyl)-1-methyl-2,3,7,7a-tetrahydroindol-6-one (130)

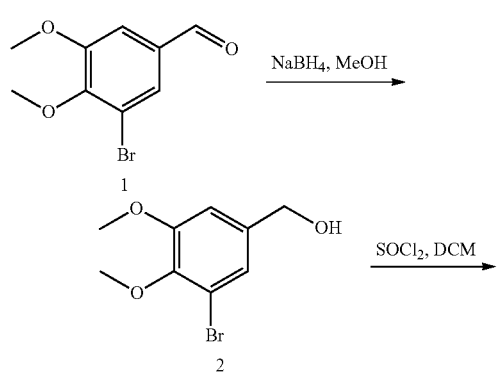

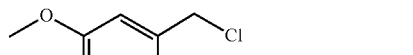

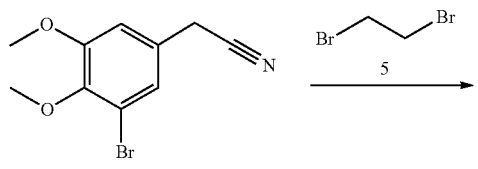

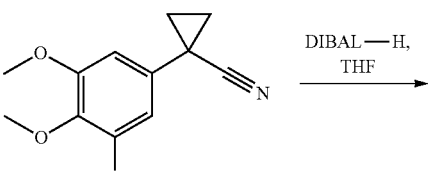

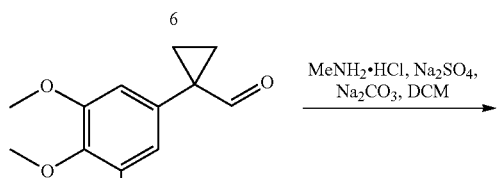

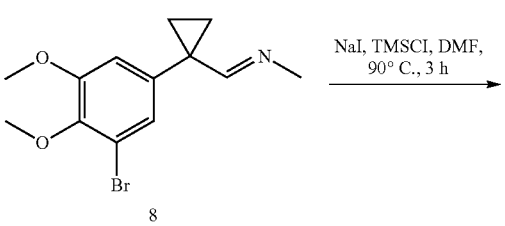

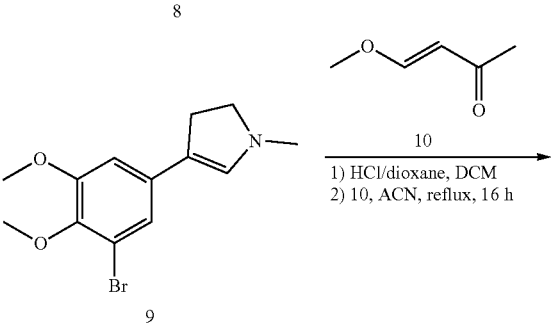

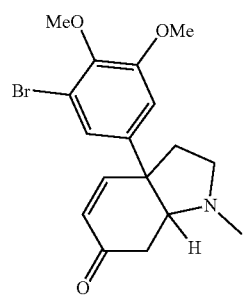

Step 1—(3-bromo-4,5-dimethoxy-phenyl)methanol

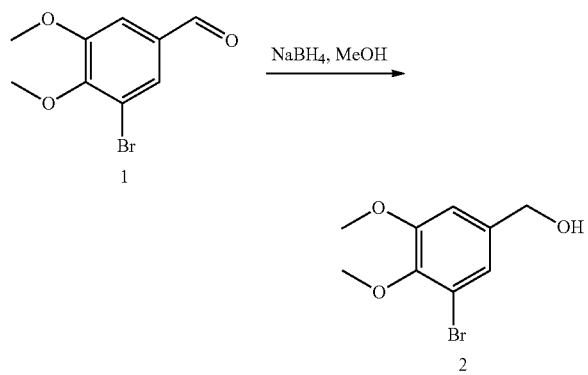

To a solution of 3-bromo-4,5-dimethoxy-benzaldehyde (10.0 g, 40.8 mmol) in EtOH (100 mL) was added NaBH₄ (1.54 g, 40.8 mmol) at 0° C. The mixture was stirred at 25° C. for 1.5 hours. On completion, the mixture was poured to the water (200 mL) and extracted with ethyl acetate (600 mL). The organic layers was dried by sodium sulfate, filtered and concentrated in vacuo to give (3-bromo-4,5-dimethoxy-phenyl)methanol (9.30 g, 88 yield) as a yellow liquid.

LC-MS (ESI+) m/z 230.8 (M+H)⁺

¹H NMR (400 MHz, CDCl₃): δ 7.11 (1H, s), 6.88 (1H, s), 4.61 (2H, d, J=6.0 Hz), 3.86 (6H, d, J=12.0 Hz).

Step 2—1-bromo-5-(chloromethyl)-2,3-dimethoxy-benzene

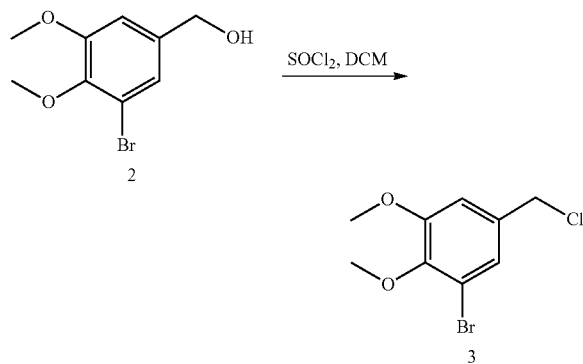

To a solution of (3-bromo-4,5-dimethoxy-phenyl)methanol (9.30 g, 37.6 mmol) in DCM (200 mL) was added SOCl₂ (17.9 g, 150 mmol) at 0° C. The mixture was stirred at 25° C. for 1.5 hours. On completion, the mixture was poured to the water (100 mL) and extracted with ethyl acetate (300 mL). The organic layers was dried by sodium sulfate, filtered and concentrated in vacuo to give 1-bromo-5-(chloromethyl)-2,3-dimethoxy-benzene (9.2 g, 83% yield) as a yellow liquid.

¹H NMR (400 MHz, CDCl₃): δ 7.09 (1H, d, J=1.6 Hz), 6.81 (1H, d, J=1.6 Hz), 4.43 (2H, s), 3.81 (3H, s), 3.78 (3H, s)

Step 3—2-(3-bromo-4,5-dimethoxy-phenyl)acetonitrile

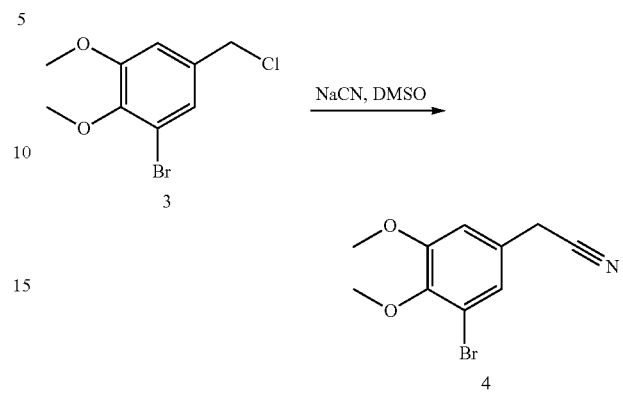

To a solution of 1-bromo-5-(chloromethyl)-2,3-dimethoxy-benzene (9.20 g, 34.6 mmol,) in DMSO (100 mL) was added NaCN (3.40 g, 69.3 mmol). The mixture was stirred at 25° C. for 2.5 hours. On completion, the mixture was poured to the NaOH solution to adjust pH>11 and extracted with ethyl acetate (1000 mL). The organic layers was dried by sodium sulfate, filtered and concentrated in vacuo to give 2-(3-bromo-4,5-dimethoxy-phenyl)acetonitrile (8.3 g, 84.2% yield) as a yellow liquid.

¹H NMR (400 MHz, CDCl₃): δ 7.02 (1H, d, J=1.6 Hz), 6.74 (1H, d, J=1.6 Hz), 4.05 (1H, d, J=7.2 Hz), 3.82 (3H, s), 3.78 (3H, s), 3.62 (2H, s), 1.97 (1H, s), 1.19 (1H, t, J=7.2 Hz).

Step 4—1-(3-bromo-4,5-dimethoxy-phenyl)cyclopropanecarbonitrile

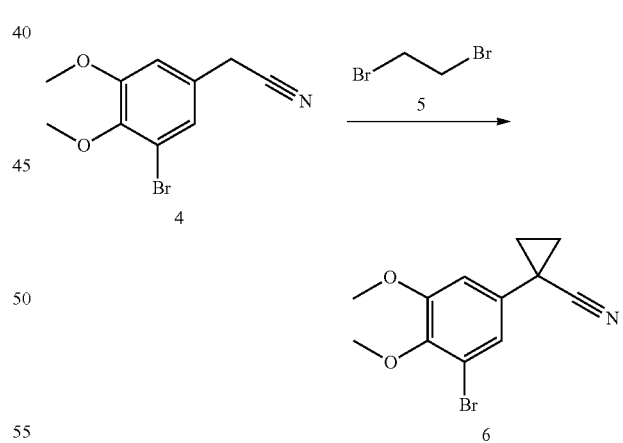

To a solution of 2-(3-bromo-4,5-dimethoxy-phenyl)acetonitrile (7.80 g, 30.5 mmol) in THF (90 mL) was added LDA (2 M, 38.1 mL). Then mixture was added 1,2-dibromoethane (6.87 g, 36.6 mmol, 2.76 mL). The mixture was stirred at 25° C. for 3 hours. On completion, the mixture was poured to the NH₄Cl solution (100 mL) and extracted with ethyl acetate (300 mL). The organic layers was dried by sodium sulfate, filtered and concentrated in vacuo to give the residue. The residue was purified by column chromatography (SiO₂, Petroleum ether/Ethyl acetate=0/1 to 4/1) to give 1-(3-bromo-4,5-dimethoxy-phenyl)cyclopropanecarbonitrile (4.70 g, 50% yield) as a yellow oil.

LC-MS (ESI+) m/z 283.8 (M+H)+

$^1$H NMR (400 MHz, CDCl$_3$): δ 6.89 (1H, d, J=2.0 Hz), 6.83 (1H, d, J=2.0 Hz), 3.83 (3H, s), 3.77 (3H, s), 1.60-1.66 (2H, m), 1.28-1.33 (2H, m).

Step 5—1-(3-bromo-4,5-dimethoxy-phenyl)cyclopropanecarbonitrile

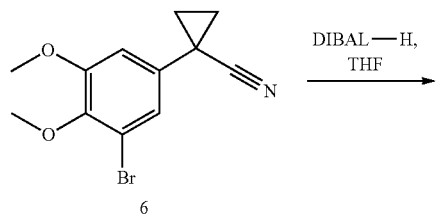

To a solution of 1-(3-bromo-4,5-dimethoxy-phenyl)cyclopropanecarbonitrile (4.7 g, 16.7 mmol) in THF (50 mL) was added DIBAL-H (1 M, 25.0 mL) at 0° C. The mixture was stirred at 25° C. 16 hours. On completion, the mixture was poured to the 2M HCl (10 mL) and extracted with ethyl acetate (30 mL). The organic layers was dried by sodium sulfate, filtered and concentrated in vacuo to give 1-(3-bromo-4,5-dimethoxy-phenyl)cyclopropanecarbaldehyde (4.60 g, 87% yield) as a yellow oil.

$^1$H NMR (400 MHz, CDCl$_3$): δ 9.08 (1H, s), 6.99 (1H, d, J=2.0 Hz), 6.73 (1H, d, J=2.0 Hz), 3.79 (3H, s), 3.78 (3H, s), 1.45-1.52 (2H, m), 1.28-1.34 (2H, m).

Step 6—(E)-1-[1-(3-bromo-4,5-dimethoxy-phenyl)cyclopropyl]-N-methyl-methanimine

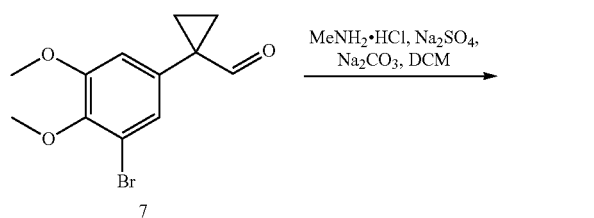

To a solution of 1-(3-bromo-4,5-dimethoxy-phenyl)cyclopropanecarbaldehyde (4.60 g, 16.1 mmol,) and methanamine;hydrochloride (5.45 g, 80.7 mmol) in DCM (200 mL) was added Na$_2$CO$_3$ (5.13 g, 48.4 mmol) and Na$_2$SO$_4$ (34.4 g, 242 mmol). The mixture was stirred at 25° C. for 16 hours. On completion, the reaction mixture was filtered, concentrated in vacuo to give (E)-1-[1-(3-bromo-4,5-dimethoxy-phenyl)cyclopropyl]-N-methyl-methanimine (4.45 g, 86% yield) as a yellow liquid.

$^1$H NMR (400 MHz, CDCl$_3$): δ 9.08 (1H, s), 7.40 (1H, d, J=1.6 Hz), 7.01 (1H, d, J=2.0 Hz), 6.74 (1H, d, J=2.0 Hz), 3.77 (6H, d, J=9.2 Hz), 3.17 (3H, d, J=1.6 Hz), 1.16-1.21 (2H, m), 1.04-1.10 (2H, m).

Step 7—(E)-1-[1-(3-bromo-4,5-dimethoxy-phenyl)cyclopropyl]-N-methyl-methanimine

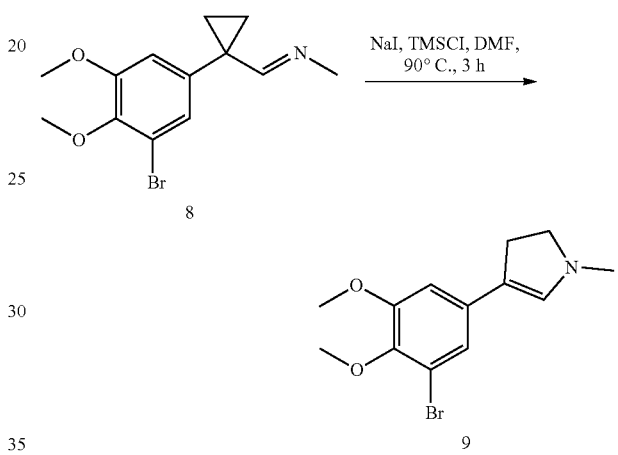

To a solution of (E)-1-[1-(3-bromo-4,5-dimethoxy-phenyl)cyclopropyl]-N-methyl-methanimine (1.0 g, 3.35 mmol) in DMF (5 mL) was added NaI (50.2 mg, 335 umol) and TMSCl (36.4 mg, 335 umol). The mixture was stirred at 60° C. for 2 hours. On completion, the mixture was poured to the water (20 mL) and extracted with ethyl acetate (50 mL). The organic layer was dried by sodium sulfate, filtered and concentrated in vacuo to give 4-(3-bromo-4,5-dimethoxy-phenyl)-1-methyl-2,3-dihydropyrrole (730 mg, 29% yield) as a yellow liquid.

LC-MS (ESI+) m/z 299.9 (M+H)+.

Step 8—(3aR)-3a-(3-bromo-4,5-dimethoxy-phenyl)-1-methyl-2,3,7,7a-tetrahydroindol-6-one (130

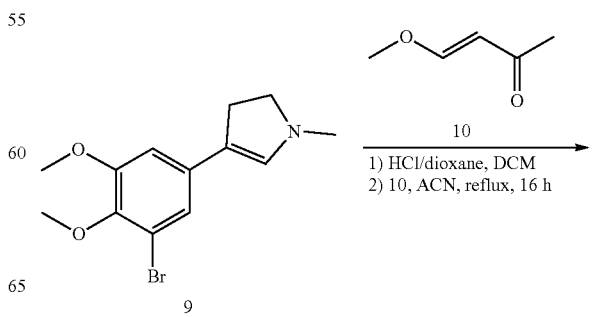

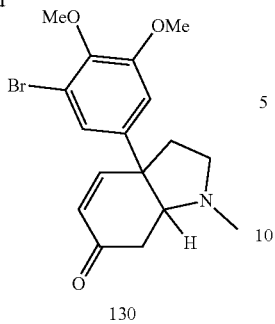

130

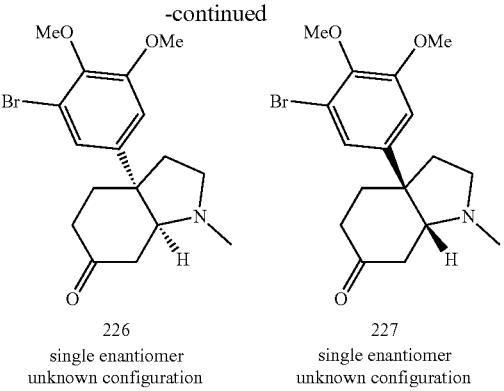

226
single enantiomer
unknown configuration 227
single enantiomer
unknown configuration To a solution of 4-(3-bromo-4,5-dimethoxy-phenyl)-1-methyl-2,3-dihydropyrrole (730 mg, 2.45 mmol) in DCM (6 mL) was added HCl/dioxane (4M, 1.99 mL). After addition, the mixture was filtered, concentrated in vacuo to give the residue, and then (E)-4-methoxybut-3-en-2-one (270 mg, 2.69 mmol) in ACN (3 mL) was added the residue. The mixture was stirred at 90° C. for 16 hours. On completion, on cooling the solvent was removed under reduced pressure and the resulting dark oil partitioned between HCl (2M/L, 10 mL) and ether (50 mL). The aqueous fraction was washed with further ether (2×20 mL), and then brought to basic pH using NaOH (3 M, 20 mL) solution. The organic components were then extracted into ethyl acetate (4×20 mL) and the combined extracts washed with brine (1×200 mL) and dried (Na$_2$SO$_4$). The residue was purified by prep-HPLC (column: Phenomenex C18 150*25 mm; mobile phase: [water(NH$_4$HCO$_3$)-ACN];B %: 25%-55%,8 min) to give (3aR)-3a-(3-bromo-4,5-dimethoxy-phenyl)-1-methyl-2,3,7,7a-tetrahydroindol-6-one (29.3 mg, 3% yield) as an off-white solid.

LC-MS (ESI$^+$) m/z 367.9 (M+H)$^+$.

$^1$H NMR (400 MHz, CDCl$_3$) δ 7.14 (d, J=2.0 Hz, 1H), 6.83 (d, J=2.0 Hz, 1H), 6.76-6.66 (m, 1H), 6.14 (d, J=10.0 Hz, 1H), 3.89 (d, J=5.6 Hz, 6H), 3.39-3.29 (m, 1H), 2.69 (s, 1H), 2.66-2.59 (m, 1H), 2.57-2.47 (m, 2H), 2.47-2.39 (m, 1H), 2.35 (s, 3H), 2.31-2.18 (m, 1H).

Step 9

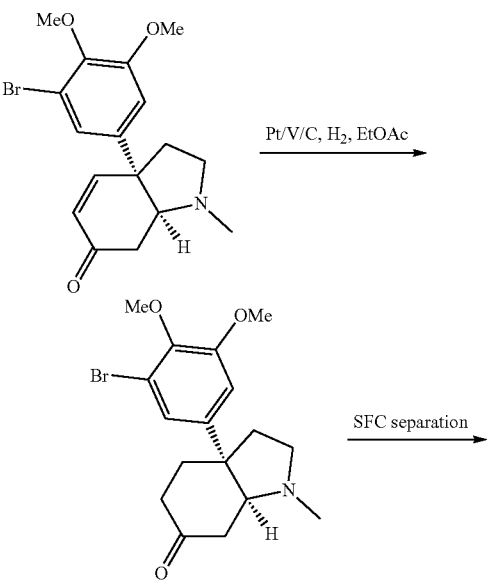

A mixture of 3a-(3-bromo-4,5-dimethoxy-phenyl)-1-methyl-2,3,7,7a-tetrahydroindol-6-one (10.0 mg, 27.3 umol), Pt/V/C (10 mg, 2.73 umol), H$_2$ (55.15 ug, 27.30 umol,) in EtOAc (1 mL) was degassed and purged with H$_2$ for 3 times, and then the mixture was stirred at 25° C. for 2 hours under H$_2$ atmosphere. On completion, The residue was purified by prep-HPLC (column: Phenomenex C18 150*25 mm*10 um; mobile phase: [water(NH$_4$HCO$_3$)-ACN];B %: 33%-63%,8 min) to give 3a-(3-bromo-4,5-dimethoxy-phenyl)-1-methyl-2,3,4,5,7,7a-hexahydroindol-6-one (20 mg, 30% yield,) as a white solid.

LC-MS (ESI$^+$) m/z 368.0 (M+H)$^+$. 10-[(2S,3S)-3-[(3'aS,4R,7'aS)-3'a-(3,4-dimethoxyphenyl)-1'-methyl-spiro[1,3-dioxolane-2,6'-2,3,4,5,7,7a-hexahydroindole]-4-yl]-2,3-dihydroxy-propyl]-7,8-dimethyl-benzo[g]pteridine-2,4-dione was separated by SFC (column: DAICEL CHIRALPAK IE(250 mm*30 mm,10 um); mobile phase: [Neu-EtOH];B %: 20%-20%,C20;80 min) to give (3aS,7aS)-3a-(3-bromo-4,5-dimethoxy-phenyl)-1-methyl-2,3,4,5,7,7a-hexahydroindol-6-one (6.18 mg, 29% yield) as a yellow gum and (3aR,7aR)-3a-(3-bromo-4,5-dimethoxy-phenyl)-1-methyl-2,3,4,5,7,7a-hexahydroindol-6-one (5.49 mg, 26% yield) as a yellow gum.

226:

LC-MS (ESI$^+$) m/z 368.0 (M+H)$^+$ $^1$H NMR (400 MHz, CDCl$_3$) δ=7.07 (d, J=2.0 Hz, 1H), 6.78 (d, J=2.0 Hz, 1H), 3.80 (d, J=11.3 Hz, 6H), 3.18-3.01 (m, 1H), 2.85 (s, 1H), 2.53 (s, 2H), 2.46-2.33 (m, 1H), 2.30-2.21 (m, 4H), 2.20-2.15 (m, 1H), 2.15-2.07 (m, 2H), 2.06-1.97 (m, 2H), 1.97-1.97 (m, 1H), 1.87-1.33 (m, 2H).

227:

LC-MS (ESI$^+$) m/z 368.0 (M+H)$^+$ $^1$H NMR (400 MHz, CDCl$_3$) δ=7.07 (d, J=2.4 Hz, 1H), 6.78 (d, J=2.0 Hz, 1H), 3.80 (d, J=11.2 Hz, 6H), 3.15-3.02 (m, 1H), 2.85 (t, J=3.2 Hz, 1H), 2.53 (d, J=3.6 Hz, 2H), 2.45-2.32 (m, 1H), 2.30-2.21 (m, 4H), 2.16 (s, 1H), 2.15-2.07 (m, 2H), 2.06-1.96 (m, 2H).

Example 2—(3aR,7aS)-3a-(3-iodo-4,5-dimethoxy-phenyl)-1-methyl-2,3,7,7a-tetrahydroindol-6-one (132)

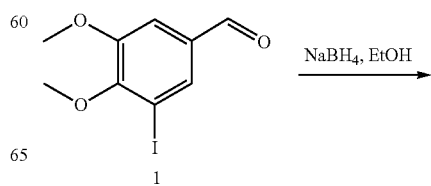

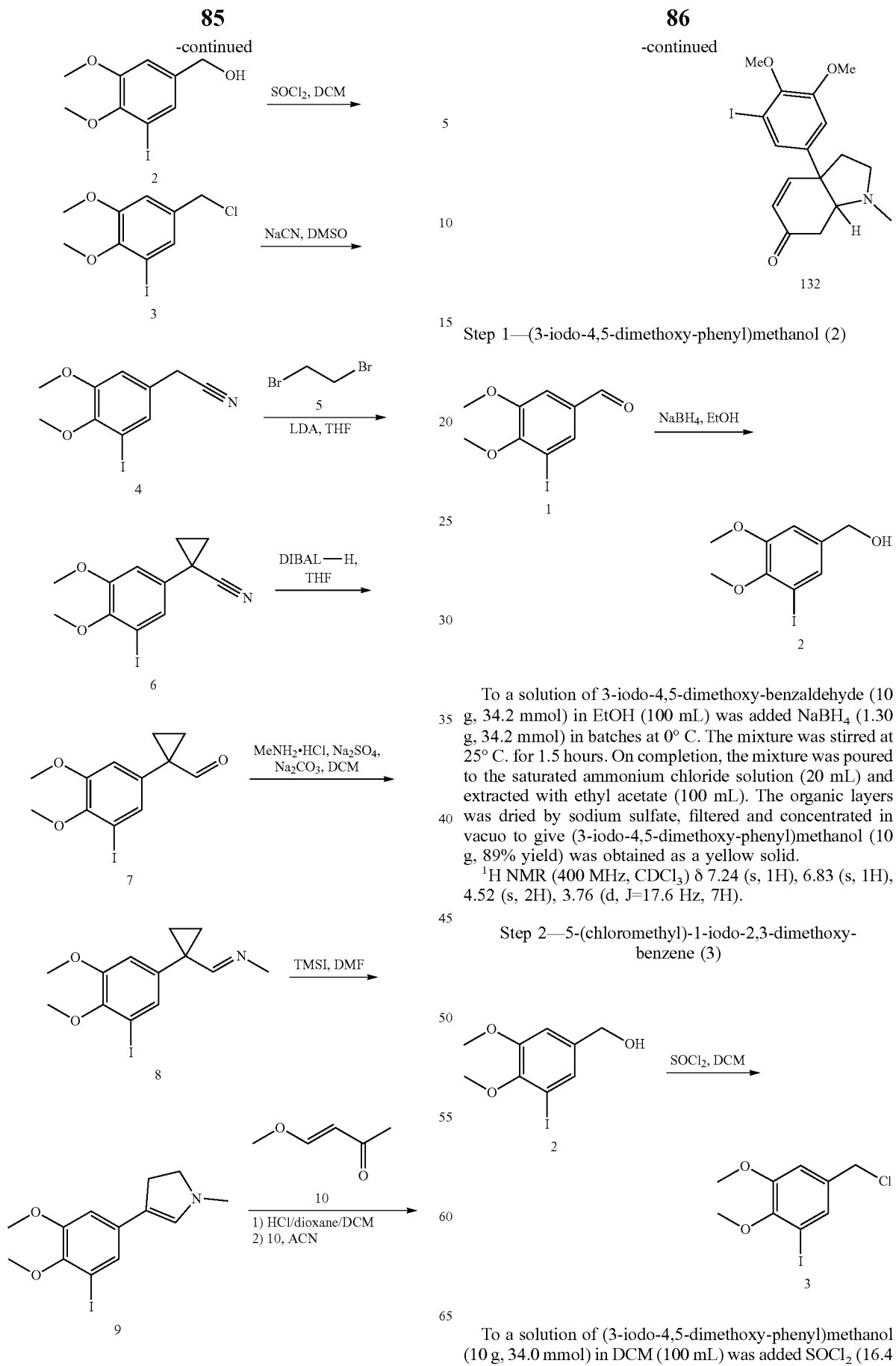

Step 1—(3-iodo-4,5-dimethoxy-phenyl)methanol (2)

To a solution of 3-iodo-4,5-dimethoxy-benzaldehyde (10 g, 34.2 mmol) in EtOH (100 mL) was added NaBH$_4$ (1.30 g, 34.2 mmol) in batches at 0° C. The mixture was stirred at 25° C. for 1.5 hours. On completion, the mixture was poured to the saturated ammonium chloride solution (20 mL) and extracted with ethyl acetate (100 mL). The organic layers was dried by sodium sulfate, filtered and concentrated in vacuo to give (3-iodo-4,5-dimethoxy-phenyl)methanol (10 g, 89% yield) was obtained as a yellow solid.
$^1$H NMR (400 MHz, CDCl$_3$) δ 7.24 (s, 1H), 6.83 (s, 1H), 4.52 (s, 2H), 3.76 (d, J=17.6 Hz, 7H).

Step 2—5-(chloromethyl)-1-iodo-2,3-dimethoxy-benzene (3)

To a solution of (3-iodo-4,5-dimethoxy-phenyl)methanol (10 g, 34.0 mmol) in DCM (100 mL) was added SOCl$_2$ (16.4 g, 137 mmol, 10 mL). The mixture was stirred at 0° C. for 2 hours. On completion, the reaction mixture was concentrated in vacuo to give the residue, saturated sodium bicarbonate solution was added to adjust PH>7, and extracted with ethyl acetate (600 mL). The organic layers was dried by sodium sulfate, filtered and concentrated in vacuo to give 5-(chloromethyl)-1-iodo-2,3-dimethoxy-benzene (10 g, 84% yield) was obtained as a yellow solid.

$^1$H NMR (400 MHz, CDCl$_3$) δ 7.29 (d, J=2.0 Hz, 1H), 6.85 (d, J=2.0 Hz, 1H), 4.42 (s, 2H), 3.78 (d, J=17.1 Hz, 6H).

Step 3—2-(3-iodo-4,5-dimethoxy-phenyl)acetonitrile 2-(3-iodo-4,5-dimethoxy-phenyl)acetonitrile (4)

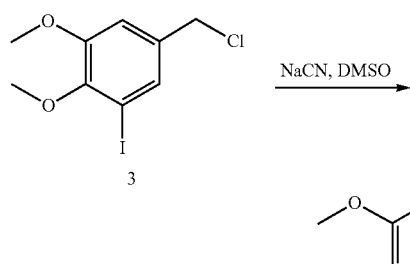

To a solution of 5-(chloromethyl)-1-iodo-2,3-dimethoxy-benzene (10 g, 32.0 mmol) in DMSO (100 mL) was added NaCN (3.14 g, 63.9 mmol). The mixture was stirred at 25° C. for 16 hours. On completion, the mixture was saturated sodium bicarbonate solution was added to adjust pH>7, extracted with ethyl acetate (1000 mL) and washed by brine (500 mL). The organic layer was dried by sodium sulfate, filtered and concentrated in vacuo to give 2-(3-iodo-4,5-dimethoxy-phenyl)acetonitrile 2-(3-iodo-4,5-dimethoxy-phenyl)acetonitrile (9.0 g, 88% yield) was obtained as a yellow solid.

$^1$H NMR (400 MHz, CDCl$_3$) δ 7.22 (d, J=1.6 Hz, 1H), 6.78 (d, J=1.6 Hz, 1H), 3.81 (s, 3H), 3.76 (s, 3H), 3.60 (s, 2H).

Step 4—1-(3-iodo-4,5-dimethoxy-phenyl)cyclopropanecarbonitrile (6)

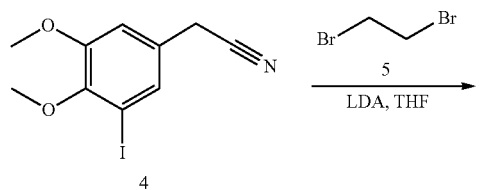

To a solution of 2-(3-iodo-4,5-dimethoxy-phenyl)acetonitrile (9 g, 29.6 mmol, 1 eq.) in THF (90 mL) was added LDA (2 M, 37.1 mL) at 0° C. And then 1,2-dibromoethane (6.69 g, 35.6 mmol, 2.69 mL) was added in the mixture at 0° C. The mixture was stirred at 25° C. for 2 hours. On completion, the mixture was poured to the saturated ammonium chloride solution (100 mL) and extracted with ethyl acetate (450 mL). The organic layer was dried by sodium sulfate, filtered and concentrated in vacuo to give the residue. The residue was purified by column chromatography (SiO$_2$, Petroleum ether/Ethyl acetate=1/0 to 1/5 to give 1-(3-iodo-4,5-dimethoxy-phenyl)cyclopropanecarbonitrile (5.8 g, 53% yield) was obtained as a yellow solid.

$^1$H NMR (400 MHz, CDCl$_3$) δ 7.09 (d, J=2.0 Hz, 1H), 6.86 (d, J=2.0 Hz, 1H), 3.90-3.68 (m, 6H), 1.63 (d, J=2.4 Hz, 2H), 1.30 (d, J=2.4 Hz, 2H).

Step 5—1-(3-iodo-4,5-dimethoxy-phenyl)cyclopropanecarbaldehyde (7)

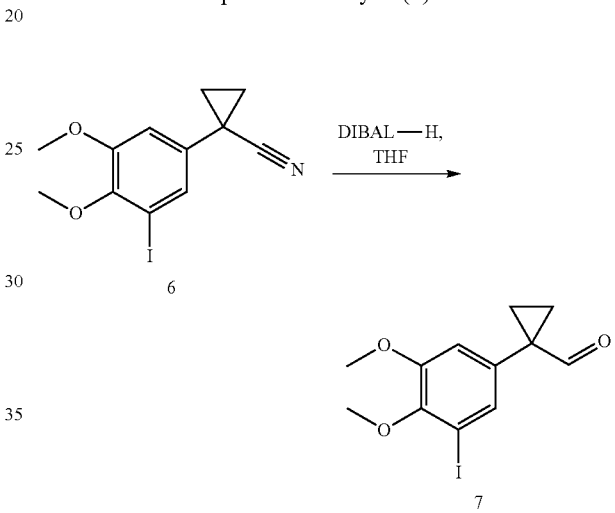

To a solution of 1-(3-iodo-4,5-dimethoxy-phenyl)cyclopropanecarbonitrile (5.8 g, 17.6 mmol) in THF (60 mL) was added DIBAL-H (1 M, 26.4 mL). The mixture was stirred at 0° C. for 16 hours. On completion, the mixture was poured to the diluted hydrochloric acid (2 M, 20 mL) and extracted with ethyl acetate (60 mL). The organic layer was dried by sodium sulfate, filtered and concentrated in vacuo to give 1-(3-iodo-4,5-dimethoxy-phenyl)cyclopropanecarbaldehyde (5.8 g, 94% yield) was obtained as a yellow solid.

$^1$H NMR (400 MHz, CDCl$_3$) δ 9.09 (s, 1H), 7.22-7.18 (m, 1H), 6.76 (d, J=2.0 Hz, 1H), 3.78 (d, J=10.4 Hz, 6H), 1.48 (d, J=2.8 Hz, 2H), 1.34-1.28 (m, 2H).

Step 6—(E)-1-[1-(3-iodo-4,5-dimethoxy-phenyl)cyclopropyl]-N-methyl-methanimine (8)

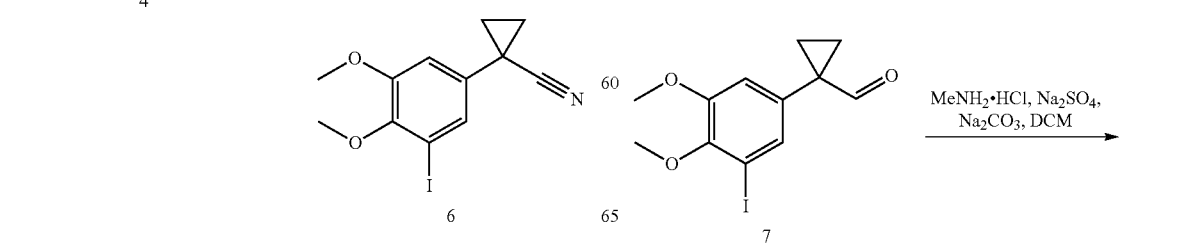

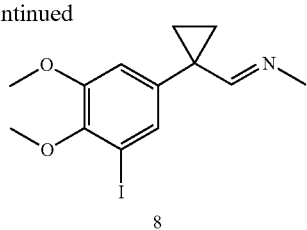

8

To a solution of 1-(3-iodo-4,5-dimethoxy-phenyl)cyclopropanecarbaldehyde (5.8 g, 17.4 mmol) in DCM (60 mL) was added methanamine;hydrochloride (5.90 g, 87.3 mmol), Na$_2$CO$_3$ (5.55 g, 52.3 mmol,) and Na$_2$SO$_4$ (37.2 g, 261 mmol). The mixture was stirred at 25° C. for 16 hours. On completion, the reaction mixture was filtered, concentrated in vacuo to give (E)-1-[1-(3-iodo-4,5-dimethoxy-phenyl)cyclopropyl]-N-methyl-methanimine (5.5 g, 85% yield) was obtained as a yellow oil.

$^1$H NMR (400 MHz, CDCl$_3$) δ 7.41 (d, J=1.6 Hz, 1H), 7.22 (d, J=2.0 Hz, 1H), 6.77 (d, J=2.0 Hz, 1H), 3.76 (d, J=13.6 Hz, 6H), 3.17 (d, J=1.6 Hz, 3H), 1.21-1.16 (m, 2H), 1.09-1.02 (m, 2H).

Step 7—4-(3-iodo-4,5-dimethoxy-phenyl)-1-methyl-2,3-dihydropyrrole (9)

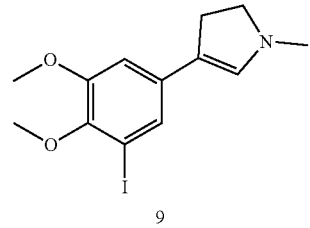

A mixture of (E)-1-[1-(3-iodo-4,5-dimethoxy-phenyl)cyclopropyl]-N-methyl-methanimine (1 g, 2.90 mmol), TMSI (579 mg, 2.90 mmol, 394 uL) in DMF (10 mL) was degassed and purged with N$_2$ for 3 times, and then the mixture was stirred at 60° C. for 0.5 hours under N$_2$ atmosphere. On completion, the mixture was poured to the water (15 mL) and extracted with ethyl acetate (100 mL). Then aqueous phase was saturated sodium bicarbonate solution was added to adjust PH>7, and extracted with ethyl acetate (200 mL). The organic layer was dried by sodium sulfate, filtered and concentrated in vacuo to give 4-(3-iodo-4,5-dimethoxy-phenyl)-1-methyl-2,3-dihydropyrrole (500 mg, 40% yield) was obtained as a yellow oil.

LC-MS (ESI$^+$) m/z 345.9 (M+H)$^+$;

$^1$H NMR (400 MHz, CDCl$_3$) δ 7.07 (d, J=1.6 Hz, 1H), 6.64 (d, J=1.6 Hz, 1H), 6.30 (s, 1H), 3.77 (s, 3H), 3.72 (s, 3H), 3.10 (t, J=9.2 Hz, 2H), 2.67 (t, J=9.2 Hz, 2H), 2.59 (s, 3H).

Step 8—(3aR,7aS)-3a-(3-iodo-4,5-dimethoxy-phenyl)-1-methyl-2,3,7,7a-tetrahydroindol-6-one (132)

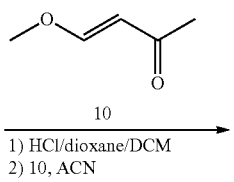

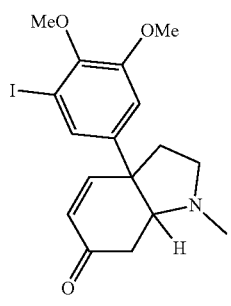

132

To a solution of 4-(3-iodo-4,5-dimethoxy-phenyl)-1-methyl-2,3-dihydropyrrole (400 mg, 938 umol) in DCM (4.0 mL) was HCl/dioxane (4 M, 234 uL) at 25° C. for 10 minutes. After addition, the mixture was filtered, concentrated in vacuo to give the residue. And then (E)-4-methoxybut-3-en-2-one (112 mg, 1.13 mmol, 113 uL) in ACN (4.0 mL) was added the residue. The mixture was stirred at 60° C. for 2 hours. On completion, the reaction mixture was quenched by adding it to a cold saturated aqueous sodium hydroxide solution (30 mL) till pH=8. The aqueous layer was extracted with ethyl acetate (100 mL). The organic layer was separated, dried over anhydrous Na$_2$SO$_4$, filtered and concentrated under reduced pressure to give the residue. The residue was purified by prep-HPLC (FA condition: column: Phenomenex luna C18 150*25 mm*10 um; mobile phase: [water(FA)-ACN];B %: 9%-39%,10 min) to give (3aR,7aS)-3a-(3-iodo-4,5-dimethoxy-phenyl)-1-methyl-2,3,7,7a-tetrahydroindol-6-one (80 mg, 19% yield) was obtained as a yellow gum.

LC-MS (ESI$^+$) m/z 413.9 (M+H)$^+$;

$^1$H NMR (400 MHz, CDCl$_3$) δ 7.32 (d, J=2.0 Hz, 1H), 6.87 (d, J=2.0 Hz, 1H), 6.71 (dd, J=1.6, 10.0 Hz, 1H), 6.18 (d, J=10.4 Hz, 1H), 3.87 (d, J=11.2 Hz, 6H), 3.38 (dt, J=3.2, 9.2 Hz, 1H), 2.85 (s, 1H), 2.71-2.60 (m, 2H), 2.55 (d, J=4.0 Hz, 1H), 2.50 (dd, J=3.6, 11.1 Hz, 1H), 2.40 (s, 3H), 2.32-2.19 (m, 1H).

Example 3—(3aR,7aS)-3a-(3-fluoro-4,5-dimethoxy-phenyl)-1-methyl-2,3,7,7a-tetrahydroindol-6-one (133)

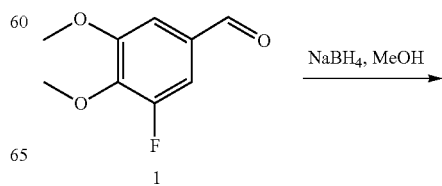

91

-continued

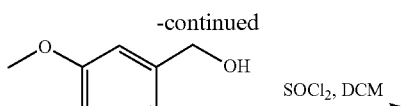

2

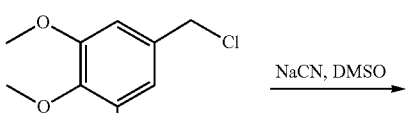

3

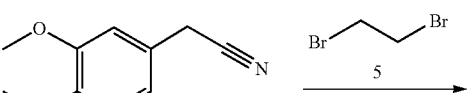

4

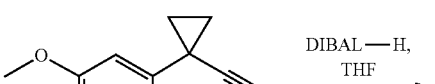

6

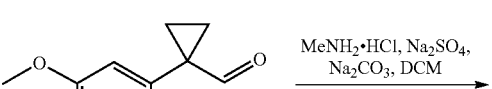

7

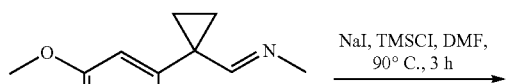

8

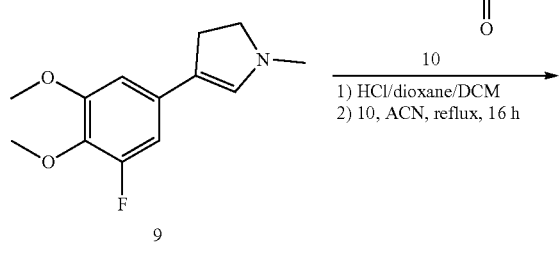

9

92

-continued

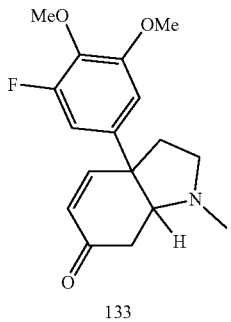

133

Step 1—(3-fluoro-4,5-dimethoxy-phenyl)methanol

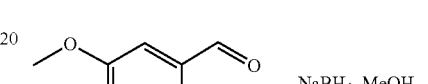

1

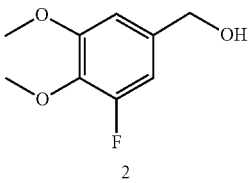

2

A mixture of 3-fluoro-4,5-dimethoxy-benzaldehyde (4.20 g, 22.81 mmol, CAS: 71924-61-3) in EtOH (60 mL) was added NaBH₄ (949 mg, 25.1 mmol,) at 0° C., then the mixture was stirred at 25° C. for 3 hours. On completion, the mixture was poured to the ammonium chloride (10 mL) and extracted with ethyl acetate (30 mL). The organic layers was dried by sodium sulfate, filtered and concentrated in vacuo to give (3-fluoro-4,5-dimethoxy-phenyl)methanol (4.00 g, 89.50% yield, 95% purity) as a yellow oil.

$^{1}$H NMR (400 MHz, CDCl$_{3}$) δ=6.80-6.56 (m, 2H), 4.55 (s, 2H), 3.90-3.77 (m, 6H).

Step 2—(chloromethyl)-1-fluoro-2,3-dimethoxy-benzene

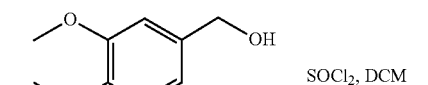

2

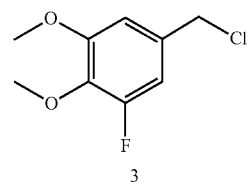

3

A mixture of (3-fluoro-4,5-dimethoxy-phenyl)methanol (4.00 g, 21.5 mmol) in DCM (40 mL) was added SOCl$_2$ (6.39 g, 53.7 mmol) at 0° C., then the mixture was stirred at 25° C. for 3 hours.

On completion, the mixture was poured to the sodium bicarbonate (10 mL) and extracted with ethyl acetate (100 mL). The organic layers was dried by sodium sulfate, filtered and concentrated in vacuo to give 5-(chloromethyl)-1-fluoro-2,3-dimethoxy-benzene (4.00 g, 91% yield) was obtained as a yellow oil.

$^1$H NMR (400 MHz, CDCl$_3$) δ=6.88-6.56 (m, 2H), 4.44 (s, 2H), 3.91-3.80 (m, 6H).

Step 3—2-(3-fluoro-4,5-dimethoxy-phenyl)acetonitrile

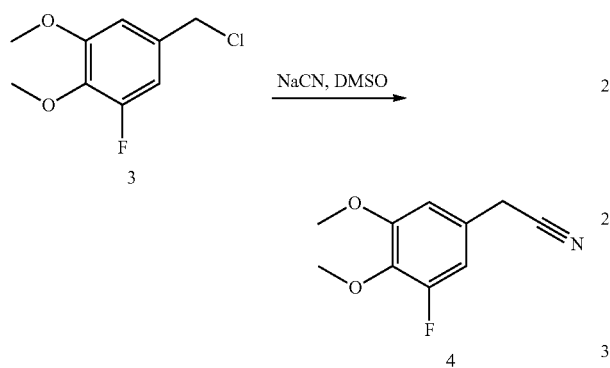

A mixture of 5-(chloromethyl)-1-fluoro-2,3-dimethoxy-benzene (4.00 g, 19.6 mmol) in DMSO (40 mL) was added NaCN (1.92 g, 39.1 mmol), then the mixture was stirred at 25° C. for 16 hours. On completion, the mixture was poured to the saturated sodium bicarbonate solution (40 mL) to adjust PH>7 and extracted with ethyl acetate (100 mL*3), then the organic layers washed by brine (50 mL). The organic layers was dried by sodium sulfate, the residue was purified by column chromatography (SiO$_2$, Petroleum ether/Ethyl acetate=10/1 to 3/1) to give 2-(3-fluoro-4,5-dimethoxy-phenyl)acetonitrile (3.6 g, 90% yield) as a yellow oil.

$^1$H NMR (400 MHz, CDCl$_3$) δ=6.80-6.50 (m, 2H), 3.90-3.75 (m, 6H), 3.62 (s, 2H).

Step 4—1-(3-bromo-4,5-dimethoxy-phenyl)cyclopropanecarbonitrile

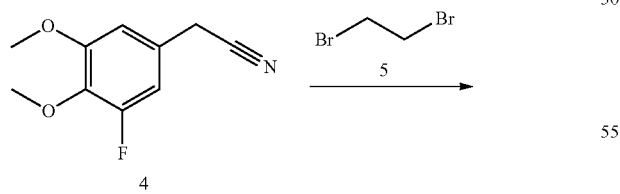

A mixture of 2-(3-fluoro-4,5-dimethoxy-phenyl)acetonitrile (3.60 g, 18.4 mmol) in THF (36 mL) was added LDA (2 M, 23.0 mL), then 1,2-dibromoethane (4.16 g, 22.1 mmol, 1.67 mL) was added above mixture, the mixture was stirred at 25° C. for 2 hours. On completion, the mixture was poured to the water (100 mL) and extracted with ethyl acetate (300 mL). The organic layers was dried by sodium sulfate, filtered and concentrated in vacuo to give the residue. The residue purified by column chromatography (SiO$_2$, Petroleum ether/Ethyl acetate=10/1 to 3/1) to give 1-(3-fluoro-4,5-dimethoxy-phenyl)cyclopropanecarbonitrile (3.70 g, 14.38 mmol, 78% yield) as a yellow oil.

$^1$H NMR (400 MHz, CDCl$_3$) δ=6.67 (t, J=1.8 Hz, 1H), 6.49 (dd, J=2.2, 12.0 Hz, 1H), 3.99-3.74 (m, 6H), 1.72-1.60 (m, 2H), 1.34-1.25 (m, 2H).

Step 5 1-(3-fluoro-4,5-dimethoxy-phenyl)cyclopropanecarbaldehyde

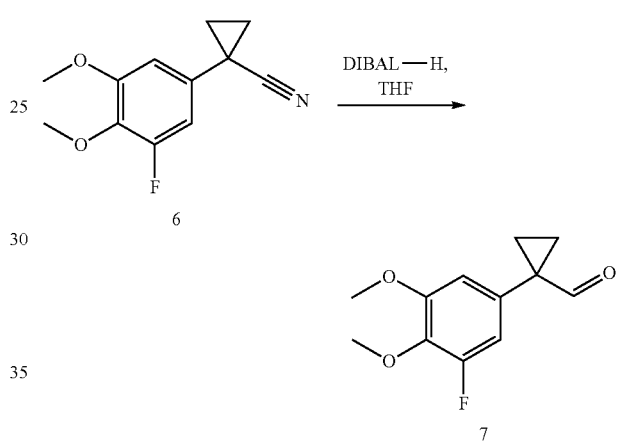

A mixture of 1-(3-fluoro-4,5-dimethoxy-phenyl)cyclopropanecarbonitrile (3.70 g, 16.7 mmol), DIBALH (1 M, 25.1 mL) in THF (37 mL) was degassed and purged with N2 for 3 times, and then the mixture was stirred at 25° C. for 16 hours under N2 atmosphere. On completion, the mixture was poured to the HCl (2M, 50 mL) and extracted with ethyl acetate (300 mL). The organic layer was dried by sodium sulfate, filtered and concentrated in vacuo to give 1-(3-fluoro-4,5-dimethoxy-phenyl)cyclopropanecarbaldehyde (3.70 g, 13.2 mmol, 79% yield) as brown oil.

1H NMR (400 MHz, CDCl$_3$) δ=9.11 (s, 1H), 7.15-6.52 (m, 2H), 4.07-3.60 (m, 6H), 1.61-1.40 (m, 2H), 1.37-1.23 (m, 2H).

Step 6—(E)-1-[1-(3-fluoro-4,5-dimethoxy-phenyl)cyclopropyl]-N-methyl-methanimine

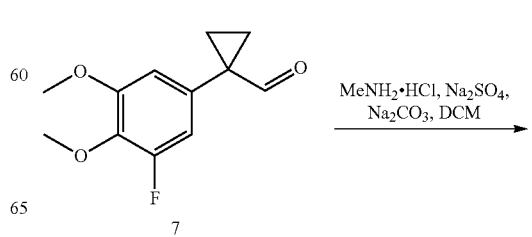

-continued

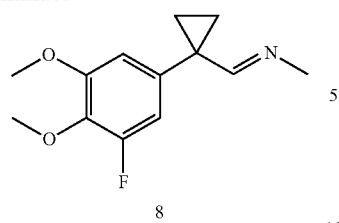
8

A mixture of 1-(3-fluoro-4,5-dimethoxy-phenyl)cyclopropanecarbaldehyde (3.70 g, 16.5 mmol), methanamine; hydrochloride (5.57 g, 82.5 mmol), Na2CO3 (5.25 g, 49.5 mmol) and Na$_2$SO$_4$ (35.10 g, 247 mmol, 25.1 mL) in DCM (40 mL) was degassed and purged with N$_2$ for 3 times, and th en the mixture was stirred at 25° C. for 16 hours under N$_2$ atmosphere. On completion, the reaction mixture was filtered, concentrated in vacuo to give (E)-1-[1-(3-bromo-4,5-dimethoxy-phenyl) cyclopropyl]-N-methyl-methanimine (4.45 g, 86% yield) as a yellow liquid.

$^1$H NMR (400 MHz, CDCl$_3$) δ=7.61-7.47 (m, 1H), 6.71 (d, J=1.9 Hz, 2H), 3.91-3.86 (m, 6H), 3.25 (d, J=1.5 Hz, 3H), 1.36-1.22 (m, 2H), 1.20-1.11 (m, 2H).

Step 7—4-(3-fluoro-4,5-dimethoxy-phenyl)-1-methyl-2,3-dihydropyrrole

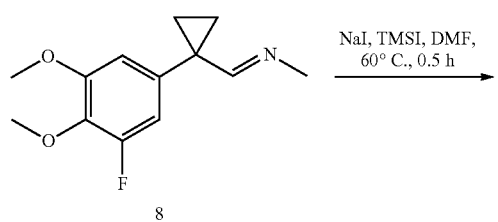

A mixture of (E)-1-[1-(3-fluoro-4,5-dimethoxy-phenyl) cyclopropyl]-N-methyl-methanimine (1.0 0 g, 4.21 mmol,), NaI (63.1 mg, 421. umol), TMSI (843 mg, 4.21 mmol) in DMF (5 mL) was de gassed and purged with N$_2$ for 3 times, and then the mixture was stirred at 60° C. for 0.5 hr under N$_2$ atmosphere. On completion, the reaction mixture was filtered, concentrated in vacuo to give 4-(3-fluoro-4,5-dimethoxy-phenyl)-1-methyl-2,3-dihydropyrrole (1.00 g, crude) as a brown oil.

LC-MS (ESI$^+$) m/z 238.8 (M+H).

Step 8—(3aR,7aS)-3a-(3-fluoro-4,5-dimethoxy-phenyl)-1-methyl-2,3,7,7a-tetrahydroindol-6-one

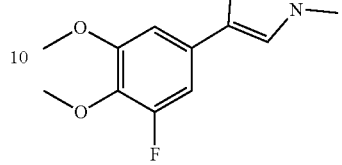 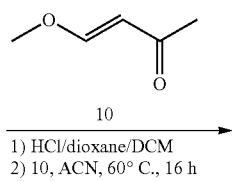

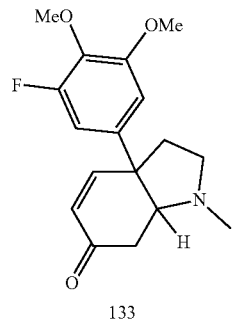 [SMILES: COc1cc(C23C=CC(=O)CC2N(C)CC3)cc(I)c1OC]
133

To a solution of 4-(3-fluoro-4,5-dimethoxy-phenyl)-1-methyl-2,3-dihydropyrrole (1.00 g, 1.14 mmol, 27% purity) in DCM (1 mL) was HCl/dioxane (4 M, 10.0 mL) at 25° C. for 10 mins. After addition, the mixture was concentrated in vacuo to give the residue and then (E)-4-methoxybut-3-en-2-one (227 mg, 2.28 mmol, 228 uL) in ACN (10 mL) was added the residue. The mixture was stirred at 80° C. for 16 hours. On completion, the reaction mixture was filtered, concentrated in vacuo to give the residue. The residue was purified by reverse-phase (0.1% FA) to give crude product. The crude product was purified by prep-HPLC (column: Waters xbridge 150*25 mm 10 um; mobile phase: [water (NH4HCO3)-ACN];B %: 20%-50%,9 min) to give (3aR, 7aS)-3a-(3-fluoro-4,5-dimethoxy-phenyl)-1-methyl-2,3,7, 7a-tetrahydroindol-6-one (9.94 mg, 2.83% yield,) was obtained as a yellow solid.

LC-MS (ESI$^+$) m/z 306.1(M+H)$^+$.

$^1$H NMR (400 MHz, CDCl$_3$) δ=6.67 (dd, J=2.2, 12.8 Hz, 1H), 6.63-6.59 (m, 1H), 6.58 (d, J=1.6 Hz, 1H), 6.05 (d, J=10.4 Hz, 1H), 3.86 (s, 3H), 3.81 (s, 3H), 3.24 (dt, J=2.4, 8.8 Hz, 1H), 2.61-2.56 (m, 1H), 2.56-2.47 (m, 1H), 2.46-2.40 (m, 2H), 2.38-2.30 (m, 1H), 2.25 (s, 3H), 2.19-2.08 (m, 1H).

Example 4—2,3-dimethoxy-5-(1-methyl-6-oxo-2,3,7,7a-tetrahydroindol-3a-yl)benzonitrile (140)

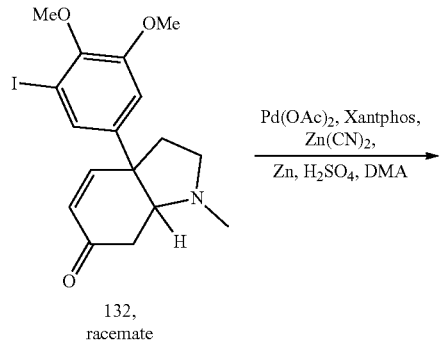

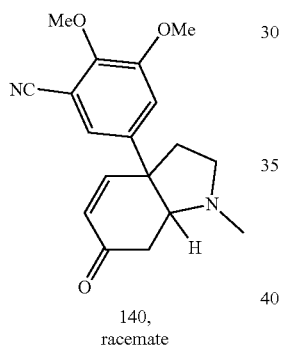

To a solution of 3a-(3-iodo-4,5-dimethoxy-phenyl)-1-methyl-2,3,7,7a-tetrahydroindol-6-one (400 mg, 968 umol), Zn(CN)₂ (182 mg, 1.55 mmol, 98.3 uL) in DMA (5.0 mL) was added Zn (50.6 mg, 774 umol), Xantphos (448 mg, 774 umol) then add Pd(OAc)₂ (17.3 mg, 77.4 umol) and H2SO4 (75.9 mg, 774 umol, 41.2 uL) to the mixture. The mixture was stirred at 80° C. for 2 hours. The mixture was poured to the NaHCO₃ (100 mL) and extracted with ethyl acetate (50 mL). The organic layer was dried by sodium sulfate, filtered and concentrated in vacuo to give the residue. The residue was purified by prep-HPLC (column: Welch Xtimate C18 150*25 mm*5 um;mobile phase: [water(ammonia hydroxide v/v)-ACN]; B %: 21%-51%,2 min) to give the 5-[(3aR,7aS)-1-methyl-6-oxo-2,3,7,7a-tetrahydroindol-3a-yl]-2,3-dimethoxy-benzonitrile (50 mg, 24% yield) was obtained as a white solid.

LC-MS (ESI⁺) m/z 313.2 (M+H)⁺.

¹H NMR (400 MHz, CDCl₃) δ 7.15 (d, J=2.4 Hz, 1H), 7.08 (d, J=2.0 Hz, 1H), 6.73-6.66 (m, 1H), 6.17 (d, J=10 Hz, 1H), 4.05 (s, 3H), 3.92 (s, 3H), 3.42-3.30 (m, 1H), 2.68-2.65 (m, 1H), 2.63-2.52 (m, 2H), 2.49-2.39 (m, 2H), 2.35 (s, 3H), 2.31-2.21 (m, 1H).

Example 5-(3aR,7aS)-3a-(3-cyclopropyl-4,5-dimethoxy-phenyl)-1-methyl-2,3,7,7a-tetrahydroindol-6-one (142)

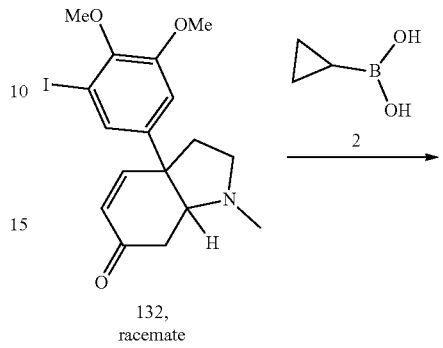 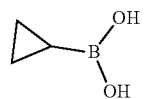

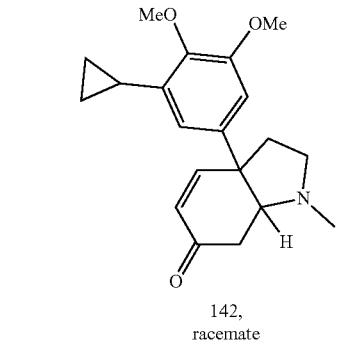

To a solution of (3aR,7aS)-3a-(3-iodo-4,5-dimethoxy-phenyl)-1-methyl-2,3,7,7a-tetrahydroindol-6-one (150 mg, 363 umol) and cyclopropylboronic acid (155 mg, 1.81 mmol) in Tol. (3.0 mL) and H₂O (1.0 mL) was added Na2CO3 (115 mg, 1.09 mmol) and Pd(PPh₃)₄(41.9 mg, 36.3 umol). The mixture was stirred at 90° C. for 12 hours. The mixture was poured to the water (50 mL) and extracted with ethyl acetate (30 mL). The organic layers was dried by sodium sulfate, filtered and concentrated in vacuo to give the residue. The crude product was purified by reversed-phase HPLC(0.1% FA condition) to give the (3aR,7aS)-3a-(3-cyclopropyl-4,5-dimethoxy-phenyl)-1-methyl-2,3,7,7a-tetrahydroindol-6-one (70 mg, 57% yield) was obtained as a colorless gum.

LC-MS (ESI⁺) m/z 328.2 (M+H)⁺.

¹H NMR (400 MHz, CDCl₃) δ 6.77-6.68 (m, 2H), 6.39 (s, 1H), 6.18 (d, J=10.4 Hz, 1H), 3.88 (s, 6H), 3.48-3.32 (m, 1H), 2.94 (br s, 1H), 2.77-2.68 (m, 1H), 2.65 (br s, 1H), 2.59-2.49 (m, 2H), 2.44 (s, 3H), 2.29-2.20 (m, 2H), 1.01 (br d, J=8.4 Hz, 2H), 0.72-0.58 (m, 2H).

Example 5—1-methyl-3a-(3,4,5-trimethoxyphenyl)-2,3,7,7a-tetrahydroindol-6-one (144)

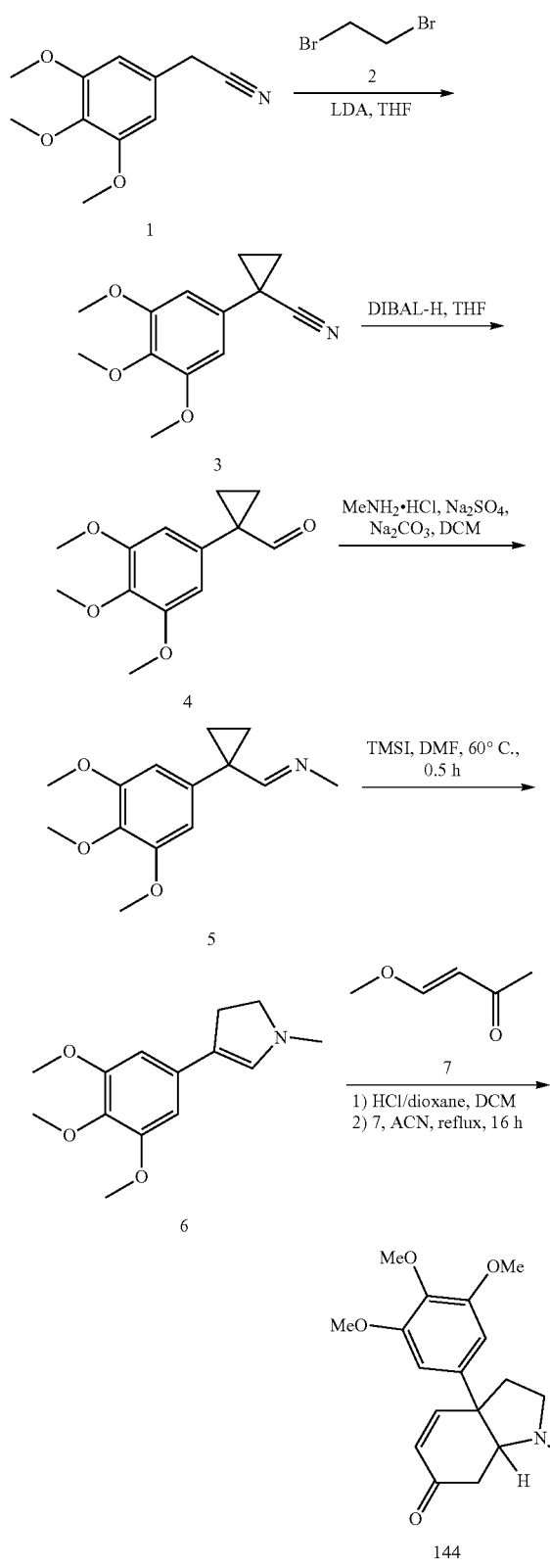

Step 1
1-(3,4,5-trimethoxyphenyl)cyclopropanecarbonitrile
(3)

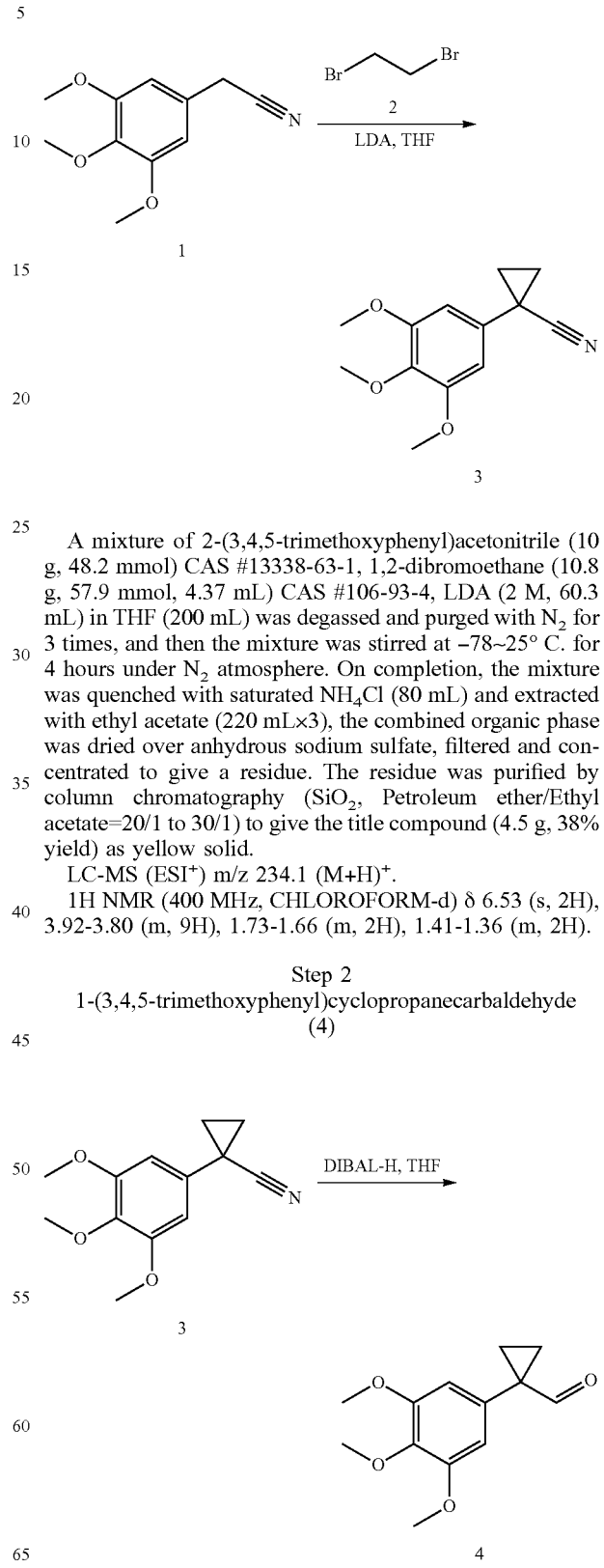

A mixture of 2-(3,4,5-trimethoxyphenyl)acetonitrile (10 g, 48.2 mmol) CAS #13338-63-1, 1,2-dibromoethane (10.8 g, 57.9 mmol, 4.37 mL) CAS #106-93-4, LDA (2 M, 60.3 mL) in THF (200 mL) was degassed and purged with $N_2$ for 3 times, and then the mixture was stirred at −78~25° C. for 4 hours under $N_2$ atmosphere. On completion, the mixture was quenched with saturated $NH_4Cl$ (80 mL) and extracted with ethyl acetate (220 mL×3), the combined organic phase was dried over anhydrous sodium sulfate, filtered and concentrated to give a residue. The residue was purified by column chromatography ($SiO_2$, Petroleum ether/Ethyl acetate=20/1 to 30/1) to give the title compound (4.5 g, 38% yield) as yellow solid.

LC-MS (ESI$^+$) m/z 234.1 (M+H)$^+$.

1H NMR (400 MHz, CHLOROFORM-d) δ 6.53 (s, 2H), 3.92-3.80 (m, 9H), 1.73-1.66 (m, 2H), 1.41-1.36 (m, 2H).

Step 2
1-(3,4,5-trimethoxyphenyl)cyclopropanecarbaldehyde
(4)

A mixture of 1-(3,4,5-trimethoxyphenyl) cyclopropanecarbonitrile (4.5 g, 19.3 mmol), DIBAL-H (1 M, 28.9 mL) in THF (50 mL) was degassed and purged with $N_2$ for 3 times, and then the mixture was stirred at −78-25° C. for 8 hours under $N_2$ atmosphere. On completion, the reaction was cautiously quenched by addition of 2 M HCl and organic components were extracted into ethyl acetate (3×65 mL). The combined extracts were washed with water (2×20 mL), brine (2×20 mL) and then dried ($Na_2SO_4$) filtered and concentrated under reduced pressure to give the residue. The residue was purified by column chromatography ($SiO_2$, Petroleum ether/Ethyl acetate=5/1 to 5/1) to give the title compound (3.7 g, 79% yield) as yellow solid.

LC-MS (ESI$^+$) m/z 236.8 (M+H)+.

$^1$H NMR (400 MHz, CHLOROFORM-d) δ 9.28 (s, 1H), 6.53 (s, 2H), 3.94-3.78 (m, 9H), 1.60-1.54 (m, 3H), 1.44-1.37 (m, 2H).

Step 3 (E)-N-methyl-1-[1-(3,4,5-trimethoxyphenyl) cyclopropyl]methanimine (5)

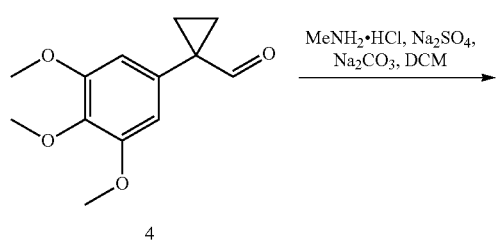

A mixture of 1-(3,4,5-trimethoxyphenyl)cyclopropanecarbaldehyde (3.7 g, 15.6 mmol), $Na_2SO_4$ (33.4 g, 235 mmol, 23.8 mL), methanamine;hydrochloride (5.29 g, 78.3 mmol) and $Na_2CO_3$ (6.64 g, 62.6 mmol) in DCM (250 mL) was degassed and purged with $N_2$ for 3 times, and then the mixture was stirred at 25° C. for 24 hours under $N_2$ atmosphere. On completion, the reaction liquid was dried with a rotary evaporator after filtering. The crude compound was used into the next step without further purification to give the title compound (2.7 g, 90% yield) as yellow solid.

LC-MS (ESI$^+$) m/z 249.9 (M+H)+.

$^1$H NMR (400 MHz, CHLOROFORM-d) δ 7.59 (d, J=1.2 Hz, 1H), 6.56 (s, 2H), 3.97-3.74 (m, 9H), 3.26 (d, J=1.2 Hz, 3H), 1.31-1.26 (m, 2H), 1.19-1.14 (m, 2H).

Step 4 1-methyl-4-(3,4,5-trimethoxyphenyl)-2,3-dihydropyrrole (6)

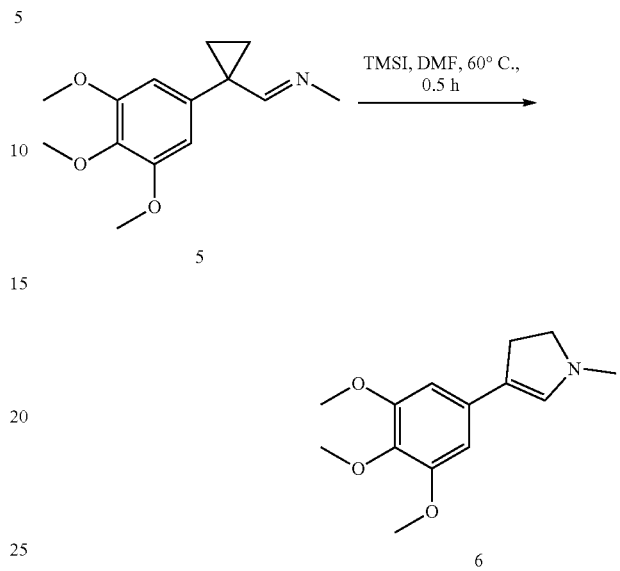

A mixture of (E)-N-methyl-1-[1-(3,4,5-trimethoxyphenyl) cyclopropyl]methanimine (2 g, 8.0 mmol), TMSI (1.61 g, 8.0 mmol, 1.09 mL) in DMF (15 mL) was degassed and purged with $N_2$ for 3 times, and then the mixture was stirred at 60° C. for 0.5 hours under $N_2$ atmosphere. On completion, the mixture was quenched with $H_2O$ (18 mL) and extracted with ethyl acetate (20 mL×3), the combined organic phase was dried over anhydrous sodium sulfate, filtered and concentrated to give a residue. Then the aqueous phase was adjusted pH with saturated $NaHCO_3$ (8 mL) to 8 and extracted with ethyl acetate (20 mL×3), the combined organic phase was dried over anhydrous sodium sulfate, filtered and concentrated to give a residue. The crude compound was used into the next step without further purification to give the title compound (1 g, 30% yield) as yellow oil.

LC-MS (ESI$^+$) m/z 250.0 (M+H)+.

$^1$H NMR (400 MHz, CHLOROFORM-d) δ 8.03 (s, 1H), 6.47-6.40 (m, 2H), 6.37 (Br d, J=1.2 Hz, 1H), 3.90-3.80 (m, 9H), 3.17 (Br t, J=9.2 Hz, 2H), 2.67 (s, 2H).

Step 5 1-methyl-3a-(3,4,5-trimethoxyphenyl)-2,3,7,7a-tetrahydroindol-6-one (144)

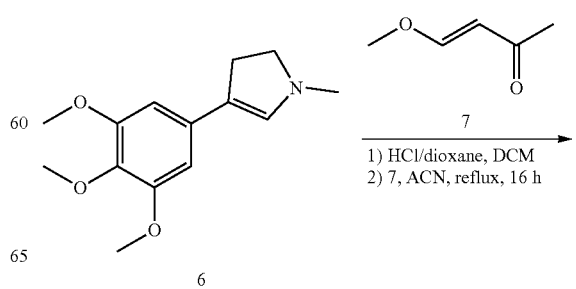

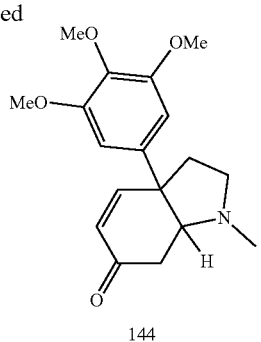

144

A mixture of 1-methyl-4-(3,4,5-trimethoxyphenyl)-2,3-dihydropyrrole (1 g, 4.0 mmol), (E)-4-methoxybut-3-en-2-one (401 mg, 4.0 mmol, 402.79 uL), HCl/dioxane (4 M, 3 mL) and ACN (6.24 g, 152 mmol, 8 mL) in DCM (9 mL) was degassed and purged with N₂ for 3 times, and then the mixture was stirred at 90° C. for 12 hours under N₂ atmosphere. On completion, the reaction was filtered. The residue was purified by prep-HPLC (basic condition:column: Welch Xtimate C18 150*25 mm*5 um;mobile phase: [water(NH₃H₂O)-ACN];B %: 18%-48%,8 min) to give the title compound (570 mg, 45% yield) as white solid.

LC-MS (ESI+) m/z 317.9 (M+H)⁺.

¹H NMR (400 MHz, CHLOROFORM-d) δ 6.62 (dd, J=2.0, 10.1 Hz, 1H), 6.45 (s, 2H), 6.02 (d, J=10.0 Hz, 1H), 3.84-3.69 (m, 9H), 3.29-3.17 (m, 1H), 2.58 (br s, 1H), 2.50-2.43 (m, 2H), 2.42-2.32 (m, 2H), 2.23 (s, 3H), 2.12 (td, J=8.4, 13.0 Hz, 1H).

Example 6—Compounds 145, 188, and 189

Step 1 1-methyl-3a-(3,4,5-trimethoxyphenyl)-2,3,4,5,7,7a-hexahydroindol-6-one (145)

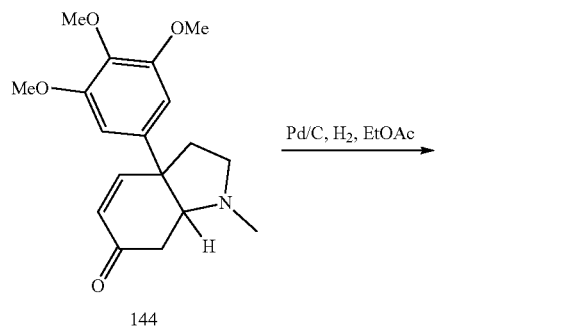

144

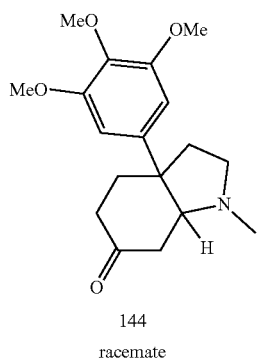

144
racemate

A mixture of 1-methyl-3a-(3,4,5-trimethoxyphenyl)-2,3,7,7a-tetrahydroindol-6-one (190 mg, 598 umol) and Pd/C (10.0 mg, 59.9 umol, 10% purity) in EtOAc (4 mL) was degassed and purged with H₂ for 3 times, and then the mixture was stirred at 25° C. for 12 hours under H₂ atmosphere. On completion, the reaction was filtered. The residue was purified by prep-HPLC (basic condition: column: Welch Xtimate C18 150*25 mm*5 um; mobile phase: [water(ammonia hydroxide v/v)-ACN];B %: 21%-51%, 2 min) to give the title compound (232 mg, 90% yield) as yellow solid.

LC-MS (ESI+) m/z 320.2 (M+H)⁺.

¹H NMR (400 MHz, CDCl₃) δ 6.60 (s, 2H), 3.95-3.81 (m, 9H), 3.18-3.11 (m, 1H), 2.95 (t, J=3.2 Hz, 1H), 2.62 (d, J=3.6 Hz, 2H), 2.52-2.41 (m, 1H), 2.38-2.29 (m, 4H), 2.25 (s, 1H), 2.23-2.19 (m, 2H), 2.18-2.10 (m, 2H).

Step 2 (3aS,7aS)-1-methyl-3a-(3,4,5-trimethoxyphenyl)-2,3,4,5,7,7a-hexahydroindol-6-one (188) and (3aR,7aR)-1-methyl-3a-(3,4,5-trimethoxyphenyl)-2,3,4,5,7,7a-hexahydroindol-6-one (189)

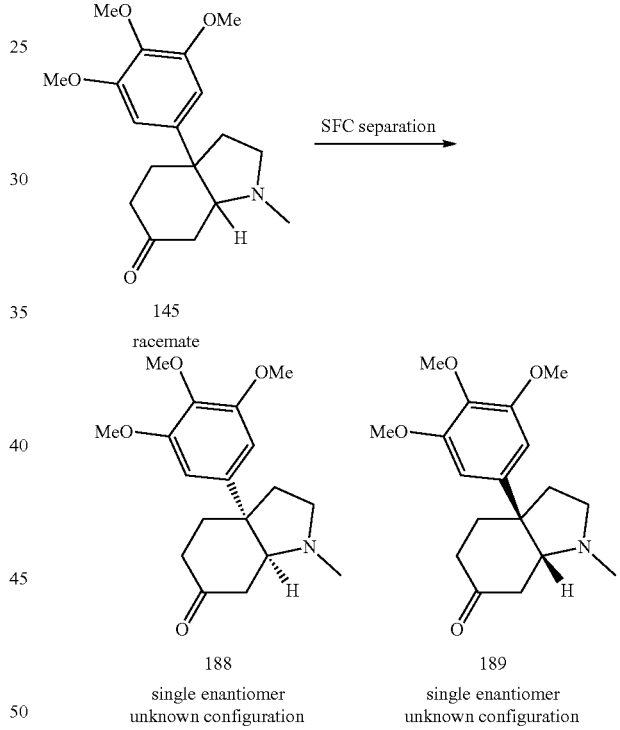

The residue was separated by SFC (condition: column: Daicel ChiralPak IG (250*30 mm, 10 um);mobile phase: [Neu-MeOH];B %: 25%-25%,C14.55;146 min) to give the (3aS,7aS)-1-methyl-3a-(3,4,5-trimethoxyphenyl)-2,3,4,5,7,7a-hexahydroindol-6-one(100 mg, 45% yield) as white solid and to give (3aR,7aR)-1-methyl-3a-(3,4,5-trimethoxyphenyl)-2,3,4,5,7,7a hexahydroindol-6-one (95.0 mg, 43% yield) as yellow solid.

189

LC-MS (ESI+) m/z 320.1 (M+H)+.

¹H NMR (400 MHz, CDCl₃) 6.59 (s, 2H), 3.96-3.80 (m, 9H), 3.20-3.10 (m, 1H), 2.95 (Br s, 1H), 2.62 (Br d, J=3.2 Hz, 2H), 2.33 (s, 3H), 2.25 (s, 1H), 2.23-2.19 (m, 2H), 2.18-2.10 (m, 2H), 1.58 (s, 2H).

188

LC-MS (ESI+) m/z 320.3 (M+H)+.

¹H NMR (400 MHz, CDCl₃) δ 6.59 (s, 2H), 3.96-3.80 (m, 9H), 3.16 (t, J=6.8 Hz, 1H), 2.96 (s, 1H), 2.63 (s, 2H), 2.34 (s, 3H), 2.24 (s, 1H), 2.23-2.19 (m, 2H), 2.18-2.09 (m, 2H), 1.57 (s, 2H).

Example 7-3a-(3-fluoro-4,5-dimethoxy-phenyl)-1-methyl-2,3,4,5,7,7a-hexahydroindol-6-one (134)

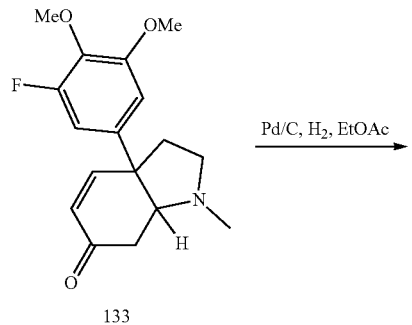

133

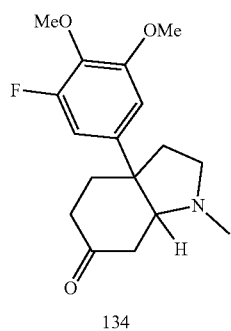

134

A mixture of 3a-(3-fluoro-4,5-dimethoxy-phenyl)-1-methyl-2,3,7,7a-tetrahydroindol-6-one (70.00 mg, 229 umol), Pd/C (10 mg, 10% purity) in EA (2 mL) was degassed and purged with N₂ for 3 times, and then the mixture was stirred at 25° C. for 1 hr under H₂ atmosphere. On completion, the reaction mixture was filtered, concentrated in vacuo to give the residue, the residue was purified by prep-HPLC (column: Welch Xtimate C18 150*25 mm*5 um;mobile phase: [water(NH₃H₂O)-ACN];B %: 30%-60%,8 min) to give 3a-(3-fluoro-4,5-dimethoxy-phenyl)-1-methyl-2,3,4,5,7,7a-hexahydroindol-6-one (20 mg, 61.8 umol, 26% yield, 95% purity) as a white solid.

LC-MS (ESI⁺) m/z 308.2 (M+H)⁺

¹H NMR (400 MHz, CDCl₃) δ=6.83-6.67 (m, 1H), 6.62 (s, 1H) 4.07-3.69 (m, 6H), 3.15-2.95 (m, 1H), 2.91-2.80 (m, 1H), 2.52 (d, J=2.8 Hz, 2H), 2.45-2.33 (m, 1H), 2.31-2.21 (m, 4H), 2.18-1.93 (m, 5H).

Example 8—(3aS,7aS)-3a-(3-fluoro-4,5-dimethoxy-phenyl)-1,7a-dimethyl-3,4,5,7-tetrahydro-2H-indol-6-one (194) and (3aR,7aR)-3a-(3-fluoro-4,5-dimethoxy-phenyl)-1,7a-dimethyl-3,4,5,7-tetrahydro-2H-indol-6-one (195)

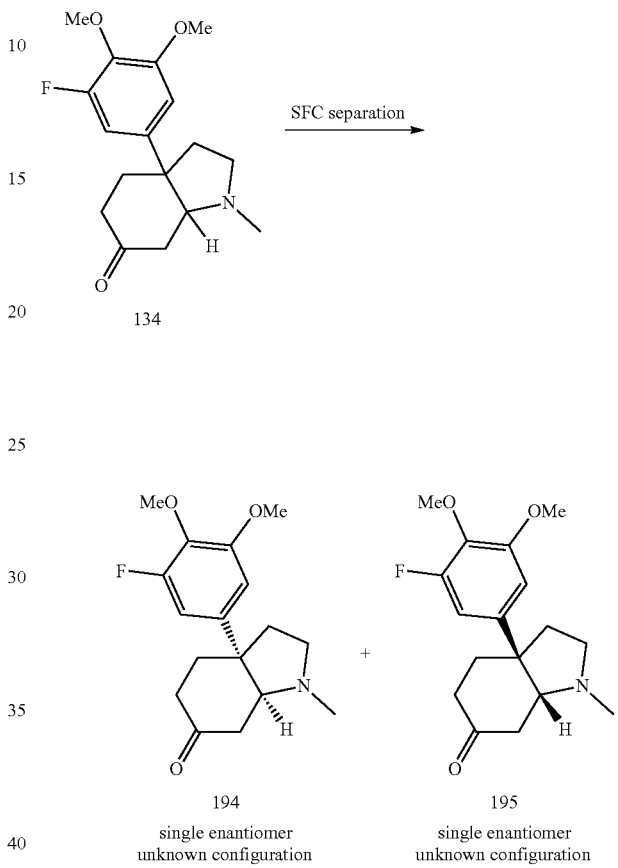

194
single enantiomer
unknown configuration 195
single enantiomer
unknown configuration The 3a-(3-fluoro-4,5-dimethoxy-phenyl)-1-methyl-2,3,4,5,7,7a-hexahydroindol-6-one was purification by SFC (column: Daicel ChiralPak IG (250*30 mm, 10 um);mobile phase: [0.1% NH₃H₂O MeOH];B %: 20%-20%,C12.05;109 min) to give (3aS,7aS)-3a-(3-fluoro-4,5-dimethoxy-phenyl)-1,7a-dimethyl-3,4,5,7-tetrahydro-2H-indol-6-one (4.09 mg, 18% yield, 97% purity) as a white solid & (3aR,7aR)-3a-(3-fluoro-4,5-dimethoxy-phenyl)-1,7a-dimethyl-3,4,5,7-tetrahydro-2H-indol-6-one (4.92 mg, 22% yield, 94% purity) as a white solid.

194

LC-MS (ESI⁺) m/z 308.2 (M+H)⁺.

¹H NMR (400 MHz, CDCl₃) δ=6.77 (br d, J=12.8 Hz, 1H), 6.70 (s, 1H), 3.92 (br d, J=13.6 Hz, 6H), 3.14 (t, J=6.4 Hz, 1H), 2.90 (s, 1H), 2.70-2.53 (m, 2H), 2.52-2.40 (m, 1H), 2.38-2.27 (m, 4H), 2.26-2.13 (m, 3H), 2.13-2.06 (m, 2H).

195

LC-MS (ESI⁺) m/z 308.2 (M+H)⁺.

¹H NMR (400 MHz, CDCl₃) δ=6.77 (br d, J=12.8 Hz, 1H), 6.70 (s, 1H), 3.92 (br d, J=13.6 Hz, 6H), 3.14 (t, J=6.4 Hz, 1H), 2.90 (s, 1H), 2.70-2.53 (m, 2H), 2.52-2.40 (m, 1H), 2.38-2.27 (m, 4H), 2.26-2.13 (m, 3H), 2.13-2.06 (m, 2H).

Example 9—3a-(3-bromo-4,5-dimethoxy-phenyl)-1-methyl-2,3,4,5,7,7a-hexahydroindol-6-one (129)

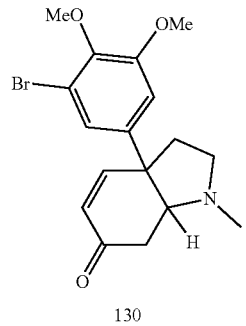

130

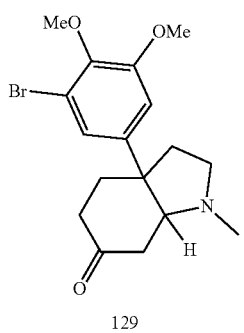

129

A mixture of 3a-(3-bromo-4,5-dimethoxy-phenyl)-1-methyl-2,3,7,7a-tetrahydroindol-6-one (10.0 mg, 27.3 umol), Pt/V/C (10 mg, 2.73 umol), H₂ (55.15 ug, 27.30 umol,) in EtOAc (1 mL) was de gassed and purged with H₂ for 3 times, and then the mixture was stirred at 25° C. for 2 hours und er H₂ atmosphere. On completion, The residue was purified by prep-HPLC (column: Phenomenex×C18 150*25 mm*10 um; mobile phase: [water(NH₄HCO₃)-ACN];B %: 33%-63%,8 min) to give 3a-(3-bromo-4,5-dimethoxy-phenyl)-1-methyl-2,3,4,5,7,7a-hexahydroindol-6-one (20 mg, 30% yield,) as a white solid.

LC-MS (ESI⁺) m/z 368.0 (M+H)⁺.

Example 10 (3aS,7aS)-3a-(3-bromo-4,5-dimethoxy-phenyl)-1-methyl-2,3,4,5,7,7a-hexahydroin dol-6-one (226) and (3aR,7aR)-3a-(3-bromo-4,5-dimethoxy-phenyl)-1-methyl-2,3,4,5,7,7a-hex ahydroindol-6-one (227)

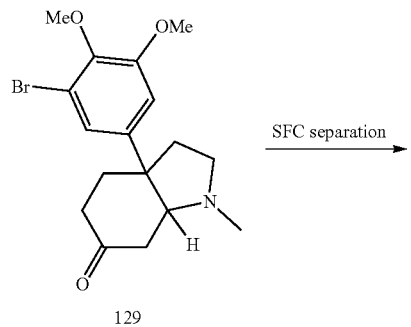

129

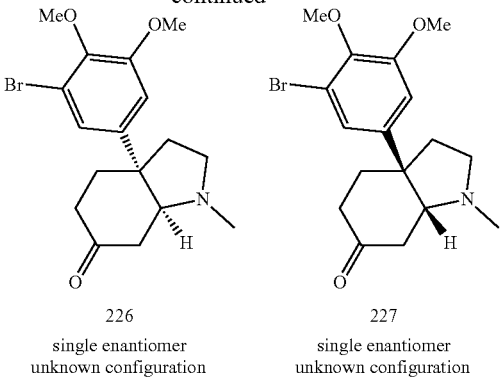

226
single enantiomer
unknown configuration 227
single enantiomer
unknown configuration 10-[(2S,3S)-3-[(3'aS,4R,7'aS)-3'a-(3,4-dimethoxyphenyl)-1'-methyl-spiro[1,3-dioxolane-2,6'-2,3,4,5,7,7a-hexahydroindole]-4-yl]-2,3-dihydroxy-propyl]-7,8-dimethyl-benzo[g]pteridine-2,4-dione was separated by SFC (column: DAICEL CHIRALPAK IE (250 mm*30 mm,10 um); mobile phase: [Neu-EtOH];B %: 20%-20%,C20;80 min) to give (3aS,7aS)-3a-(3-bromo-4,5-dimethoxy-phenyl)-1-methyl-2,3,4,5,7,7a-hexahydroindol-6-one (6.18 mg, 29% yield) as a yellow gum and (3aR,7aR)-3a-(3-bromo-4,5-dimethoxy-phenyl)-1-methyl-2,3,4,5,7,7a-hexahydroindol-6-one (5.49 mg, 26% yield) as a yellow gum. 226:

LC-MS (ESI⁺) m/z 368.0 (M+H)⁺

¹H NMR (400 MHz, CDCl₃) δ=7.07 (d, J=2.0 Hz, 1H), 6.78 (d, J=2.0 Hz, 1H), 3.80 (d, J=11.3 Hz, 6H), 3.18-3.01 (m, 1H), 2.85 (s, 1H), 2.53 (s, 2H), 2.46-2.33 (m, 1H), 2.30-2.21 (m, 4H), 2.20-2.15 (m, 1H), 2.15-2.07 (m, 2H), 2.06-1.97 (m, 2H), 1.97-1.97 (m, 1H), 1.87-1.33 (m, 2H).

227:

LC-MS (ESI⁺) m/z 368.0 (M+H)⁺

¹H NMR (400 MHz, CDCl₃) δ=7.07 (d, J=2.4 Hz, 1H), 6.78 (d, J=2.0 Hz, 1H), 3.80 (d, J=11.2 Hz, 6H), 3.15-3.02 (m, 1H), 2.85 (t, J=3.2 Hz, 1H), 2.53 (d, J=3.6 Hz, 2H), 2.45-2.32 (m, 1H), 2.30-2.21 (m, 4H), 2.16 (s, 1H), 2.15-2.07 (m, 2H), 2.06-1.96 (m, 2H).

Example 11—3a-(3-iodo-4,5-dimethoxy-phenyl)-1-methyl-2,3,4,5,7,7a-hexahydroindol-6-one (131)

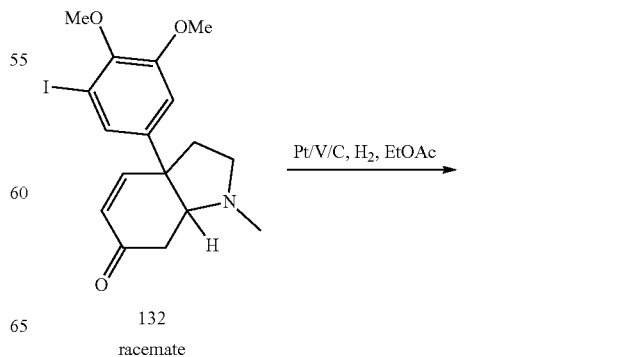

132
racemate

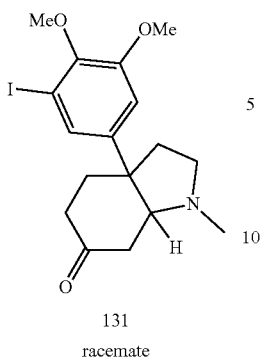

131
racemate

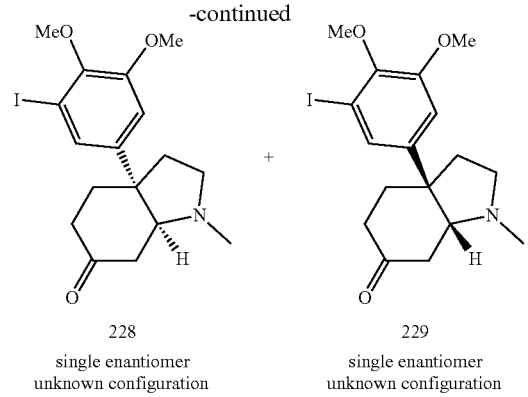

228
single enantiomer
unknown configuration 229
single enantiomer
unknown configuration A mixture of 3a-(3-iodo-4,5-dimethoxy-phenyl)-1-methyl-2,3,7,7a-tetrahydroindol-6-one (200 mg, 241 umol), Pt/V/C (20 mg, 10% purity) in EA (1.0 mL) was degassed and purged with $H_2$ for 3 times, and then the mixture was stirred at 25° C. for 4 hours under $H_2$ atmosphere. On completion, the combined reaction mixture was filtered, concentrated in vacuo to give the residue. The combined reaction mixture was purified by prep-HPLC (basic condition: column: Welch Xtimate C18 150*25 mm*5 um; mobile phase: [water($NH_3H_2O$)-ACN];B %: 40%-70%,8 min) to give 3a-(3-iodo-4,5-dimethoxy-phenyl)-1-methyl-2, 3,4,5,7, 7a-hexahydroindol-6-one (100 mg, 49% yield) as a solid.

LC-MS (ESI$^+$) m/z 415.9 (M+H)$^+$;

$^1$H NMR (400 MHz, CDCl$_3$) δ 7.37 (d, J=2.0 Hz, 1H), 6.90 (d, J=2.0 Hz, 1H), 3.88 (d, J=16.0 Hz, 6H), 3.21-3.08 (m, 1H), 2.93 (s, 1H), 2.61 (d, J=3.2 Hz, 2H), 2.53-2.42 (m, 1H), 2.39-2.29 (m, 4H), 2.28-2.23 (m, 1H), 2.23-2.15 (m, 2H), 2.15-2.06 (m, 2H).

Example 12—(3aS,7aS)-3a-(3-iodo-4,5-dimethoxy-phenyl)-1-methyl-2,3,4,5,7,7a-hexahydroindol-6-one (228)&(3aR,7aR)-3a-(3-iodo-4,5-dimethoxy-phenyl)-1-methyl-2,3,4,5,7,7a-hexahydroindol-6-one (229)

3a-(3-iodo-4,5-dimethoxy-phenyl)-1-methyl-2, 3,4,5,7, 7a-hexahydroindol-6-one (100 mg) was separated by SFC (column: DAICEL CHIRALCEL OD(250 mm*30 mm,10 um);mobile phase: [Neu-MeOH];B %: 25%-25%,A2.2;22 min) to give (3aS,7aS)-3a-(3-iodo-4,5-dimethoxy-phenyl)-1-methyl-2,3,4,5,7,7a-hexahydroindol-6-one (38.5 mg, 38% yield) as a yellow gum and (3aR,7aR)-3a-(3-iodo-4,5-dimethoxy-phenyl)-1-methyl-2,3,4,5,7,7a-hexahydroindol-6-one (43.52 mg, 43% yield) as a yellow gum.

228: LC-MS (ESI$^+$) m/z 416.0 (M+H)$^+$;

$^1$H NMR (400 MHz, CDCl$_3$) δ 7.26 (d, J=2.0 Hz, 1H), 6.80 (d, J=2.0 Hz, 1H), 3.78 (d, J=16.0 Hz, 6H), 3.10 (t, J=6.8 Hz, 1H), 2.88 (s, 1H), 2.62-2.48 (m, 2H), 2.45-2.33 (m, 1H), 2.32-2.23 (m, 4H), 2.21-2.00 (m, 5H).

229: LC-MS (ESI$^+$) m/z 416.0 (M+H)$^+$;

$^1$H NMR (400 MHz, CDCl$_3$) δ 7.35 (d, J=2.0 Hz, 1H), 6.89 (d, J=2.0 Hz, 1H), 3.88 (d, J=16.0 Hz, 6H), 3.25-3.14 (m, 1H), 2.99 (s, 1H), 2.73-2.58 (m, 2H), 2.54-2.43 (m, 1H), 2.38 (s, 4H), 2.30-2.10 (m, 5H).

Example 13—3a-(3-cyclopropyl-4,5-dimethoxy-phenyl)-1-methyl-2,3,4,5,7,7a-hexahydroindol-6-one (143)

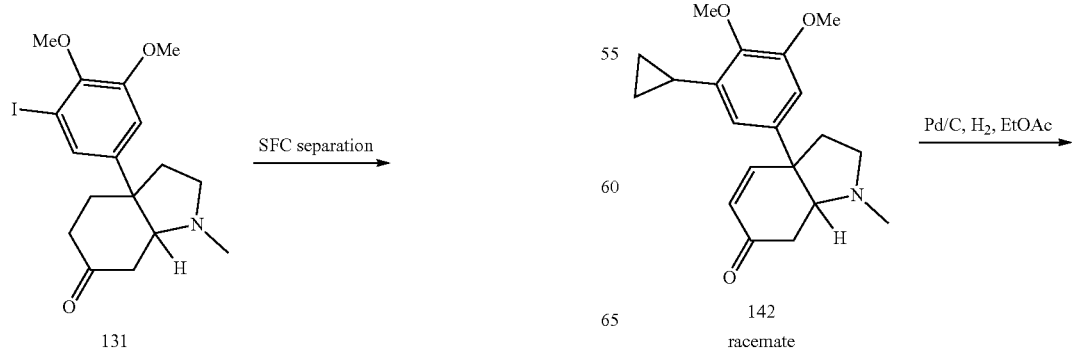

131          142
                 racemate

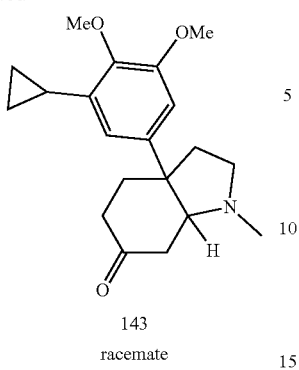

143
racemate

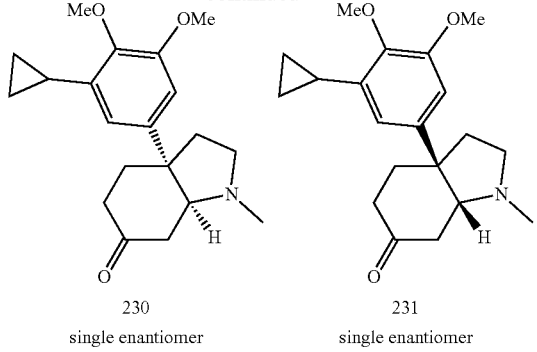

230
single enantiomer
unknown configuration 231
single enantiomer
unknown configuration To a solution of (3aR,7aS)-3a-(3-cyclopropyl-4,5-dimethoxy-phenyl)-1-methyl-2,3,7,7a-tetrahydroindol-6-one (200 mg, 610 umol) in EA (1.0 mL) was added Pd/C (10%, 20 mg) under $N_2$ atmosphere. The suspension was degassed and purged with H2 for 3 times. The mixture was stirred under $H_2$ (15 Psi.) at 25° C. for 2 hours. The reaction mixture was filtered, concentrated in vacuo to give the residue. The residue was purified by prep-HPLC (column: Welch Xtimate C18 150*25 mm*5 um;mobile phase: [water($NH_3H_2O$)-ACN];B %: 38%-68%,8 min) to give the 3a-(3-cyclopropyl-4,5-dimethoxy-phenyl)-1-methyl-2,3,4,5,7,7a-hexahydroindol-6-one (80 mg, 39% yield) as a yellow solid.

LC-MS (ESI$^+$) m/z 330.4 (M+H)$^+$.

$^1$H NMR (400 MHz, CDCl$_3$) δ 6.74 (d, J=2.0 Hz, 1H), 6.42 (d, J=2.0 Hz, 1H), 3.89 (d, J=5.1 Hz, 6H), 3.19-3.10 (m, 1H), 2.93 (br s, 1H), 2.61 (d, J=3.6 Hz, 2H), 2.53-2.37 (m, 2H), 2.33 (s, 3H), 2.31-2.22 (m, 2H), 2.21-2.04 (m, 4H), 1.05-0.96 (m, 2H), 0.72-0.64 (m, 2H)

Example 14—(3aS,7aS)-3a-(3-cyclopropyl-4,5-dimethoxy-phenyl)-1-methyl-2,3,4,5,7,7a-hexahydroindol-6-one(230) and (3aR,7aR)-3a-(3-cyclopropyl-4,5-dimethoxy-phenyl)-1-methyl-2,3,4,5,7,7a-hexahydroindol-6-one (231)

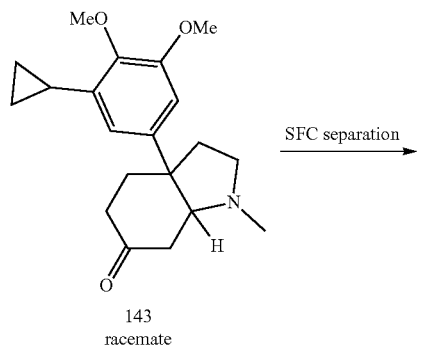

143
racemate

SFC separation →

The 3a-(3-cyclopropyl-4,5-dimethoxy-phenyl)-1-methyl-2,3,4,5,7,7a-hexahydroindol-6-one was separated by SFC (column: DAICEL CHIRALCEL OD(250 mm*30 mm,10 um);mobile phase: [Neu-IPA];B %: 30%-30%,C7.85;71 min) to give the (3aS,7aS)-3a-(3-cyclopropyl-4,5-dimethoxy-phenyl)-1-methyl-2,3,4,5,7,7a-hexahydroindol-6-one (37.4 mg, 45% yield) as a yellow oil and (3aR,7aR)-3a-(3-cyclopropyl-4,5-dimethoxy-phenyl)-1-methyl-2,3,4,5,7,7a-hexahydroindol-6-one (40.2 mg, 49% yield) as a yellow oil. 230

LC-MS (ESI$^+$) m/z 330.2 (M+H)$^+$.

$^1$H NMR (400 MHz, CDCl$_3$) δ 6.74 (d, J=2.0 Hz, 1H), 6.41 (d, J=1.6 Hz, 1H), 3.89 (d, J=5.4 Hz, 6H), 3.22-3.09 (m, 1H), 2.94 (br s, 1H), 2.62 (br s, 2H), 2.51-2.40 (m, 1H), 2.34 (s, 4H), 2.29-2.05 (m, 6H), 1.08-0.95 (m, 2H), 0.74-0.62 (m, 2H). 231

LC-MS (ESI$^+$) m/z 330.2 (M+H)$^+$.

$^1$H NMR (400 MHz, CDCl$_3$) δ=6.65 (d, J=2.4 Hz, 1H), 6.32 (d, J=2.0 Hz, 1H), 3.80 (d, J=5.2 Hz, 6H), 3.06 (br t, J=7.2 Hz, 1H), 2.84 (br s, 1H), 2.52 (br d, J=3.6 Hz, 2H), 2.42-2.30 (m, 1H), 2.29-2.22 (m, 4H), 2.21-1.96 (m, 6H), 0.95-0.88 (m, 2H), 0.62-0.55 (m, 2H).

Example 16—(3aR,7aS)-3a-(3-(benzyloxy)-4-methoxy-2-vinylphenyl)-1-methyl-3,3a,7,7a-tetrahydro-1H-indol-6(2H)-one (239)

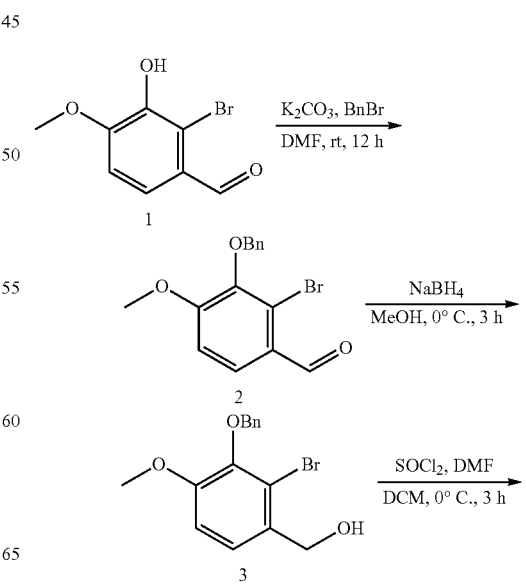

-continued

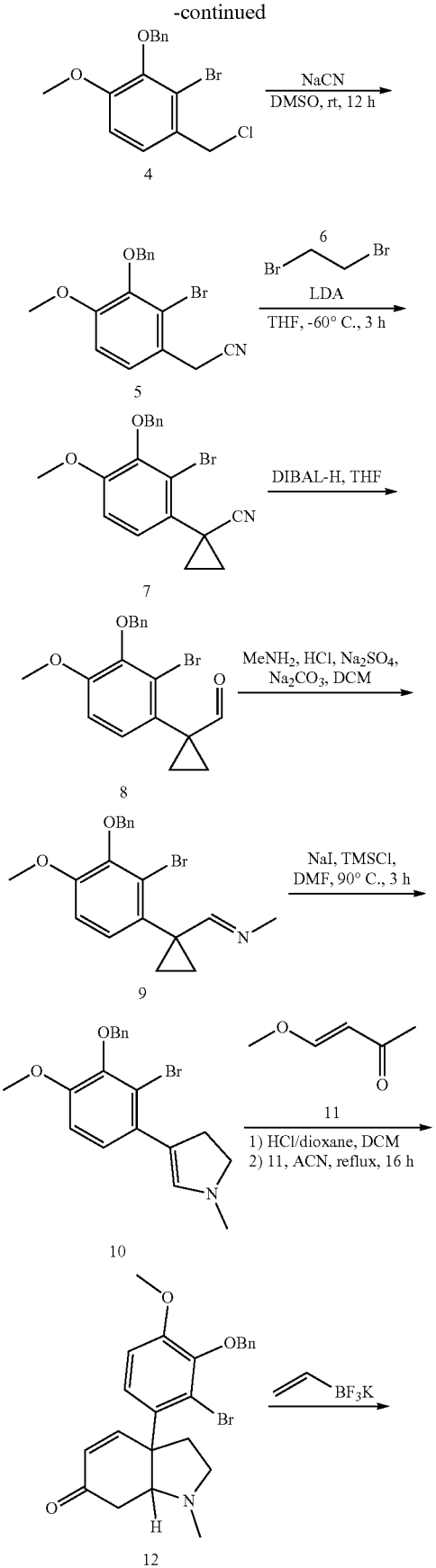

-continued

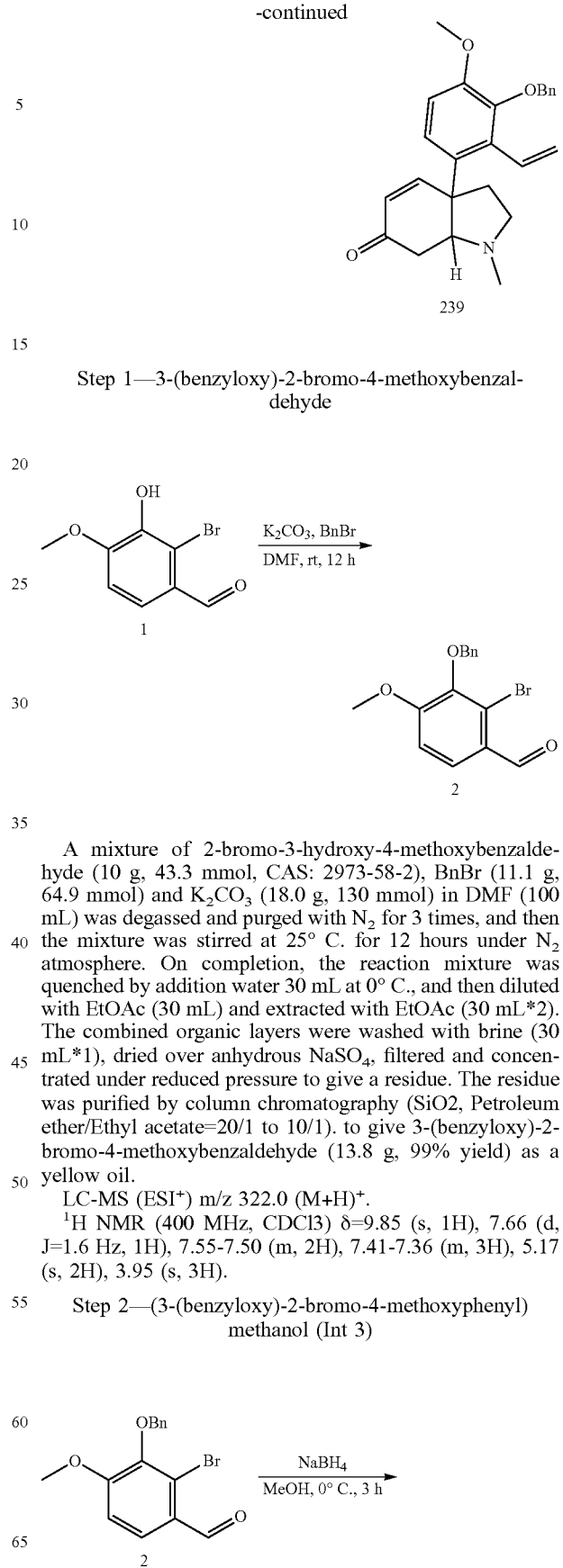

Step 1—3-(benzyloxy)-2-bromo-4-methoxybenzaldehyde

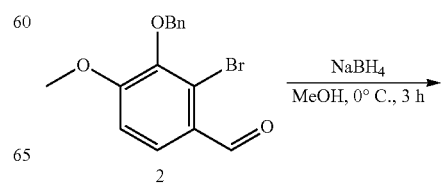

A mixture of 2-bromo-3-hydroxy-4-methoxybenzaldehyde (10 g, 43.3 mmol, CAS: 2973-58-2), BnBr (11.1 g, 64.9 mmol) and $K_2CO_3$ (18.0 g, 130 mmol) in DMF (100 mL) was degassed and purged with $N_2$ for 3 times, and then the mixture was stirred at 25° C. for 12 hours under $N_2$ atmosphere. On completion, the reaction mixture was quenched by addition water 30 mL at 0° C., and then diluted with EtOAc (30 mL) and extracted with EtOAc (30 mL*2). The combined organic layers were washed with brine (30 mL*1), dried over anhydrous $NaSO_4$, filtered and concentrated under reduced pressure to give a residue. The residue was purified by column chromatography (SiO2, Petroleum ether/Ethyl acetate=20/1 to 10/1). to give 3-(benzyloxy)-2-bromo-4-methoxybenzaldehyde (13.8 g, 99% yield) as a yellow oil.

LC-MS (ESI⁺) m/z 322.0 (M+H)⁺.

¹H NMR (400 MHz, CDCl3) δ=9.85 (s, 1H), 7.66 (d, J=1.6 Hz, 1H), 7.55-7.50 (m, 2H), 7.41-7.36 (m, 3H), 5.17 (s, 2H), 3.95 (s, 3H).

Step 2—(3-(benzyloxy)-2-bromo-4-methoxyphenyl)methanol (Int 3)

-continued

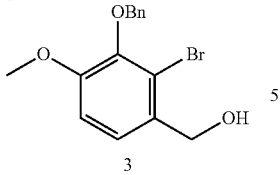

A mixture of 3-(benzyloxy)-2-bromo-4-methoxybenzaldehyde (13.8 g, 43.0 mmol) in MeOH (50 mL) was added NaBH$_4$ (2.44 g, 64.5 mmol) at 0° C., and then the mixture was stirred at 25° C. for 3 hours. On completion, the reaction mixture was concentrated under reduced pressure to give a residue. The residue was purified by column chromatography (SiO$_2$, Petroleum ether/Ethyl acetate=10/1 to 5/1) to give (3-(benzyloxy)-2-bromo-4-methoxyphenyl)methanol (13.8 g, 99.8% yield) as a yellow liquid.

$^1$H NMR (400 MHz, CDCl3) δ=7.56 (d, J=7.2 Hz, 2H), 7.38 (q, J=7.2 Hz, 3H), 7.14 (s, 1H), 6.91 (s, 1H), 5.03 (s, 2H), 4.63 (s, 2H), 3.88 (s, 3H).

Step 3—2-(benzyloxy)-3-bromo-4-(chloromethyl)-1-methoxybenzene

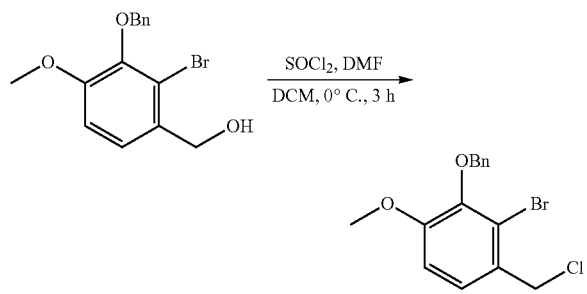

A mixture of (3-(benzyloxy)-2-bromo-4-methoxyphenyl)methanol (13.8 g, 42.7 mmol) in DCM (200 mL) was added a drop DMF and SOCl$_2$ (6.2 mL, 85.4 mmol) at 0° C., and then the mixture was stirred at 25° C. for 3 hours under N$_2$ atmosphere. On completion, the reaction mixture was quenched by addition NH$_4$Cl 100 mL at 0° C., and then diluted with EtOAc 30 mL and extracted with EtOAc 100 mL (100 mL*2). The combined organic layer were washed with brine 30 mL (100 mL*1), dried over anhydrous Na$_2$SO$_4$, filtered and concentrated under reduced pressure to give 2-(benzyloxy)-3-bromo-4-(chloromethyl)-1-methoxybenzene (13.2 g, 90.5% yield) was obtained as a yellow oil.

$^1$H NMR (400 MHz, CDCl3) δ=7.56 (d, J=7.2 Hz, 2H), 7.44-7.33 (m, 3H), 7.19 (d, J=1.6 Hz, 1H), 6.92 (d, J=1.6 Hz, 1H), 5.04 (s, 2H), 4.52 (s, 2H), 3.89 (s, 3H)

Step 4—2-(3-(benzyloxy)-2-bromo-4-methoxyphenyl)acetonitrile

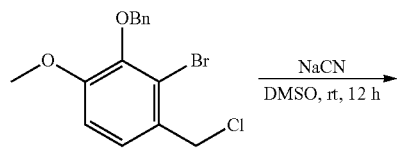

-continued

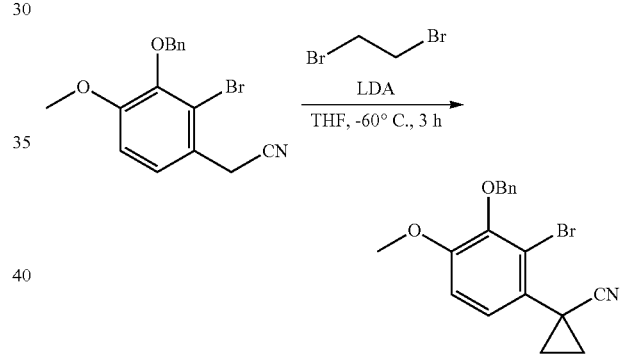

A mixture of 2-(benzyloxy)-3-bromo-4-(chloromethyl)-1-methoxybenzene (13.2 g, 38.6 mmol) in DMSO (200 mL) was added NaCN (3.92 g, 79.98 mmol), and then the mixture was stirred at 25° C. for 12 hours. On completion, the reaction mixture was quenched by addition NH$_4$Cl 100 mL at 0° C., and then diluted with EtOAc 30 mL and extracted with EtOAc 100 mL (100 mL*2). The combined organic layers were washed with brine 30 mL (100 mL*1), dried over anhydrous Na$_2$SO$_4$, filtered and concentrated under reduced pressure to give a 2-(3-(benzyloxy)-2-bromo-4-methoxyphenyl)acetonitrile (13.5 g, 90% yield) was obtained as a yellow liquid.

$^1$H NMR (400 MHz, CDCl3) δ=7.58-7.50 (m, 2H), 7.43-7.34 (m, 3H), 7.13-7.09 (m, 1H), 6.84 (d, J=2.0 Hz, 1H), 5.04 (s, 2H), 3.89 (s, 3H), 3.70 (s, 2H).

Step 5—1-(3-(benzyloxy)-2-bromo-4-methoxyphenyl)cyclopropanecarbonitrile

A mixture of 2-(3-(benzyloxy)-2-bromo-4-methoxyphenyl)acetonitrile (13.5 g, 40.6 mmol) in THF (100 mL) was dropwise LDA (50.8 mL, 2 M, 101.6 mmol) at −60° C., and then the mixture was stirred at same temperature for 0.5 hours. The reaction mixture was added 1,2-dibromoethane (9.16 g, 48.77 mmol, 3.68 mL, 1.2 eq.) at −60° C., and then the mixture was stirred at room temperature for 3 h. The reaction was quenched by methanol/water mixture (1:1, 1000 mL) and the reaction products were extracted into ethyl acetate (3×500 mL). The combined extracts were washed with water (4×500 mL), brine (1×200 mL) and then dried over with anhydrous Na$_2$SO$_4$. The solvent was then removed under reduced pressure to give residue.

The residue was purified by column chromatography (SiO$_2$, Petroleum ether/Ethyl acetate=10/1 to 3/1). to give 1-(3-(benzyloxy)-2-bromo-4-methoxyphenyl)cyclopropanec-arbonitrile (7.6 g, 52.2% yield) was obtained as a white solid.

$^1$H NMR (400 MHz, CDCl3) δ=7.54 (d, J=7.2 Hz, 2H), 7.42-7.31 (m, 3H), 6.97 (d, J=2.0 Hz, 1H), 6.93 (d, J=2.0 Hz, 1H), 5.02 (s, 2H), 3.90 (s, 3H), 1.76-1.69 (m, 2H), 1.43-1.36 (m, 2H).

Step 6—1-(3-(benzyloxy)-2-bromo-4-methoxyphenyl)cyclopropanecarbaldehyde

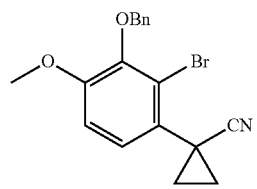

A mixture of 1-(3-(benzyloxy)-2-bromo-4-methoxyphenyl)cyclopropanecarbonitrile(5.7 g, 15.9 mmol) in THF (600 mL) was dropwise DIBAL-H (23.9 mL, 1 M 23.9 mmol) at 0° C., and then the mixture was stirred at 25° C. for 12 hours. The reaction was quenched by 1 M HCl (30 mL) and the reaction products were extracted into ethyl acetate (3×300 mL). The combined extracts were washed with water (4×500 mL), brine (1×200 mL) and then dried over with anhydrous Na$_2$SO4. The solvent was then removed under reduced pressure to give 1-(3-(benzyloxy)-2-bromo-4-methoxyphenyl)cyclopropanecarbaldehyde (6 g, 90% yield) was obtained as a white solid.

$^1$H NMR (400 MHz, CDCl3) δ=9.20 (s, 1H), 7.57 (d, J=7.2 Hz, 2H), 7.43-7.36 (m, 3H), 7.10 (d, J=1.6 Hz, 1H), 6.84 (d, J=1.6 Hz, 1H), 5.04 (s, 2H), 3.88 (s, 3H), 1.60-1.56 (m, 2H), 1.44-1.40 (m, 2H).

Step 7—(E)-N-((1-(3-(benzyloxy)-2-bromo-4-methoxyphenyl)cyclopropyl)methylene) methanamine

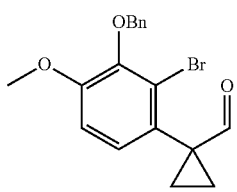

A mixture of 1-(3-(benzyloxy)-2-bromo-4-methoxyphenyl)cyclopropanecarbaldehyde (6 g, 16.6 mmol) in DCM (100 mL) was added methanamine;hydrochloride (5.61 g, 83.05 mmol, 5 eq.), Na$_2$SO$_4$ (35.39 g, 249.15 mmol, 25.28 mL, 15 eq.) and Na$_2$CO$_3$ (5.28 g, 49.83 mmol, 3 eq.). and then the mixture was stirred at room temperature for 12 h. The reaction mixture was filtered and concentrated under reduced pressure to give (E)-N-((1-(3-(benzyloxy)-2-bromo-4-methoxyphenyl)cyclopropyl)methylene)methanamine (6.22 g, 99% yield) was obtained as a yellow oil.

$^1$H NMR (400 MHz, CDCl3) δ=7.60-7.51 (m, 2H), 7.45-7.29 (m, 3H), 7.12 (d, J=2.0 Hz, 1H), 6.84 (d, J=2.0 Hz, 1H), 5.04-5.00 (m, 2H), 3.87 (s, 3H), 3.26 (d, J=1.2 Hz, 2H), 1.32-1.26 (m, 2H), 1.19-1.13 (m, 2H).

Step 8—4-(3-(benzyloxy)-2-bromo-4-methoxyphenyl)-1-methyl-2,3-dihydro-1H-pyrrole

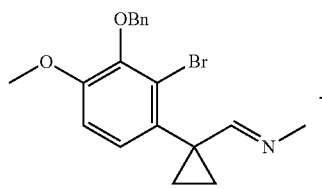

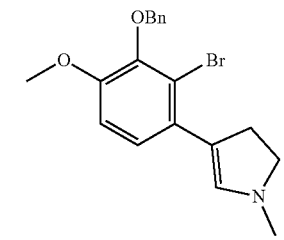

A mixture of (E)-N-((1-(3-(benzyloxy)-2-bromo-4-methoxyphenyl)cyclopropyl)methylene) methanemine (6.22 g, 16.6 mmol) in DMF (100 mL) was added TMSI (3.33 g, 16.62 mmol, 2.26 mL, 1 eq.), and then the mixture was stirred at 60° C. for 0.5 hours. The reaction was quenched by water (30 mL) and the reaction products were extracted into ethyl acetate (3×100 mL). The combined extracts were washed with water (4×100 mL), brine (1×100 mL) and then dried over with anhydrous Na2SO4. The solvent was concentrated under reduced pressure to give 4-(3-(benzyloxy)-2-bromo-4-methoxyphenyl)-1-methyl-2,3-dihydro-1H-pyrrole (1.8 g, 26% yield) was obtained as a yellow oil.

LC-MS (ESI+) m/z 375.0 (M+H)+.

$^1$H NMR (400 MHz, CDCl$_3$) δ=7.59-7.53 (m, 2H), 7.41-7.29 (m, 3H), 6.95 (d, J=2.0 Hz, 1H), 6.70 (d, J=2.0 Hz, 1H), 6.40 (t, J=1.2 Hz, 1H), 4.99 (s, 2H), 3.86 (s, 3H), 3.19 (t, J=9.2 Hz, 2H), 2.80-2.72 (m, 2H).

Steps 9 & 10—4-(3-(benzyloxy)-2-bromo-4-methoxyphenyl)-1-methyl-2,3-dihydro-1H-pyrro-le

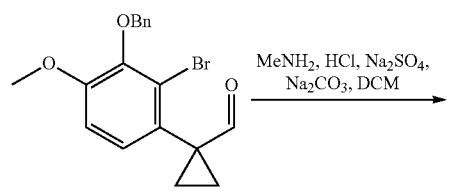

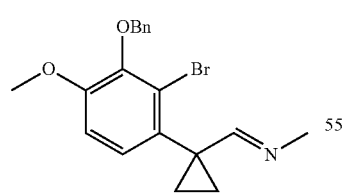

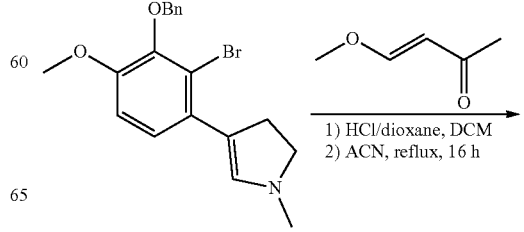

119
-continued

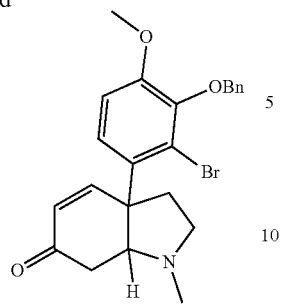

A mixture of A mixture of 4-(3-(benzyloxy)-2-bromo-4-methoxyphenyl)-1-methyl-2,3-dihydro-1H-pyrrole (1.8 g, 4.81 mmol, 1 eq.),HCl/dioxane (4 M, 4.81 mL, 4 eq.) in DCM (10 mL) and then the mixture was stirred at 25° C. for 0.5 hr under $N_2$ atmosphere. The reaction was concentrated under reduced pressure to give residue. The residue was dissolved in ACN (20 mL) was added (E)-4-methoxybut-3-en-2-one (487.50 mg, 4.87 mmol, 488.97 uL, 1 eq.) and then the mixture was stirred at 90° C. for 12 hr under $N_2$ atmosphere. The reaction mixture was quenched by addition NaOH 30 mL at 0° C., and then diluted with EtOAc 30 mL and extracted with EtOAc 30 mL (30 mL*2). The combined organic layers were washed with brine 30 mL (30 mL*1), dried over with anhydrous $Na_2SO_4$, filtered and concentrated under reduced pressure to give a residue. The crude product was purified by reversed-phase HPLC(0.1% TFA condition) to give (3aR,7aS)-3a-(3-(benzyloxy)-2-bromo-4-methoxyphenyl)-1-methyl-3,3a,7,7a-tetrahydro-1H-indol-6(2H)-one (1.3 g, 2.94 mmol, 60.35% yield) as a white solid.

LC-MS (ESI+) m/z 443.7 (M+H)+.

$^1$H NMR (400 MHz, CDCl3) δ=7.56 (d, J=7.2 Hz, 2H), 7.43-7.32 (m, 3H), 7.14 (d, J=2.0 Hz, 1H), 6.91-6.81 (m, 1H), 6.70 (dd, J=1.6, 10.0 Hz, 1H), 6.14 (d, J=10.0 Hz, 1H), 5.08-4.99 (m, 2H), 3.88 (s, 3H), 3.44-3.29 (m, 1H), 3.06 (s, 1H), 2.99-2.83 (m, 2H), 2.72-2.44 (m, 4H), 2.31-2.21 (m, 2H).

Step 11—(3aR,7aS)-3a-(3-(benzyloxy)-4-methoxy-2-vinylphenyl)-1-methyl-3,3a,7,7a-tetrahydro-1H-indol-6(2H)-one (239)

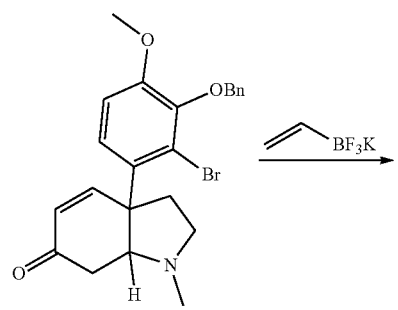

120
-continued

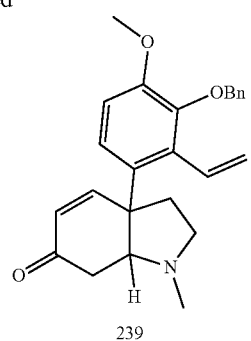
239

A mixture of (3aR,7aS)-3a-(3-(benzyloxy)-2-bromo-4-methoxyphenyl)-1-methyl-3,3a,7,7a-tetrahydro-1H-indol-6(2H)-one (75.00 mg, 169.55 umol, 1 eq.) in in $H_2O$ (2 mL) and THF (0.4 mL) was potassium hydride;trifluoro(vinyl) boron (22.71 mg, 169.55 umol, 1 eq.), $K_3PO_4$ (71.98 mg, 339.10 umol, 2 eq.) and XPhos Pd G3 (14.35 mg, 16.95 umol, 0.1 eq.) and then the mixture was stirred at 60° C. for 8 hr under $N_2$ atmosphere. The reaction was concentrated and The residue was purified by prep-TLC (SiO$_2$, DCM: MeOH=15:1) to give (3aR,7aS)-3a-(3-(benzyloxy)-4-methoxy-2-vinylphenyl)-1-methyl-3,3a,7,7a-tetrahydro-1H-indol-6(2H)-one (50 mg, 2.94 mmol, 70.07% yield) as a yellow solid.

1H NMR (400 MHz, CDCl3) δ=7.48 (d, J=7.2 Hz, 1H), 7.40 (d, J=7.2 Hz, 1H), 7.34-7.24 (m, 3H), 7.09-6.90 (m, 2H), 6.80-6.58 (m, 2H), 6.06 (d, J=10.0 Hz, 1H), 5.64 (d, J=17.6 Hz, 1H), 5.21 (d, J=12.4 Hz, 1H), 5.01-4.83 (m, 2H), 3.84-3.78 (m, 3H), 3.32-3.18 (m, 1H), 2.98 (s, 1H), 2.67-2.59 (m, 1H), 2.46-2.34 (m, 2H), 2.27 (d, J=3.6 Hz, 2H), 2.22-2.09 (m, 2H).

Example 17

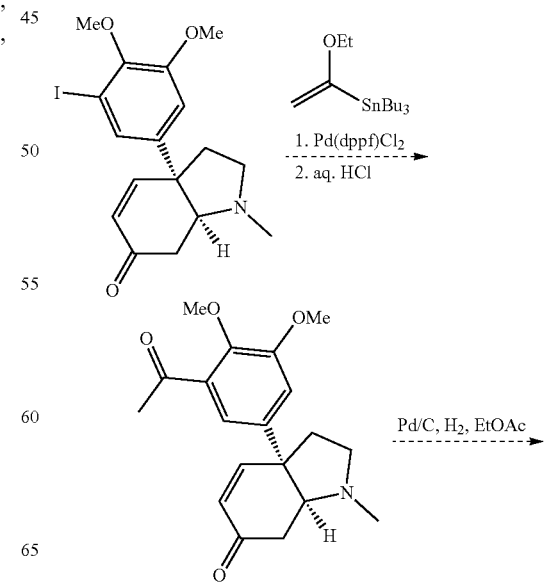

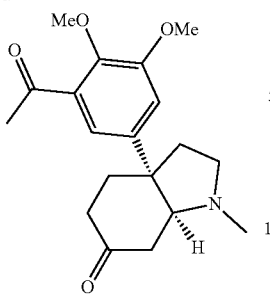

Example 18: Synthesis of (825) and (826)

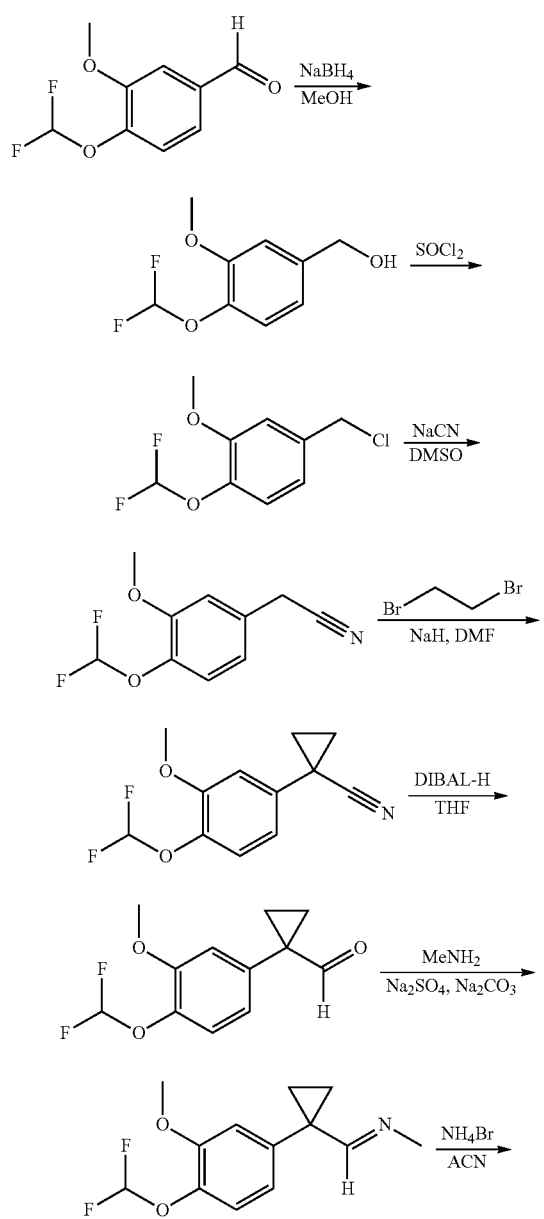

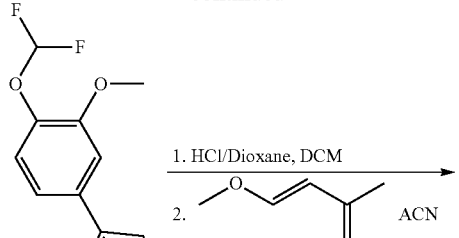

825 racemate     826 racemate

Step 1: Synthesis of [4-(difluoromethoxy)-3-methoxy-phenyl]methanol

To a solution of 4-(difluoromethoxy)-3-methoxy-benzaldehyde (20 g, 98.9 mmol) in MeOH (600 mL) was added NaBH$_4$ (3.74 g, 98.9 mmol) at 0° C. The mixture was allowed to stir at 25° C. for 3 hr. The reaction mixture was added saturated aqueous NH$_4$Cl solution (200 mL). The aqueous solution was extracted with ethyl acetate (100 mL×2). The organic solutions was combined, dried over anhydrous Na$_2$SO$_4$, filtered and concentrated under reduced pressure to give 4-(difluoromethoxy)-3-methoxy-phenyl]methanol (20 g, 69%) as a white oil. $^1$H NMR (400 MHz, CDCl$_3$) δ 2.84-2.78 (m, 4H), 2.59 (J=15.2 Hz, 1H), 2.38 (J=15.2 Hz, 1H), 2.03-1.91 (m, 1H), 1.51-1.39 (m, 1H), 1.38-1.24 (m, 1H), 1.03 (d, J=6.8 Hz, 3H), 0.91 (t, J=7.2 Hz, 3H).

Step 2: Synthesis of 4-(chloromethyl)-1-(difluoromethoxy)-2-methoxy-benzene

A solution of [4-(difluoromethoxy)-3-methoxy-phenyl]methanol (20 g, 97.9 mmol) in SOCl$_2$ (29 mL) was allowed to stir at 70° C. for 3 hr. The reaction mixture was concentrated in vacuo to give 4-(chloromethyl)-1-(difluoromethoxy)-2-methoxy-benzene (20 g, 64%) as a white oil. $^1$H NMR (400 MHz, CDCl$_3$) δ 7.13 (d, J=8.4 Hz, 1H), 7.04-6.88 (m, 2H), 6.56 (t, J=76 Hz, 1H), 4.61-4.49 (m, 2H), 3.96-3.85 (m, 3H).

Step 3: Synthesis of 2-[4-(difluoromethoxy)-3-methoxy-phenyl]acetonitrile

To a solution of 4-(chloromethyl)-1-(difluoromethoxy)-2-methoxy-benzene (20 g, 89.8 mmol) in DMSO (350 mL)

was added NaCN (8.81 g, 180 mmol). The mixture was allowed to stir at 25° C. for 12 hr. The reaction mixture was quenched by the addition of saturated aqueous NaOH (300 mL) to adjust the solution pH to >9. The aqueous solution was extracted with ethyl acetate (500 mL×2). The organic solutions were combined, dried over anhydrous $Na_2SO_4$, filtered and concentrated under reduced pressure. The residue was purified by column chromatography ($SiO_2$, Petroleum ether/Ethyl acetate=3:1) to give 2-[4-(difluoromethoxy)-3-methoxy-phenyl]acetonitrile (9.8 g, 46%) as a white oil. $^1$H NMR (400 MHz, $CDCl_3$) δ 7.16 (d, J=8.0 Hz, 1H), 6.97-6.85 (m, 2H), 6.55 (t, J=76.0 Hz, 1H), 3.90 (s, 3H), 3.75 (s, 2H).

Step 4: Synthesis of 1-4-(difluoromethoxy)-3-methoxy-phenyl]cyclopropanecarbonitrile To a solution of 2-4-(difluoromethoxy)-3-methoxy-phenyl]acetonitrile (8.6 g, 40.3 mmol) and 1,2-dibromoethane (9.09 g, 48.4 mmol, 3.65 mL) in DMF (150 mL) was added NaH (3.23 g, 80.7 mmol, 60% purity). The mixture was allowed to stir at 25° C. for 5 hr. The reaction mixture was quenched by added saturated aqueous $NH_4Cl$ solution (300 mL). The aqueous solution was extracted with ethyl acetate (300 mL×2). The organic solutions were combined, dried over anhydrous $Na_2SO_4$, filtered and concentrated under reduced pressure. The residue was purified by column chromatography ($SiO_2$, Petroleum ether/Ethyl acetate=3:1) to give 1-4-(difluoromethoxy)-3-methoxy-phenyl]cyclopropanecarbonitrile (5.5 g, 46%) as a white oil. $^1$H NMR (400 MHz, $CDCl_3$) δ 7.12 (d, J=8.4 Hz, 1H), 7.00 (d, J=2.4 Hz, 1H), 6.77 (J=2.3, 8.4 Hz, 1H), 6.54 (t, J=76 Hz, 1H), 3.91 (s, 3H), 1.78-1.70 (m, 2H), 1.44-1.35 (m, 2H).

Step 5: Synthesis of 1-[4-(difluoromethoxy)-3-methoxy-phenyl]cyclopropanecarbaldehyde To a solution of 1-[4-(difluoromethoxy)-3-methoxy-phenyl]cyclopropanecarbonitrile (5.5 g, 23.0 mmol) in THF (80 mL) was added DIBAL-H (1 M in THF, 34.49 mL) at −78° C. The mixture was allowed to stir at −78 and allowed to warm to −25° C. over 5 hr. To the reaction mixture was added cold 2 M HCl solution (200 mL). The aqueous solution was extracted with ethyl acetate (100 mL×2). The organic solutions were combined, dried over anhydrous $Na_2SO_4$, filtered and concentrated under reduced pressure to give 1-[4-(difluoromethoxy)-3-methoxy-phenyl]cyclopropanecarbaldehyde (5.6 g, 70%) as a white oil. $^1$H NMR (400 MHz, $CDCl_3$) δ 9.07 (s, 1H), 7.11-7.02 (m, 1H), 6.87-6.74 (m, 2H), 6.46 (t, J=76 Hz, 1H), 3.80-3.80 (m, 1H), 3.80 (s, 2H), 1.53-1.47 (m, 2H), 1.37-1.28 (m, 2H).

Step 6: Synthesis of (E)-1-[1-[4-(difluoromethoxy)-3-methoxy-phenyl]cyclopropyl]-N-methyl-methanimine To a solution of 1-[4-(difluoromethoxy)-3-methoxy-phenyl]cyclopropanecarbaldehyde (5.6 g, 23.1 mmol) and methanamine hydrochloride (7.80 g, 116 mmol) in DCM (150 mL) was added $Na_2SO_4$ (49.3 g, 347 mmol) and $Na_2CO_3$ (7.35 g, 69.4 mmol). The mixture was allowed to stir at 25° C. for 12 hr. The reaction mixture was filtered and the filtrate was concentrated under reduced pressure to give (E)-1-[1-[4-(difluoromethoxy)-3-methoxy-phenyl]cyclopropyl]-N-methyl-methanimine (5.5 g, 65%) as a white oil. $^1$H NMR (400 MHz, $CDCl_3$) δ 9.15 (s, 1H), 7.16-7.04 (m, 1H), 6.98-6.81 (m, 1H), 6.76-6.31 (m, 1H), 3.92-3.80 (m, 3H), 3.24 (d, J=0.8 Hz, 2H), 2.56 (s, 3H), 1.31-1.24 (m, 2H), 1.20-1.14 (m, 2H).

Step 7: Synthesis of 4-[4-(difluoromethoxy)-3-methoxy-phenyl]-1-methyl-2,3-dihydropyrrole To a solution of (E)-1-[1-[4-(difluoromethoxy)-3-methoxy-phenyl]cyclopropyl]-N-methyl-methanimine (400 mg, 1.57 mmol) in ACN (12 mL) was added ammonia hydrobromide (154 mg, 1.57 mmol, 63.2 uL). The mixture was allowed to stir at 120° C. for 2 hr. The reaction mixture was concentrated in vacuo to give 4-[4-(difluoromethoxy)-3-methoxy-phenyl]-1-methyl-2,3-dihydropyrrole (1.3 g, 43%) as a white oil. LC-MS (ESI$^+$) m/z 256.2 (M+H)$^+$.

Step 8: Synthesis of (825)

To a solution of 4-[4-(difluoromethoxy)-3-methoxy-phenyl]-1-methyl-2,3-dihydropyrrole (1.3 g, 5.09 mmol) in DCM (6 mL) was added HCl/dioxane (4 M, 2.55 mL). The mixture was allowed to stir at 25° C. for 10 min and then concentrated under reduced pressure. The residue and 4-methoxybut-3-en-2-one (561 mg, 5.60 mmol) were dissolved in ACN (15 mL). The mixture was allowed to stir at 90° C. for 16 hr. The reaction mixture was quenched by the addition of cold saturated aqueous $NH_4Cl$ solution (30 mL). The aqueous solution was extracted with ethyl acetate (30 mL×2). The organic solutions were combined, dried over anhydrous $Na_2SO_4$, filtered and concentrated under reduced pressure. The residue was purified by prep-HPLC (column: Phenomenex C18 250*50 mm*10 um; mobile phase: [water (ammonia hydroxide v/v)-ACN]; B %: 26%-56%, 8 min) to give 825 (50 mg, 26%) as a white oil. LC-MS (ESI$^+$) m/z 323.9 (M+H)$^+$.

Step 9: Synthesis of (826)

To a solution of 825 (50 mg, 154.64 umol) in THF (3 mL) was added Pd/C (5 mg, 155 umol, 10% purity). The mixture was allowed to stir at 25° C. for 3 hr under an atmosphere of $H_2$. The reaction mixture was filtered and the filtrate was concentrated under reduced pressure to give 825 (50 mg, 89%) as a white oil. LC-MS (ESI$^+$) m/z 326.2 (M+H)$^+$. $^1$H NMR (400 MHz, $CDCl_3$) δ 7.15 (d, J=8.4 Hz, 1H), 7.02-6.92 (m, 2H), 6.56 (t, J=76 Hz, 1H), 3.99-3.84 (m, 3H), 3.80-3.69 (m, 1H), 3.22-3.10 (m, 1H), 2.95 (t, J=3.2 Hz, 1H), 2.61 (d, J=3.6 Hz, 2H), 2.49-2.44 (m, 1H), 2.36-2.31 (m, 3H), 2.25-2.10 (m, 4H), 1.90-1.83 (m, 1H).

Example 19: SFC Separation of (826) to give (385) and (421)

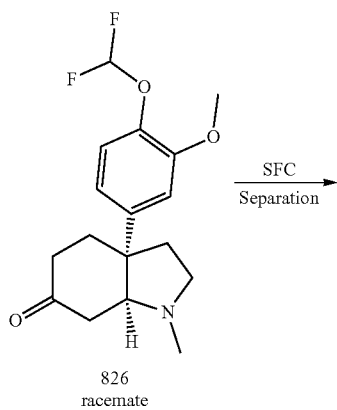

826
racemate

-continued

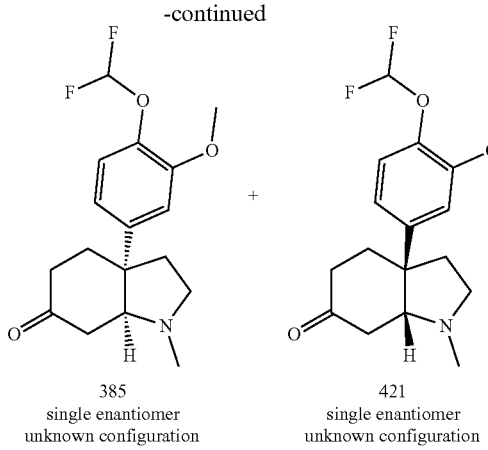

385
single enantiomer
unknown configuration 421
single enantiomer
unknown configuration The enantiomers of 826 were separated by SFC (column: Daicel ChiralPak IG (250*30 mm, 10 um); mobile phase: [0.1% NH$_3$H$_2$O MeOH]; B %: 25%-25%, A3.6; 45 min) to give 385 (31 mg, 62%) as a yellow gum and 421 (24 mg, 49%) as a yellow gum.

385: LC-MS (ESI$^+$) m/z 326.2 (M+H)$^+$ $^1$H NMR (400 MHz, CDCl$_3$) δ 7.15 (d, J=8.0 Hz, 1H), 7.02-6.88 (m, 2H), 6.76-6.32 (m, 1H), 3.91 (s, 3H), 3.24-3.08 (m, 1H), 3.03-2.88 (m, 1H), 2.70-2.55 (m, 2H), 2.49-2.42 (m, 1H), 2.34 (s, 3H), 2.27-2.19 (m, 2H), 2.19-2.13 (m, 2H), 1.32-1.25 (m, 2H). 421: LC-MS (ESI$^+$) m/z 326.2 (M+H)$^+$ $^1$H NMR (400 MHz, CDCl$_3$) δ 7.15 (d, J=8.4 Hz, 1H), 7.03-6.86 (m, 2H), 6.56 (t, J=75.2 Hz, 1H), 3.91 (s, 3H), 3.34-3.14 (m, 1H), 3.12-2.92 (m, 1H), 2.68-2.62 (m, 1H), 2.53-2.42 (m, 2H), 2.40 (br s, 3H), 2.25-2.12 (m, 4H), 1.37-1.31 (m, 1H), 1.26 (s, 2H).

Example A1: SERT Inhibition Assay

SERT inhibition was measured using a Neruotransmitter Transportation Fluorescence assay. Briefly, stable 5HTT cells were prepared in a 384 microwell plate. Compounds were prepared by in assay buffer (20 mM HEPES, 0.1% BSA). The compounds were added to the plated cells and incubated for 30 minutes at 37° C. 25 μL of dye solution (Molecular Devices Neurotransmitter Transporter Uptake Assay Kit) is added per well and incubated for 30 minutes at 37° C. The plates are then read on a plate reader.

The results are provided as follows: A: IC50</=50 nM or lower; B: 50 nM<IC50</=100 nM; C: 100 nM<IC50</=500 nM; D: 500 nM<IC50</=1 micromolar; E: IC50>1 micromolar. A SERT inhibition IC$_{50}$ value of below 1 micromolar was obtained for each of Compounds 130, 132, and 133 and over 1 micromolar for Compound 144 using the SERT Inhibition Assay of Example A1.

| Compound | SERT IC$_{50}$ |
|---|---|
| 130 | D |
| 132 | C |
| 133 | C |
| 144 | E |

Example A2: PDE4 Inhibition Assay

Recombinant PDE Assay
Recombinant PDE assay inhibition can be measured according to the BPSBioscience PDE4 assay kit, as described below.
Step 1:
1) Dilute 20 M FAM-Cyclic-3', 5'-AMP stock 100-fold with PDE buffer to make a 200 nM solution. Make only sufficient quantity needed for the assay; store remaining 20 M stock solution in aliquots at −20° C.
2) Add 25 μl of FAM-Cyclic-3',5'-AMP (200 nM) to each well designated "Positive Control", "Test Inhibitor", and "Substrate Control".
3) Add 20 μl of PDE assay buffer to each well designated "Substrate Control" and 45 μl of PDE assay buffer to each well designated "Blank".
4) Add 5 μl of inhibitor solution to each well designated "Test Inhibitor". For the wells labeled "Positive Control", "Substrate Control" and "Blank", add 5 μl of the same solution without inhibitor (inhibitor buffer).
5) Thaw PDE on ice. Upon first thaw, briefly spin tube containing enzyme to recover the full contents of the tube.
6) Dilute PDE4 in PDE buffer to 7.5 pg/μl (0.15 ng/reaction)*. Initiate reaction by adding 20 μl of PDE4 (7.5 pg/μl) to the wells designated "Positive Control" and "Test Inhibitor."
7) Incubate at room temperature for 1 hour.
Step 2:
1) Mix binding agent thoroughly and dilute binding agent 1:100 with binding agent diluent.
2) Add 100 μl diluted binding agent to each microwell. Incubate at room temperature for 1 hour with slow shaking.
3) Read the fluorescent polarization of the sample in a microtiter-plate reader equipped for the measurement of fluorescence polarization, capable of excitation at wavelengths ranging from 485±5 nm and detection of emitted light ranging from 528±10 nm. Blank value is subtracted from all other values.
Cell-Based Assay
Cells can be dispensed at a density of 1000 cells/well in black, clear bottom, tissue culture treated, 1536 well plates (Kalypsys, San Diego, CA) in 3 μl assay medium containing DMEM, 2% FBS, 50 units/mL penicillin and 50 μg/mL streptomycin and can be incubated 24 hr at 37° C. with 5% CO$_2$ prior to compound screening. 3 μl/well of 1× membrane potential dye was added and incubated for 1 hr at the room temperature. The library compounds in DMSO solution or the positive control, RO 20-1724, can be added at 23 nL/well with a Pintool Station (Kalypsys, San Diego, CA). After a 30-minute incubation with compounds at the room temperature, the assay plate can be measured in an Envision fluorescence plate reader (PerkinElmer, Woburn, MA) in bottom reading mode with an excitation of 535 (±20) nm and emission of 590 (±20) nm. A flying reagent dispensing (FRD) workstation (Aurora Discovery, San Diego, CA) can be used to dispense cells and reagents to 1536-well plates. The Kalypsys Pintool Station can be used to transfer 23 nL compounds in DMSO solution to the 1536-well assay plate. The final DMSO concentration in the assay plates can be under 0.5%.

An IC$_{50}$ value of 1-10 micromolar was obtained for Compound 133 for each of PDE4A1A, and PDE4B2 using the recombinant PDE4 Inhibition Assay of Example A2. IC$_{50}$ values of above 10 micromolar were obtained for Compounds 130, 132 and 144 for PDE4A1A and PDE4B2 using the recombinant PDE4 Inhibition Assay of Example A2. $IC_{50}$ values of above 10 micromolar was obtained for PDE4C1 and PDE4D2 for each of Compounds 130, 132, 133 and 144 using the recombinant PDE4 Inhibition Assay of Example A2.

The invention claimed is:

1. A compound of Formula (IB):

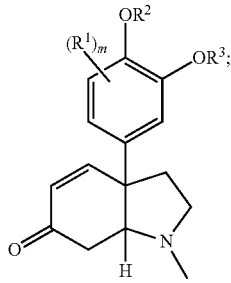

(IB)

or a pharmaceutically acceptable salt thereof; wherein $R^1$ is halo;

$R^2$ is methyl or halomethyl;

$R^3$ is methyl, halomethyl, or benzyl; and m is 1, 2, or 3.

2. The compound of claim 1, or a pharmaceutically acceptable salt thereof, wherein the compound is a compound of Formula (IB-2):

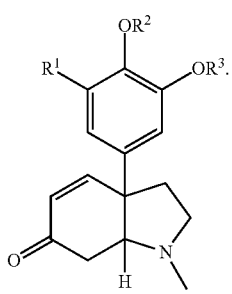

(IB-2)

3. The compound of claim 2, or a pharmaceutically acceptable salt thereof, wherein $R^2$ is methyl; and $R^3$ is methyl.

4. The compound of claim 1, or a pharmaceutically acceptable salt thereof, wherein $R^2$ is methyl; and $R^3$ is methyl.

5. The compound of claim 1, or a pharmaceutically acceptable salt thereof, wherein $R^2$ is methyl optionally substituted with one or more fluoro; and $R^3$ is methyl optionally substituted with one or more fluoro.

6. The compound of claim 1, selected from the group consisting of:

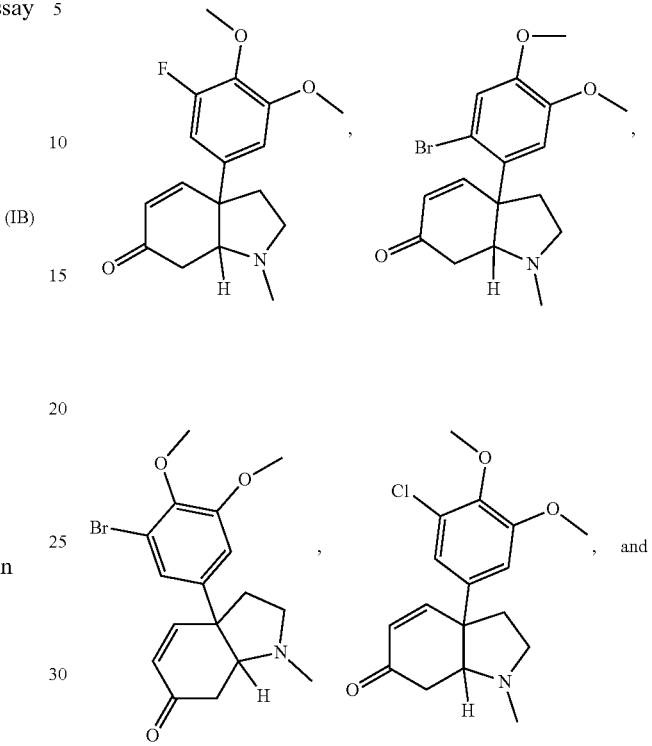

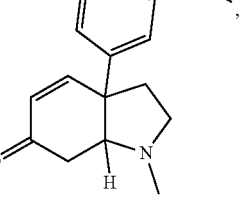

or a pharmaceutically acceptable salt thereof.

7. The compound of claim 1, wherein the compound is

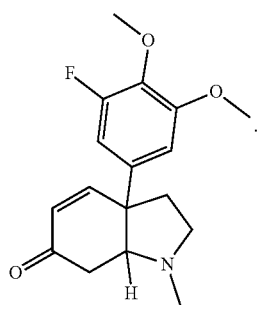 [SMILES: COc1cc(C23C=CC(=O)CC2N(C)CC3)cc(F)c1OC]

8. A compound of Formula (IB-1):

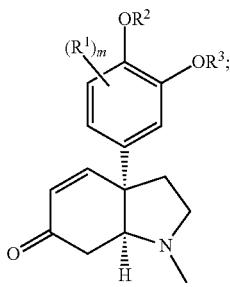

(IB-1)

or a pharmaceutically acceptable salt thereof; wherein
$R^1$ is halo;
$R^2$ is methyl or halomethyl;
$R^3$ is methyl, halomethyl, or benzyl; and
m is 1, 2, or 3.

9. The compound of claim 8, wherein the compound is a compound of Formula I (IB-4) or a pharmaceutically acceptable salt thereof:

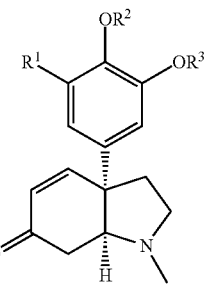

(IB-4).

10. The compound of claim 9, wherein $R^1$ is iodo.

11. The compound of claim 9, wherein $R^1$ is bromo.

12. The compound of claim 9, wherein $R^1$ is fluoro.

13. The compound of claim 12, wherein $R^2$ is methyl.

14. The compound of claim 13, wherein $R^3$ is methyl.

15. The compound of claim 8, wherein $R^1$ is fluoro, chloro, bromo, or iodo.

16. The compound of claim 15, wherein $R^2$ is methyl.

17. The compound of claim 16, wherein $R^3$ is methyl.

* * * * *